US007091331B2

(12) United States Patent
Tamura et al.

(10) Patent No.: US 7,091,331 B2
(45) Date of Patent: Aug. 15, 2006

(54) NUCLEIC ACID MOLECULES AND POLYPEPTIDES ENCODING BABOON TAFI

(75) Inventors: James K. Tamura, Yardley, PA (US); Gary R. Matsueda, Princeton, NJ (US); Mei-Yin Hsu, Hillsboro, NJ (US); Akbar Nayeem, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 363 days.

(21) Appl. No.: 10/379,836

(22) Filed: Mar. 4, 2003

(65) Prior Publication Data

US 2003/0215850 A1 Nov. 20, 2003

Related U.S. Application Data

(60) Provisional application No. 60/361,523, filed on Mar. 4, 2002.

(51) Int. Cl.
*C07H 21/01* (2006.01)
*C07H 21/04* (2006.01)
*C07K 1/14* (2006.01)

(52) U.S. Cl. .................... 536/23.5; 536/23.1; 530/350; 530/395

(58) Field of Classification Search ............... 536/23.1, 536/23.5; 530/350
See application file for complete search history.

(56) References Cited

U.S. PATENT DOCUMENTS

| | | | |
|---|---|---|---|
| 5,010,175 | A | 4/1991 | Rutter et al. |
| 5,206,161 | A | 4/1993 | Drayna et al. |
| 5,288,514 | A | 2/1994 | Ellman |
| 5,364,934 | A | 11/1994 | Drayna et al. |
| 5,474,901 | A | 12/1995 | Drayna et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,593,674 | A | 1/1997 | Drayna et al. |
| 5,593,853 | A | 1/1997 | Chen et al. |
| 5,985,562 | A * | 11/1999 | Morser et al. .......... 435/6 |
| 6,020,141 | A | 2/2000 | Pantoliano et al. |
| 6,036,920 | A | 3/2000 | Pantoliano et al. |
| 6,455,294 | B1 | 9/2002 | Gan et al. |
| 6,818,429 | B1 | 11/2004 | Gan et al. |
| 2003/0017574 | A1 | 1/2003 | Gan et al. |
| 2004/0006205 | A1 | 1/2004 | Li et al. |
| 2005/0042670 | A1 | 2/2005 | Gan et al. |

FOREIGN PATENT DOCUMENTS

| | | |
|---|---|---|
| EP | 1 531 333 A1 | 11/2003 |
| WO | WO 91/19735 | 12/1991 |
| WO | WO 92/00091 | 1/1992 |
| WO | WO 93/20242 | 10/1993 |
| WO | WO 98/55645 | 12/1998 |
| WO | WO 00/55180 | 9/2000 |
| WO | WO 00/66717 | 11/2000 |
| WO | WO03/014391 A2 | 2/2002 |
| WO | WO 02/083841 A2 | 10/2002 |
| WO | WO 04/020587 A2 | 3/2004 |
| WO | WO 04/083403 A2 | 9/2004 |

OTHER PUBLICATIONS

NCBI Entrez Accession No. gi|231202, Rees, D.C. et al., Oct. 7, 1998.
NCBI Entrez Accession No. gi|21465928, Barbosa Pereira, P.J. et al., Jan. 30, 2002.
NCBI Entrez Accession No. gi:4503005, Zhao, L. et al., Dec. 20, 2003.
Morange, et al., "Ala147Thr and C+1542G Polymorphisms in the TAFI Gene Are Not Associated With A Higher Risk Of Venous Thrombosis In FV Leiden Carriers", Thromb Haemost, vol. 86, pp. 1583-1584 (2001).
Libourel, et al., "Co-Segregation Of Thrombophilic Disorders In Factor V Leiden Carriers; The Contributions Of Factor VIII, Factor XI, Thrombin Activatable Fibrinolysis Inhibitor And Lipoprotein(a) To The Absolute Risk Of Venous Thromboembolism", Haematologica, vol. 87, pp. 1068-1073 (2002).

(Continued)

*Primary Examiner*—Jon Weber
*Assistant Examiner*—Suzanne M. Noakes
(74) *Attorney, Agent, or Firm*—Stephen C. D'Amico

(57) ABSTRACT

The present invention relates to the isolation and identification of novel baboon nucleic acid molecules and proteins and polypeptides encoded by such nucleic acid molecules, or degenerate variants thereof, which proteins and polypeptides comprise novel baboon thrombin-activatable fibrinolysis inhibitors or "TAFI" enzyme molecules. Because the novel baboon TAFI proteins and polypeptides of the invention inhibit the breakdown of blood clots, they may be therapeutically useful for the treatment of blood disorders wherein clotting needs to be regulated or promoted, such as hemophilia or von Willebrand's disease or in other situations, such as trauma, wherein blood clotting or coagulation needs to be regulated or promoted. The sequences of the invention are also useful in screening methods for the identification of compounds that modulate the expression of the baboon TAFI nucleic acids and/or the activity of the baboon TAFI proteins and polypeptides of the invention. Such agonist or antagonist compounds may be useful in the treatment of various blood clotting disorders and conditions requiring hemostatic control such as hemophilia or various thrombotic diseases such as deep venous thrombosis, coronary artery disease, stroke associated with atrial fibrillation and recurrent thrombosis following stroke or myocardial infarction.

23 Claims, 15 Drawing Sheets

OTHER PUBLICATIONS

Tsai, et al., "The Gene Encoding Human Plasma Carboxypeptidase B (CPB2) Resides On Chromosome 13", Genomics, vol. 14, pp. 549-550 (1992).
Zhao, et al., "Identification And Characterization Of Two Thrombin-Activatable Fibrinolysis Inhibitor Isoforms", Thromb Haemost, vol. 80, pp. 949-955 (1998).
Antovic, et al., "Does Thrombin Activatable Fibrinolysis Inhibitor (TAFI) Contribute To Impairment Of Fibrinolysis In Patients With Preeclampsia And/Or Intrauterine Fetal Growth Retardation?", Thromb Haemost, vol. 88, pp. 644-647 (2002).
Pascual, et al., "Purification And Properties Of Five Different Forms Of Human Procarboxypeptidases", Eur. J. Biochem., vol. 179, pp. 609-616 (1989).
Matsumoto, et al., "A Novel Carboxypeptidase B that Processes Native β-amyloid Precursor Protein Is Present In Human Hippocampus", Eur. J. of Neuroscience, vol. 12, pp. 227-238 (2000).
Zhao, et al., "Mutations In The Substrate Binding Site Of Thrombin-Activatable Fibrinolysis Inhibitor (TAFI) Alter Its Substrate Specificity", J. Biol. Chem., vol. 278, pp. 32359-32366 (2003).
Colucci, et al., "Deficiency Of Thrombin Activatable Fibrinolysis Inhibitor In Cirrhosis Is Associated With Increased Plasma Fibrinolysis", Hepatology, vol. 38 (1), pp. 230-237 (2003).
Yano, et al., "Increased Plasma Thrombin-Activatable Fibrinolysis Inhibitor Levels In Normotensive Type 2 Diabetic Patients With Microalbuminuria", J. Clin. Endocrin & Metabolism, vol. 88(2), pp. 736-741 (2003).
Yano, et al., "Association Between Plasma Thrombin-Activatable Fibrinolysis Inhibitor Levels And Activated Protein C In Normotensive Type 2 Diabetic Patients", Diabetes Care, vol. 25(7), pp. 1245-1246 (2002).
Schneider, et al., "Amino Acid Residues In The P6-P'3 Region Of Thrombin-Activable Fibrinolysis Inhibitor (TAFI) Do Not Determine The Thrombinomodulin Dependence Of TAFI Activation", J. Biol.Chem., vol. 277(12), pp. 9944-9951 (2002).
Eaton, et al., "Isolation, Molecular Cloning, And Partial Characterization Of A Novel Carboxypeptidase B From Human Plasma", J. Biol. Chem., vol. 266(32), pp. 21833-21838 (1991).
Koschinsky, et al., "Association Of A Single Nucleotide Polymorphism In *CPB2* Encoding The Thrombin-Activable Fibrinolysis Inhibitor (TAFI) With Blood Pressure", Clin. Genet, vol. 60, pp. 345-349 (2001).
Boffa, et al., "Characterization Of The Gene Encoding Human TAFI (Thrombin-Activable Fibrinolysis Inhibitor; Plasma Procarboxypeptidase B)", Biochem., vol. 38, pp. 6547-6558 (1999).
Vanhoof, et al., "The Gene For Human Carboxypeptidase U (CPU)-A Proposed Novel Regulator Of Plasminogen Activation-Maps To 13q14.11", Genomics, vol. 38, pp. 454-455 (1996).
NCBI Entrez Accession No. 105544 (gi:105544) Eaton, D.L., et al., Aug. 26, 1999.
NCBI Entrez Accession No. AAA60042 (gi:189687) Eaton, D.L., et al., Jan. 7, 1995.
NCBI Entrez Accession No. AAA94971 (gi:1253712) Drayna, D.T., et al., Apr. 3, 1996.
NCBI Entrez Accession No. AAB45836 (gi:1831382) Drayna, D.T., et al., Feb. 7, 1997.
NCBI Entrez Accession No. AAE36249 (gi:10059544) Morser, M.J., et al., Sep. 7, 2000.
NCBI Entrez Accession No. AAP36662 (gi:30584819) Kalnine, N., et al., May 13, 2003.
NCBI Entrez Accession No. AAW13792 (gi:56646729) Gan, W., et al., Dec. 15, 2004.
NCBI Entrez Accession No. AAX29427 (gi:60653465) Hines, L., et al., Mar. 29, 2005.
NCBI Entrez Accession No. AAX29428 (gi:60653467) Hines, L., et al., Mar. 29, 2005.
NCBI Entrez Accession No. CAI10905 (gi:55859590) Griffiths, C., May 18, 2005.
NCBI Entrez Accession No. Q96IY4 (gi:62899885) Eaton, D.L., Feb. 7, 2006.
NCBI Entrez Accession No. XP_007121 (gi:11434004) NCBI Annotation Project, Jul. 16, 2001.
NCBI Entrez Accession No. XP_165638 (gi:20547646) NCBI Annotation Project, May 13, 2002.
Antovic, J.P. et al., "Thrombin-activatable fibrinolysis inhibitor antigen and TAFI activity in patients with APC resistance caused by factor V Leiden mutation", Thrombosis Research, vol. 106, pp. 59-62 (2002).
Antovic, J.P. et al., "Does thrombin activatable Fibrinolysis inhibitor (TAFI) Contribute to Impairment of Fibrinolysis in Patients with Preeclampsia and/or Intrauterine Fetal Growth Retardation?", Thromb Haemost, vol. 88, pp. 644-647 (2002).
Antovic, J.P. et al., "Does an enzyme other than thrombin contribute to unexpected changes in the levels of the different forms of thrombin activatable fibrinolysis inhibitor in patients with hemophilia A, hemophilia B and von Willebrand disease?", Scand J Clin Lab Invest, vol. 64, pp. 745-752 (2004).
Aso, Y. et al., "Metabolic syndrome accompanied by Hypercholesterolemia is strongly associated with Proinflammatory State and Impairment of Fibrionlysis in Patients with type 2 Diabetes", Diabetes Care, vol. 28(9), pp. 2211-2216 (2005).
Boffa, M.B. et al., "Acute Phase Mediators Modulate Thrombin-activable Fibrinolysis Inhibitor (TAFI) Gene Expression in HepG2 Cells*", The J. of Biological Chemistry, vol. 278(11), pp. 9250-9257 (2003).
Bouma, B. et al., "Thrombin Activatable Fibrinolysis Inhibitor (TAFI) at the Interface between Coagulation and Fibrinolysis", Pathophysiology of Haemostasis and Thrombosis, vol. 33, pp. 375-381 (2003).
Brouwers, G.J. et al., "Association between thrombin-activatable fibrinolysis inhibitor (TAFI) and clinical outcome in patients with unstable angina pectoris", Thromb Haemost, vol. 90, pp. 92-100 (2003).
Colucci, M. et al., "Deficiency of Thrombin Activatable Fibrinolysis Inhibitor in Cirrhosis is Associated with Increased Plasma Fibrinolysis", Hepatology, vol. 38, pp. 230-237 (2003).
Donmez, A. et al., "Thrombin activatable fibrinolysis inhibitor in Behçet's disease", Thrombosis Research, vol. 115, pp. 287-292 (2005).
Dunham, A. et al., "The DNA sequence and analysis of human chromosome 13", Nature, vol. 428, pp. 522-528 (2004).
Eichinger, S. et al., "Thrombin-activatable fibrinolysis inhibitor and the risk for recurrent venous thromboembolism", Blood, vol. 103(10), pp. 3773-3776 (2004).
Hataji, O. et al., "Increased Circulating Levels of Thrombin-activatable Fibrinolysis Inhibitor in Lung Cancer Patients", American J. of Hematology, vol. 76, pp. 214-219 (2004).
Hori, Y. et al., "Insulin enhanced thrombin-activable fibrinolysis inhibitor expression through PI3 kinase/Akt pathway", International J. of Molecular Medicine, vol. 15, pp. 265-268 (2005).
Kochinsky, ML. et al., "Association of a single nucleotide polymorphism in *CPB2* encoding the thrombin-activable fibrinolysis inhibitor (TAFI) with blood pressure", Clinical Genetics, vol. 60, pp. 345-349 (2001).
Kremer Hovinga, J. et al., "A functional single nucleotide polymorphism in he thrombin-activatable fibrinolysis inhibitor (TAFI) gene associates with outcome of meningococcal disease", J. of Thrombosis and Haemostasis, vol. 2, pp. 54-57 (2003).
MGC Program Team, "Generation and initial analysis of more than 15,000 full-length human and mouse cDNA sequences", PNAS, vol. 99(26), pp. 16899-16903 (2002).
Maret, D. et al., "Role mRNA transcript stability in modulation of expression of the gene encoding thrombin activable fibrinolysis inhibitor", J. of Thrombosis and Haemostasis, vol. 2, pp. 1969-1979 (2004).
Morange, P.E. et al., "Ala147Thr and C+1542G Polymorphisms in the TAFI gene are not Associated with a Higher Risk of Venous Thrombosis in FV Leiden Carriers", Thromb Haemost, vol. 86, pp. 1583-1584 (2001).
Morange, P.E. et al., "Association between TAFI antigen and Ala147Thr polymorphism of the TAFI gene and the angina pectoris incidence", Thromb Haemost, vol. 89, pp. 554-560 (2003).
Morange, P.E. et al., "TAFI gene haplotypes, TAFI plasma levels and future risk of coronary heart disease: the PRIME Study", J. of Thrombosis & Haemostasis, vol. 3, pp. 1503-1510 (2005).

Mosnier, L. O. et al., "Identification of thrombin activatable fibrinolysis inhibitor (TAFI) in human platelets", Blood, vol. 101(12), pp. 4844-4846 (2003).

Mosnier, L.O. et al., "The Role of Protein S in the Activation of Thrombin Activatable Fibrinolysis (TAFI) and Regulation of Fibrinolysis", Thromb Haemost, vol. 86, pp. 1040-1046 (2001).

Mosnier, L.O. et al., "Protein C Inhibitor Regulates the Thrombin-Thrombomodulin Complex in the Up- and Down Regulation of TAFI Activation", Thromb Haemost, vol. 86, pp. 1057-1064 (2001).

Mosnier, L.O. et al., "The Defective Down Regulation of Fibrinolysis in Haemophilia A can be Restored by Increasing the TAFI Plasma Concentration", Thromb Haemost, vol. 86, pp. 1035-1039 (2001).

Mousa, H.A. et al., "Thrombin activatable fibrinolysis inhibitor and its fibrinolytic effect in normal pregnancy", Thromb Haemost, vol. 92, pp. 1025-1031 (2004).

Mutch, N.J. et al., "Thrombus lysis by uPA, scuPA and tPA is regulated by plasma TAFI", J of Thrombosis and Haemostasis, vol. 1, pp. 2000-2007 (2003).

Myles, T. et al., "Thrombin Activatable Fibrinolysis Inhibitor, a Potential Regulator of Vascular Inflammation*", The J of Biological Chemistry, vol. 278(51), pp. 51059-51067 (2003).

Olszanski, R. et al., "Diving up to 60 m depth followed by decompression has no effect on pro-enzyme and total thrombin activatable fibrinolysis inhibitor antigen concentration", Blood Coagul Fibrinolysis, vol. 14, pp. 659-661 (2003).

Ravindranath, T.M. et al., "Tissue Factor Pathway Inhibitor and Thrombin Activatable Fibrinolytic Plasma Levels following Burn and Septic Injuries in Rats", Clin Appl Thrombosis/Hemostasis, vol. 10(4), pp. 379-385 (2004).

Reijerkerk, A. et al., "Tumor growth and metastasis are not affected in thrombin-activatable fibrinolysis inhibitor-deficient mice", J. of Thrombosis and Haemostasis, vol. 2, pp. 769-779 (2003).

Schneider, M. et al., "Amino Acid Residues in the P6-P'3 Region of Thrombin-activable Fibrinolysis Inhibitor (TAFI) Do Not Determine the Thrombomodulin Dependence of TAFI Activation*", The J of Biological Chemistry, vol. 277(12), pp. 9944-9951 (2002).

Schneider, M. et al., "Activated Thrombin-activatable Fibrinolysis Inhibitor Reduces the Ability of High Molecular Weight Fibrin Degradation Products to Protect Plasmin from Antiplasmin*", The J of Biological Chemistry, vol. 279(14), pp. 13340-13345 (2004).

Schroeder, V. et al., "Role of thrombin activatable fibrinolysis inhibitor (TAFI) in patients with acute pulmonary embolism", J of Thrombosis and Haemostasis, vol. 1, pp. 492-493 (2002).

Swaisgood, C. et al., "In vivo regulation of plasminogen function by plasma carboxypeptidase B", J. Clin. Invest., vol. 110, pp. 1275-1282 (2002).

Walker, J.B. et al., "The Intrinsic Threshold of the Fibrinolytic System is Modulated by Basic Carboxypeptidases, but the Magnitude of the Antifibrinolytic Effect of Activated Thrombin-activable Fibrinolysis Inhibitor is Masked by its Instability*", The J of Biological Chemistry, vol. 279(27), pp. 27896-27904 (2004).

Watanabe, T. et al., "Changes in Activity of Plasma Thrombin Activatable Fibrinolysis Inhibitor in Pregnancy", Gynecol Obstet Invest, vol. 58, pp. 19-21 (2004).

Yano, Y. et al., "Increased Plasma Thrombin-Activatable Fibrinolysis Inhibitor Levels in Normotensive Type 2 Diabetic Patients with Microalbuminuria", The J of Clinical Endocrinology & Metabolism, vol. 88(2), pp. 736-741 (2003).

Yano, Y. et al., "Association Between Plasma Thrombin-Activatable Fibrinolysis Inhibitor Levels and Activated Protein C in Normotensive Type 2 Diabetic Patients", Diabetes Care, vol. 25(7), pp. 1245-1246 (2002).

Zhao, L. et al., "Mutations in the Substrate Binding Site of Thrombin-activatable Fibrinolysis Inhibitor (TAFI) Alter its Substrate Specificity", The J of Biological Chemistry, vol. 278(34), pp. 32359-32366 (2003).

Zidane, M. et al., "Frequency of the TAFI-438 G/A and factor XIIIA Val34Leu polymorphisms in patients with objectively proven pulmonary embolism", Thromb Haemost, vol. 90, pp. 439-445 (2003).

Zirlik, A., "TAFI: a promising drug target?", Thromb Haemost, vol. 91, pp. 420-422 (2004).

Altschul, S. et al, "Basic Local Alignment Search Tool", J. Mol. Biol., vol. 215, pp. 403-410 (1990).

Altschul, S. et al, "Gapped BLAST and PSI-BLAST: a new generation of protein database search programs", Nucleic Acids Research, vol. 25, No. 17, pp. 3389-3402 (1997).

Antovic, J.P., et al. "Does an enzyme other than thrombin contribute to unexpected changes in the levels of the different forms of thrombin activatable fibrinolysis inhibitor in patients with hemophilia A, hemophilia B and von Willebrand disease?", Scand J Clin Lab Invest, vol. 64, pp. 745-752 (2004).

Antovic, J.P., et al. "Does Thrombin Activatable Fibrinolysis Inhibitor (TAFI) Contribute to Impairment of Fibrinolysis in Patients with Preeclampsia and/or Intrauterine Fetal Growth Retardation?", Thromb Haemost, vol. 88, pp. 644-647 (2002).

Antovic, J.P., et al. "Thrombin-activatable fibrinolysis inhibior antigen and TAFI activity in patients with APC resistance caused by factor V Leiden Mutation", Thrombosis Research, vol. 106, pp. 59-62 (2002).

Bajzar, L. et al., "TAFI, or Plasma Procarboxypeptidase B, Couples the Coagulation and Fibrinolytic Cascades through the Thrombin-thrombomodulin Complex", The Journal of Biological Chemistry, vol. 271, No. 28 pp. 16603-16608 (1996).

Bajzar, L. et al., "Purification and characterization of TAFI, a Thrombin-activable Fibrinolysis Inhibitor*", The Journal of Biological Chemistry, vol. 270, No. 24, pp. 14477-14484 (1995).

Bartlett, P. et al., "CAVEAT: A Program to Facilitate the Structure-derived Design of Biologically Active Molecules", Molecular Recognition: Chemical and Biochemical Problems, Special Publication No. 78, pp. 182-196 (1989).

Bode, W. et al., "Comparative Analysis of Haemostatic Proteinases: Structural Aspects of Thrombin, Factor Xa, Factor IXa and Protein C", Thrombosis and Haemostasis, vol. 78, No. 1, pp. 501-511 (1997).

Boffa, M. et al., "Characterization of the Gene Encoding Human TAFI (Thrombin-Activable Fibrinolysis Inhibitor; Plasma Procarboxypeptidase B)", Biochemistry, vol. 38, pp. 6547-6558 (1999).

Boffa, M. et al., "Acute Phase Mediators Modulate Thrombin-activable Fibrinolysis Inhibitor (TAFI) Gene Expression in HepG2 Cells*", The Journal of Biological Chemistry, vol. 278, No. 11, pp. 9250-9257 (2003).

Bohm, H. J. et al., "The computer program LUDI: A new method for the de novo design of enzyme inhibitors", Journal of Computer-Aided Molecular Design, vol. 6, pp. 61-78 (1992).

Bouma, B. et al., "Thrombin-Activatable Fibrinolysis Inhibitor (TAFI, Plasma Procarboxypeptidase B, Procarboxypeptidase R, Procarboxypeptidase U", Thrombosis Research, vol. 101, pp. 329-354 (2001).

Bouma, B. et al., "Thrombin Activatable Fibrinolysis Inhibitor (TAFI) at the Interface between Coagulation and Fibrinolysis", Pathophysiol Haemost Tromb vol. 33, pp. 375-381 (2003).

Brouwers, G. J. et al., "Association between thrombin-activatable fibrinolysis inhibitor (TAFI) and clinical outcome in patients with unstable angina pectoris", Thromb Haemost, vol. 90, pp. 92-100 (2003).

Campbell, W. et al., "An Arginine specific Carboxypeptidase generated in Blood during Coagulation or Inflammation which is unrelated to Carboxypeptidase n or its Subunits", Biochemical and Biophysical Research Communication, vol. 162, No. 3, pp. 933-939 (1989).

Campbell, D. et al., "Phosphonate Ester Synthesis Using a Modified Mitsunobu Condensation", J. Org. Chem., vol. 59, pp. 658-660 (1994).

Cardozo, T. et al., "Homology Modeling by the ICM Method", PROTEINS: Structure, Function, and Genetics, vol. 23, pp. 403-414 (1995).

Chen, C. et al., ""Analogous" Organic Synthesis of Small-Compound Libraries: Validation of Combinatorial Chemistry in Small-Molecule Synthesis", vol. 116, pp. 2661-2662 (1994).

Cho, C. et al., "An Unnatural Biopolymer", Science, vol. 261, pp. 1303-1305 (1993).

Colucci, M. et al., "Deficiency of Thrombin Activatable Fibrinolysis Inhibitor in Cirrhosis is Associated with Increased Plasma Fibrinolysis", Hepatology, vol. 38, No. 1, pp. 230-237 (2003).

Czapinska, H. et al., "Structural and energetic determinants of the $S_1$-site specificity in serine proteases", Eur. J. Biochem. vol. 260, pp. 571-595 (1999).

DeWitt, S.H. et al., ""Diversomers": An approach to nonpeptide, nonoligomeric chemical diversity", Proc. Natl. Acad. Sci. USA, vol. 90, pp. 6909-6913 (1993).

Donmez, A. et al., "Thrombin activatable fibrinolysis inhibitor in Behcet's disease", Thrombosis Research, vol. 115, pp. 287-292 (2005).

Eaton, D. et al., "Isolation, Molecular Cloning, and Partial Characterization of a Novel Carboxypeptidase B from Human Plasma*", The Journal of Biological Chemistry, vol. 266, No. 32, pp. 21833-21838 (1991).

Eichinger, S. et al., "Thrombin-activatable fibrinolysis inhibitor and the risk of recurrent venous thromboembolism", Blood, vol. 103, pp. 3773-3776 (2004).

Franco, R. et al., "Identification of polymorphisms in the 5'-untranslated region of the TAFI gene: relationship with plasma TAFI levels and risk of venous thrombosis", Haematologica, vol. 86. pp. 510-517 (2001).

Furka, A. et al., "General method for rapid synthesis of multicomponent peptide mixtures", Int. J. Peptide Protein Res. vol. 37, pp. 487-493 (1991).

Goodford, P. J. et al., "A Computational Procedure for Determining Energetically Favorable Binding Sites on Biologically Important Macromolecules", Journal of Medicinal Chemistry, vol. 28, No. 7, pp. 849-857 (1985).

Goodsell, D. et a., "Automated Docking of Substrates to Proteins by Simulated Annealing", PROTEINS: Structure, Function, and Genetics, vol. 8, pp. 195-202 (1990).

Greer, J. et al., "Comparative Modeling of Homologous Proteins", Methods in Enzymology, vol. 202, pp. 239-252 (1991).

Hagihara, M. et al., "Vinylogous Polypeptides: An Alternative Peptide Backbone", J. Am. Chem. Soc., vol. 114, pp. 6568 (1992).

Hashimoto, M. et al., "Enhancement of Endogenous Plasminogen Activator-induced Thrombolysis by Argatroban and APC and its Control by TAFI, Measured in An Arterial Thrombolysis Model In Vivo Using Rat Mesenteric Arterioles", Thromb Haemost, vol. 87, pp. 110-113 (2002).

Hataji, O. et al., "Increased Circulating Levels of Thrombin-Activatable Fibrinolysis Inhibitor in Lung Cancer Patients", American Journal of Hematology, vol. 76, pp. 214-219 (2004).

Hendlich, M. et al., "Identification of Native Protein Folds Amongst a Large Number of Incorrect Models", J. Mol. Biol., vol. 216, pp. 167-180 (1990).

Hendriks, D. et al., "Characterisation of a Carboxypeptidase in Human Serum Distinct from Carboxypeptidase N", J. Clin. Chem. Clin. Biochem., vol. 27, pp. 277-285 (1989).

Hendriks, D. et al., "Assay of Carboxypeptidase N Activity in Serum by Liquid-Chromatographic Determination of Hippuric Acid", Clin, Chem,, vol. 31. No. 12, pp. 1936-1939 (1985).

Hirschmann, R. et al. "Nonpeptidal Peptidomimetics with a β-D-Glucose Scaffolding. A Partial Somatostatin Agonis Bearing a close structural relationship to a Potent, Selective substance P Antagonist", J. Am. Chem. Soc. vol. 114, pp. 9217-9218 (1992).

Houghten, R. et al. "Generation and use of synthetic peptide combinatorial libraries for basic research and drug recovery", Nature, vol. 354, pp. 84-86 (1991).

Karlin, S. et al., "Methods for assessing the statistical significance of molecular sequence features by using general scoring schemes", Proc. Natl. Acad. Sci USA, vol. 87, pp. 2264-2268, (1990).

Kato, T. et al., "Molecular Cloning and Partial Characterization of Rat Procarboxypeptidase R and Carboxypeptidase N", Microbiol. Immunol., vol. 44, No. 8, pp. 719-728 (2000).

Katz, B. et al., "Engineering inhibitors highly selective for the S1 sites of Ser190 trypsin-like serine protease drug targets", Chemistry & Biology, vol. 8, pp. 1107-1121 (2001).

Kim, H. et al., "Crystal Structure of the Complex of Carboxypeptidase A with a Strongly Bound Phosphonate in a New Crystalline Form: Comparison with Structures of Other Complexes", Biochemistry, vol. 29, pp. 5546-5555 (1990).

Koschinsky, ML. et al., "Association of a single nucleotide polymorphism in *CPB2* encoding the thrombin-activable fibrinolysis inhibitor (TAFI) with blood pressure", Clin Genet, vol. 60, pp. 345-349 (2001).

Kremer Hovinga, JA. et al., "A functional single nucleotide polymorphism in the thrombin-activatable fibrinolysis inhibitor (TAFI) gene associates with outcome of meningococcal disease", Journal of Thrombosis and Haemostasis, vol. 2, pp. 54-57 (2004).

Kuntz, I. et al., "A Geometric Approach to Macromolecule-Ligand Interactions", J. Mol. Biol., vol. 161, pp. 269-288 (1982).

Lee, K. et al., "Inhibition of proteolysis protects hippocampal neurons from ischemia", Proc. Natl. Acad. Sci. USA, vol. 88, pp. 7233-7237 (1991).

Lesk, A. et al., "Homology modelling: inferences from tables of aligned sequences", Current Opinion in Structural Biology, vol. 2, pp. 242-247 (1992).

Liang, R. et al., "Parallel Synthesis and Screening of a Solid Phase Carbohydrate Library", Science, vol. 274, pp. 1520-1522 (1996).

Libourel, E. et al., "Co-segregation of thrombophilic disorders in factor V Leiden carriers; the contributions of factor VIII, factor XI, thrombin activatable fibrinolysis inhibitor and lipoprotein(a) to the absolute risk of venous thromboembolism", Haemotologica, vol. 87,. pp. 1068-1073 (2002).

Maret, D. et al., "Role of mRNA transcript stability in modulation of expression of the gene encoding thrombin activable fibrinolysis inhibitor", J Thromb Haemost, vol. 2. pp. 1969-1979 (2004).

Marinkovic, D., et al., "Purification of Carboxypeptidase B from Human Pancreas", Biochem. J. vol. 163, pp. 253-260 (1977).

Martin, Y., "3D Database searching in Drug Design", Journal of Medicinal Chemistry, vol. 35, No. 12, pp. 2145-2154 (1992).

Marx, P., et al., "Inactivation of Active Thrombin-activable Fibrinolysis Inhibitor takes place by a process that involves Conformational Instability rather than Proteolytic Cleavage", The Journal of Biological Chemistry, vol. 275, No. 17, pp. 12410-12415 (2000).

Marx. P. et al., "Characterization of Mouse Thrombin-activatable Fibrinolysis Inhibitor", Thromb. Haemost, vol. 83, pp. 297-303 (2000).

Matsumoto, A. et al., "A novel carboxypeptidase B that processes native β-amyloid precursor protein is present in human hippocampus", European Journal of Neuroscience, vol. 12, pp. 227-238 (2000).

Morange, P. et al., "Ala147Thr and C+1542G Polymorphisms in the TAFI Gene are not Associated with a Higher risk of Venous Thrombosis in FV Leiden Carriers", Thromb Haemost, vol. 86, pp. 1583-1584 (2001).

Morange, P. et al., "Association between TAFI antigen and Ala147Thr Polymorphism of the TAFI gene and the angina pectoris incidence", Thromb Haemost, vol. 89, pp. 554-560 (2003).

Mosnier, L. et al., "The defective down regulation of Fibrinolysis in Haemophilia A can be restored by Increasing the TAFI Plasma Concentration", Thromb Haemost, vol. 86, pp. 1035-1039 (2001).

Mosnier, L. et al., "Protein C Inhibitor Regulates the Thrombin-Thrombomodulin Complex in the Up- and Down Regulation of TAFI Activation", Thromb Haemost, vol. 86. pp. 1057-1064 (2001).

Mosnier, L. et al., "The Role of Protein S in the Activation of Thrombin Activatable Fibrinolysis Inhibitor (TAFI) and Regulation of Fibrinolysis", Thromb Haemost, vol. 86, pp. 1040-1046 (2001).

Mosnier, L. et al., "Identification of thrombin activatable fibrinolysis inhibitor (TAFI) in human platelets", Blood, vol. 101, No. 12, pp. 4844-4846 (20003).

Mousa, H. et al., "Thrombin activatable fibrinolysis inhibitor and its fibrinolytic effect in normal pregnancy", Thromb. Haemost, vol. 92, pp. 1025-1031, 2004.

Mutch, N.J. et al., "Thrombus lysis by uPA, scuPA and tPA is regulated TAFI", Journal of Thrombosis and Haemostasis, vol. 1, pp. 2000-2007 (2003).

Myles, T. et al., "Thrombin Activatable Fibrinolysis Inhibitor, a Potential Regulator of Vascular Inflammation", The Journal of Biological Chemistry, vol. 278, No. 51, pp. 51059-51067 (2003).

Nesheim, M. et al., "Thrombin, Thrombomodulin and TAFI in the Molecular link between Coagulation and Fibrinolysis", Thrombosis and Haemostasis, vol. 78, No. 1, pp. 386-391 (1997).

Olszanski. R. et al., "Diving up to 60 m depth followed by decompression has no effect on pro-enzyme and total thrombin activatable fibrinolysis inhibitor antigen concentration", Blood Coagul Fibrinolysis, vol. 14, pp. 659-661 (2003).

Pascual, R. et al., "Purification and properties of five different forms of human procarboxypeptidase", Eur. J. Biochem. vol. 179, pp. 609-616 (1989).

Pearson, W. "Rapid and Sensitive Sequence Comparison with FASTP and FASTA", Methods in Enzymology, vol. 183, pp. 63-98 (1990).

Pereira, P. et al., "Human Procarboxypeptidase B: Three-dimensional Structure and Implications for Thrombin-activatable Fibrinolysis Inhibitor (TAFI)", J. Mol. Biol. vol. 321, pp. 537-547 (2002).

Ravindranath MD, T. et al., "Tissue Factor Pathway Inhibitor and Thrombin Activatable Fibrinolytic Inhibitor Plasma Levels following Burn and Septic Injuries in Rats", Clin. Appl Thrombosis/Hemostasis, vol. 10, No. 4, pp. 379-385 (2004).

Rees, D.C. et al., "Refined Crystal Structure of Carboxypeptidase A at 1-54 A Resolution", J. Mol. Biol., vol. 168, pp. 367-387 (1983).

Renatus, M. et al., "Structural and Functional Analyses of Benzamidine-Based Inhibitors in Complex with Trypsin: Implications for the Inhibition of Factor Xa, tPA, and Urokinase", J. Med. Chem., vol. 41, pp. 5445-5456 (1998).

Sali, A. et al., "Evaluation of Comparative Protein Modeling by Modeller", Proteins: Structure, Function, and Genetics, vol. 23, pp. 318-326 (1995).

Schatteman. K. et al., "Activation of Plasma Procarboxypeptidase U in Different Mammalian Species Points to a Conserved Pathway of Inhibition of Fibrinolysis", Thromb Haemost, vol. 82, pp. 1718-1721 (1999).

Schatteman. K. et al., "Assay of Procarboxypeptidase U, a Novel Determinant of the Fibrinolytic Cascade, in Human Plasma", Clinical Chemistry, vol. 45, No. 6, pp. 807-813 (1999).

Schechter, I. et al., "On the size of the active site in Proteases I Papain", Biochemical and Biophysical Research Communications, vol. 27, No. 2, pp. 157-162 (1967).

Schlingmann, K. et al., "Novel TRPM6 Mutations in 21 Families with Primary Hypomagnesemia and Secondary Hypocalcemia", J Am Soc Nephrol, vol. 16 pp. 1-9 (2005).

Schneider, M. et al., "Amino Acid Residues in the P6-P'3 Region of Thrombin-activable Fibrinolysis Inhibitor (TAFI) Do Not Determine the Thrombomodulin Dependence of TAFI Activation", The Journal of Biological Chemistry, vol. 277, No. 12, pp. 9944-9951 (2002).

Schneider, M. et al., "Activated Thrombin-activatable Fibrinolysis Inhibitor Reduces the Ability of High Molecular Weight Fibrin Degradation Products to Protect Plasmin from Antiplasmin*", The Journal of Biological Chemistry, vol. 279, No. 14, pp. 13340-13345 (2004).

Schroeder, V. et al., "Role of thrombin activatable fibrinolysis inhibitor (TAFI) in patients with acute pulmonary embolism", Journal of Thrombosis and Haemostasis, vol. 1, pp. 492-493 (2003).

Silveira, A. et al., "Plasma Procarboxypeptidase U in Men with Symptomatic Coronary Artery Disease", Thromb Haemost, vol. 84, pp. 364-368 (2000).

Tsai, S.P. et al., "The Gene Encoding Human Plasma Carboxypeptidase B (*CPB2*) Resides on Chromosome 13" Genomics, vol. 14, pp. 549-550 (1992).

Valnickova, Z, et al., "Activated Human Plasma Carboxypeptidase B is Retained in the Blood by Binding to $\alpha_2$- Macroglobulin and Pregnancy Zone Protein", The Journal of Biological Chemistry, vol. 271, No. 22, pp. 12937-12943 (1996).

Vanhoof, G. et al., "The Gene for Human Carboxypeptidase U (CPU)-A Proposed Novel Regulator of Plasminogen Activation-Maps to 13q14.11", Genomics, vol. 38. pp. 454-455 (1996).

Van Tilburg, N. et al., "Thrombin activatable fibrinolysis inhibitor and the risk for deep vein thrombosis", Blood, vol. 95, pp. 2855-2859 (2000).

Vaughan, T, et al., "Human Antibodies with Sub-nanomolar Affinities Isolated from a Large Non-immunized Phage Display Library", Nature Biotechnology, vol. 14, pp. 309-314 (1996).

Walker, J. et al., "The Intrisic Threshold of the Fibrinolytic System is Modulated by Basic Carboxypeptidases, but the Magnitude of the Antifibrinolytic Effect of Activated Thrombin-activable Fibrinolysis Inhibitor is Masked by Its Instability*" The Journal of Biological Chemistry, vol. 279, No. 27, pp. 27896-27904 (2004).

Walker, J. et al., "Stabilization *Versus* Inhibition of TAFIa by Competitive Inhibitors *in Vitro*\*", The Journal of Biological Chemistry, vol. 278, No. 11, pp. 8913-8921 (2003).

Watanabe, T. et al., "Changes in Activity of Plasma Thrombin Activatable Fibrinolysis Inhibitor in Pregnancy", Gynecol Obstet Invest vol. 58, pp. 19-21 (2004).

Wu, C. et al., "Activated thrombin-activatable fibrinolysis inhibitor attenuates spontaneous fibrinolysis of batroxobin-induced fibrin deposition in rat lungs", Thromb Haemost, vol. 90, pp. 414-421 (2003).

Yano, Y. et al., "Increased Plasma Thrombin-Activatable Fibrinolysis Inhibitor Levels in Normotensive Type 2 Diabetic Patients with Microalbuminuria", The Journal of Clinical Endocrinology & Metabolism, vol. 88, No. 2, pp. 736-741 (2003).

Yokota MD, I. et al., "Association Between Vitamin D Receptor Genotype and Age of Onset in Juvenile Japanese Patients with Type 1 Diabetes", BMC Med Genet, vol. 2. No. 7, pp. 1244 (2001).

Zhao, L. et al., "Identification and Characterization of Two Thrombin-activatable Fibrinolysis Inhibitor Isoforms", Thromb Haemost, vol. 80, pp. 949-955 (1998).

Zhao, L. et al., "Mutations in the Substrate Binding Site of Thrombin-activatable Fibrinolysis Inhibitor (TAFI) Alter its Substrate Specificity*", The Journal of Biological Chemistry, vol. 278, No. 34, pp. 32359-32366 (2003).

Zidane, M. et al., "Frequency of the TAFI-438 G/A and factor XIIIA Val34Leu polymorphisms in patients with objectively proven pulmonary embolism", Thromb Haemost, vol. 90, pp. 439-445 (2003).

Zirlik, A., "TAFI: a promising drug target?", Thromb Haemost, vol. 91, pp. 420-422 (2004).

NCBI Entrez Accession No. 1KWMA (gi:21465928), Barbosa, P. et al., Jan. 30, 2002.

NCBI Entrez Accession No. 6CPA (gi:231202), Rees, D.C. et al., Oct. 7, 1998.

NCBI Entrez Accession No. AF164524 (gi:7416966) Marx, P. F. et al., Apr. 5, 2000.

NCBI Entrez Accession No. M75106 (gi:189686) Eaton, D.L. et al., Jan. 7, 1995.

NCBI Entrez Accession No. NM_001872 (gi:16915931) Donmez, A. et al., Aug. 17, 2005.

NCBI Entrez Accession No. NP_001863 (gi:4503005) Donmez, A. et al., Aug. 17, 2005.

NCBI Entrez Accession No. NP_446069 (gi:16758414) Wu, C. et al., Jun. 7, 2005.

NCBI Entrez Accession No. AAF62385 (gi:7416967) Marx, P.F. et al., Apr. 5, 2000.

\* cited by examiner

FIG. 1A

```
  1  ATGAAGCTTTGCAGTCTTGCAGTCCTTGTACCCATTGTTCTCTTCTGTGAGCAGCATGTC   60
  1  M   K   L   C   S   L   A   V   L   V   P   I   V   L   F   C   E   Q   H   V    20

61  TTCGCGTTTCAGAGTGGCCAGGTTCTAGCTGCTCTTCCTAGAACCTCTAGGCAAGTTCAA  120
 21  F   A   F   Q   S   G   Q   V   L   A   A   L   P   R   T   S   R   Q   V   Q    40

121  GTGCTACAGAATCTTACTACAACATATGAGATTGTTCTCTGGCAGCCGGTAACAGCGGAC  180
 41  V   L   Q   N   L   T   T   T   Y   E   I   V   L   W   Q   P   V   T   A   D    60

181  CTTATTGAGAAGAAAAAACAAGTCCATTTTTTTGTAAATTCATCTGATGTCGACAATGTG  240
 61  L   I   E   K   K   K   Q   V   H   F   F   V   N   S   S   D   V   D   N   V    80

241  AAAGCCCATTTAAATGTGAGCGGAATTCCATGCAGTGTCCTGCTGGCAGATGTGGAAGAT  300
 81  K   A   H   L   N   V   S   G   I   P   C   S   V   L   L   A   D   V   E   D   100

301  CTTATTCAACAGCAGATTTCCAACGACACAGTCAGCCCCCGAGCCTCCGCATCGTACTAT  360
101  L   I   Q   Q   Q   I   S   N   D   T   V   S   P   R   A   S   A   S   Y   Y   120

361  GAACAGTATCACTCACTAAATGAAATCTATTCTTGGATAGAACTTATAACTGAGAAGTAT  420
121  E   Q   Y   H   S   L   N   E   I   Y   S   W   I   E   L   I   T   E   K   Y   140

421  CCTGATATGCTTACAAAAATCCACATTGGATCCTCCTATGAGAAGCACCCACTTTATGTT  480
141  P   D   M   L   T   K   I   H   I   G   S   S   Y   E   K   H   P   L   Y   V   160

481  TTAAAGGTTTCTGGAAAAGAACAAACAGCCAAAAATGCCATGTGGATTGACTGTGGAATC  540
161  L   K   V   S   G   K   E   Q   T   A   K   N   A   M   W   I   D   C   G   I   180

541  CATGCCAGAGAATGGATCTCCCCTGCTTTCTGCTTGTGGTTCATAGGCCATATAACTGAA  600
181  H   A   R   E   W   I   S   P   A   F   C   L   W   F   I   G   H   I   T   E   200

601  TACTACGGGATAATAGGGGAATATACCAATCTTCTGAGGCATGTGGATTTCTATGTTATG  660
201  Y   Y   G   I   I   G   E   Y   T   N   L   L   R   H   V   D   F   Y   V   M   220

661  CCAGTGGTTAATGTGGATGGTTATGACTACTCATGGAAAAAGAATCGAATGTGGAGAAAG  720
221  P   V   V   N   V   D   G   Y   D   Y   S   W   K   K   N   R   M   W   R   K   240

721  AACCGTTCTTTCTATGCGAACAATCGTTGCATCGGAACAGACCTGAACAGGAACTTTGCG  780
241  N   R   S   F   Y   A   N   N   R   C   I   G   T   D   L   N   R   N   F   A   260

781  TCCAAACACTGGTGTGAGGAAGGTGCATCCAGTTTCTCATGCTCGGAAACCTACTGTGCA  840
261  S   K   H   W   C   E   E   G   A   S   S   F   S   C   S   E   T   Y   C   G   280
```

FIG. 1B

```
 841  CTTTATCCTGAGTCAGAACCAGAAGCGAAGGCGGTGGCTAATTTCTTGAGAAGAAATATC   900
 281   L   Y   P   E   S   E   P   E   A   K   A   V   A   N   F   L   R   R   N   I    300

901  AACCACATTAAAGCATACATCAGCATGCATTCATACTCCCAGCATATCGTGTTTCCATAT   960
 301   N   H   I   K   A   Y   I   S   M   H   S   Y   S   Q   H   I   V   F   P   Y    320

961  TCCTATACTCGAAGCAAAAGCAAAGACCACGAGGAATTGTCTCTAGTAGCCAGTGAAGCA  1020
 321   S   Y   T   R   S   K   S   K   D   H   E   E   L   S   L   V   A   S   E   A    340

1021  GTTCGTGCTATTCAGAAAACCAGTAAAAATATCAGGTATACACATGGCCGTGGCTCACAA  1080
 341   V   R   A   I   Q   K   T   S   K   N   I   R   Y   T   H   G   R   G   S   E    360

1081  ACCTTATACCTAGCTCCTGGAGGTGCGGACGATTGGATCTATGATTTGGGCATCAAATAT  1140
 361   T   L   Y   L   A   P   G   G   A   D   D   W   I   Y   D   L   G   I   K   Y    380

1141  TCGTTTACAATTGAACTTCGAGATACGGGCAAATACGGATTCTTGCTGCCTGAGCGTTAC  1200
 381   S   F   T   I   E   L   R   D   T   G   K   Y   G   F   L   L   P   E   R   Y    400

1201  ATCAAACCCACTTGTAAAGACGCTTTTGCCGCTGTCTCTAAAATAGCTTGGCATGTCATT  1260
 401   I   K   P   T   C   K   D   A   F   A   A   V   S   K   I   A   W   H   V   I    420

1261  AGGAATGTTTAA  1272
 421   R   N   V     423
```

FIG. 2A

```
                         1                                                          50
babboon_TAFI    (1)   MKLCSLAVLVPIVLFCEQHVFAFQSGQVLALPRTSRQVQLLQNLTTTYE
human_tafi      (1)   MKLCSLAVLVPIVLFCEQHVFAFQSGQVLALPRTSRQVQLLQNLTTTYE
mouse_tafi      (1)   MKIHGIGIVAIILY-EQHGFAFQSGQVLSLPRTSRQVQLLQNLTTTYE
rat_tafi        (1)   MKILYGLGVIVAIILY-EKHGLAFQSGHVLSALPRTSRQVQLLQNLTTTYE 51                                                         100
babboon_TAFI   (51)   IVLWQPVTADLIEKKKQVHFFVNSSDVDNVKAHLNVSGIPCSVLLADVED
human_tafi     (51)   IVLWQPVTADLIVKKKQVHFFVNASDVDNVKAHLNVSGIPCSVLLADVED
mouse_tafi     (50)   VVLWQPVTAEFIEKKKEVHFFVNASDVDSVKAHLNVSRIPFNVLMNVED
rat_tafi       (50)   VVLWQPVTAEFIEKKKEVHFFVNASDVNSVKAYLNASRIPFNVLMNVED 101                                                         150
babboon_TAFI  (101)   LIQQQISNDTVSPRASASYYEQYHSLNEIYSWIELITEKYPDMLTKIHHG
human_tafi    (101)   LIQQQISNDTVSPRASASYYEQYHSLNEIYSWIEFITERHPDMLTKIHIG
mouse_tafi    (100)   LIEQQTFNDTVSPRASASYYEQYHSLNEIYSWIEVITEQHPDMLQKIYIG
rat_tafi      (100)   LIQQQTSNDTVSPRASSSYYEQYHSLNEIYSWIEVITEQHPDMLQKIYIG
```

FIG. 2B

```
                    151                                             200
babboon_TAFI (151)  SSYEKHPLYVLKVSGKEQTAKNAMWIDCGIHAREWISPAFCLWFIGHTE
  human_tafi (151)  SSFEKYPLYVLKVSGKEQTAKNAIWIDCGIHAREWISPAFCLWFIGHTQ
  mouse_tafi (150)  SSFEKYPLYVLKVSGKEQRIKNAIWIDCGIHAREWISPAFCLWFIGYVTQ
    rat_tafi (150)  SSYEKYPLYVLKVSGKEHRVKNAIWIDCGIHAREWISPAFCLWFIGYVTQ 201                                             250
babboon_TAFI (201)  YYGIIGEYTNLLRHVDFYVMPVVNVDGYDYSWKKNRMWRKNRSFYANNRC
  human_tafi (201)  FYGIIGQYTNLLRLVDFYVMPVVNVDGYDYSWKKNRMWRKNRSFYANNHC
  mouse_tafi (200)  FHGKENLYTRLLRHVDFYIMPVMNVDGYDYTWKKNRMWRKNRSAHKNNRC
    rat_tafi (200)  FHGKENTYTLLLRHVDFYIMPVMNVDGYDYTWKKNRMWRKNRSVHMNNRC 251                                             300
babboon_TAFI (251)  IGTDLNRNFASKHWCEEGASSFSCSETYCGLYPESEPEAKAVANFLRRNI
  human_tafi (251)  IGTDLNRNFASKHWCEEGASSSSCSETYCGLYPESEPEVKAVASFLRRNI
  mouse_tafi (250)  VGTDLNRNFASKHWCEKGASSSSCSETYCGLYPESEPEVKAVADFLRRNI
    rat_tafi (250)  VGTDLNRNFASKHWCEKGASSFSCSETYCGLYPESEPEVKAVADFLRRNI
```

FIG. 2C

```
                    301                                                       350
babboon_TAFI (301)  NHIKAYISMHSYSQHIVFPYSYERSKSKDHEELSLVASEAVRAIQKTSKN
human_tafi   (301)  NQIKAYISMHSYSQHIVFPYSYTRSKSKDHEELSLVASEAVRAIEKTSKN
mouse_tafi   (300)  DHIKAYISMHSYSQQILFPYSYNRSKSKDHEELSLVASEAVRAIESINKN
rat_tafi     (300)  NHIKAYISMHSYSQQILFPYSYNRSKSKDHEELSLVASEAVRAIESINKN 351                                                       400
babboon_TAFI (351)  IRYTHGRGSETLYLAPGGADDWIYDLGIKYSFTELRDTCKYGFLLPERY
human_tafi   (351)  TRYTHGHGSETLYLAPGGGDDWIYDLGIKYSFTELRDTGTYGFLLPERY
mouse_tafi   (350)  TRYTHGSGSESLYLAPGGSDDWIYDLGIKYSFTELRDTGRYGFLLPERY
rat_tafi     (350)  TRYTHGSGSESLYLAPGGSDDWIYDLGIKYSFTELRDTGRYGFLLPERF 401              423
babboon_TAFI (401)  IKPTCKDAFAAVSKIAWHVIRNV
human_tafi   (401)  IKPTCREAFAAVSKIAWHVIRNV
mouse_tafi   (400)  IKPTCAEATAAISKIVMHVIRNT
rat_tafi     (400)  IKPTCAEATAAVSKIAWHVIRNS
```

FIG. 3

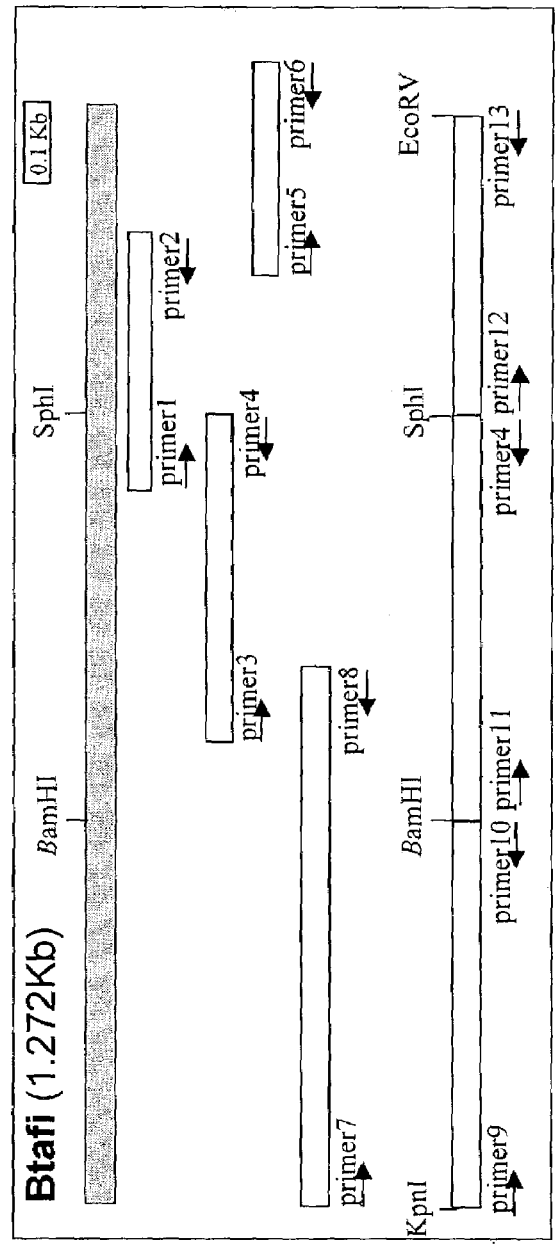

Primer 1: 5'htafi AGAACCAGAAGTGAAGGC (SEQ ID NO:3)
Primer 2: 3'mtafi GTAAACGAATATTTGATGCCCAAATC (SEQ ID NO:4)
Primer 3: 5'mtafi CCATGCCAGAGAATGGATTTCACCTGCTTTCTG (SEQ ID NO:5)
Primer 4: 3'btafi AGTATGAATGCATGCTGATGTATGCT (SEQ ID NO:6)
Primer 5: 5'btafi TCAGAAACCTTATACCTAGCTCCTGG (SEQ ID NO:7)
Primer 6: 3'htafi TTGCTGGAATCAGTAAATTAA (SEQ ID NO:8)
Primer 7: 5'htafi CTGTTGGGATGAAGCTT (SEQ ID NO:9)
Primer 8: 3'btafi TATTATCCCGTAGTATTCAGTTATA (SEQ ID NO:10)
Primer 9: 5'btafi GGTACC ATG AAGCTTTGCAGTCTTGCAG (bold: KpnI site) (SEQ ID NO:11)
Primer 10: 3'btafi CTCATAGGAGGATCCAATGTGGA (SEQ ID NO:12)
Primer 11: 5'btafi AATCCACACATTGGATCCTCCTATG (SEQ ID NO:13)
Primer 12: 5'btafi AAGCATACATCAGCATGCATTCA (SEQ ID NO:14)
Primer 13: 3'btafi GATATC *TTA* AACATTCCTAATGCATGCC (bold EcoRV site) (SEQ ID NO:15)

FIG. 4

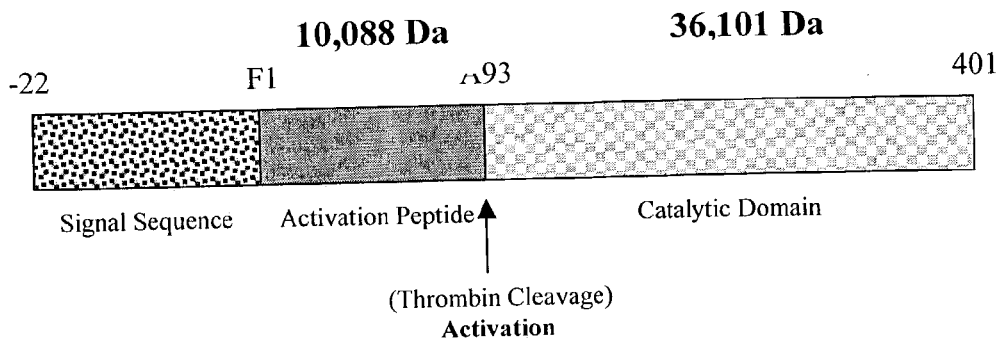

Signal Sequence  Activation Peptide  Catalytic Domain (Thrombin Cleavage)
Activation

Secreted Baboon TAFI without Signal Sequence

```
1    FQSGQVLAAL PRTSRQVQVL QNLTTTYEIV LWQPVTADLI EKKKQVHFFV
51   NSSDVDNVKA HLNVSGIPCS VLLADVEDLI QQQISNDTVS PRASASYYEQ
101  YHSLNEIYSW IELITEKYPD MLTKIHIGSS YEKHPLYVLK VSGKEQTAKN
151  AMWIDCGIHA REWISPAFCL WFIGHITEYY GIIGEYTNLL RHVDFYVMPV
201  VNVDGYDYSW KKNRMWRKNR SFYANNRCIG TDLNRNFASK HWCEEGASSF
251  SCSETYCGLY PESEPEAKAV ANFLRRNINH IKAYISMHSY SQHIVFPYSY
301  TRSKSKDHEE LSLVASEAVR AIQKTSKNIR YTHGRGSETL YLAPGGADDW
351  IYDLGIKYSF TIELRDTGKY GFLLPERYIK PTCKDAFAAV SKIAWHVIRN
401  V (residues 23 to 423 of SEQ ID NO:2)
```

Based on human TAFI (Eaton et al., JBC 266, 21833-21838, (1991))
1-92 Activation peptide
R92 ^ A93 Thrombin cleavage
N-51, N-63, N-86 Potential N-linked glycosylation sites
H-159, E-162, H-288 Zinc Binding
R-161, N-219, R-220, R-235, S-289, Y-290, Y-341, D-348, E-363 Putative substrate binding

| Analysis | Entire Protein |
|---|---|
| Length | 401 aa |
| Molecular Weight | 46170.98 m.w. |
| 1 microgram = | 21.659 pMoles |
| Molar Extinction coefficient | 92420 |
| 1 A[280] corr. to | 0.50 mg/ml |
| A[280] of 1 mg/ml | 2.00 AU |
| Isoelectric Point | 8.04 |
| Charge at pH 7 | 3.02 |

Theoretical profile based on amino acid composition without post-translational modifications

FIG. 5

```
           Signal Peptide (1-22)
        |─────────────────────||─ ─ ─ ─ ─ ─ ─ ─ ─ ─ ─ ─ ─ ─ ─
        1                                                          60
bTAFI  (1)  MKLCSLAVLVPIVLFCEQHVFAFQSGQVLAALPRTSRQVQVLQNLTTTYEIVLWQPVTAD
6CPA   (0)  ------------------------------------------------------------
1KWM_A (1)  ---------------HHGGEHFEGEKVFRVNVEDENHINIIRELASTTQIDFWKPDSVT Activation Domain (23-114)
        ─ ─ ─ ─ ─ ─ ─ ─ ─ ─ ─ ─ ─ ─ ─ ─ ─ ─ ─ ─ ─ ─ ─ ─ ─ ─ ─ ||..........
        61                                                         120
bTAFI  (61) LIEKKKQVHFFVNSSDVDNVKAHLNVSGIPCSVLLADVEDLIQQQISNDTVSPRASASYY
6CPA   (1)  ---------------------------------------------------ARSTNTFNY
1KWM_A (45) QIKPHSTVDFRVKAEDTVTVENVLKQNELQYKVLISNLRNVVEAQFDS---RVRATGHSY
                                                                :.   *

.............................................................
        121                                                        180
bTAFI (121) EQYHSLNEIYSWIELITEKYPDMLTKIHIGSSYEKHPLYVLKVSGKEQTAKNAMWIDCGI
6CPA   (10) ATYHTLDEIYDFMDLLVAQHPELVSKLQIGRSYEGRPIYVLKFS-TGGSNRPAIWIDLGI
1KWM_A (102) EKYNKWETIEAWTQQVATENPALISRSVIGTTFEGRAIYLLKVG-KAGQNKPAIFMDCGF
             *:.   :  *   : :.  : *  ::::  ** ::*  :..:*:**..  . :  *:::* *:

.............................................................
        181                                                        240
bTAFI (181) HAREWISPAFCLWFIGHITEYYGIIGEYTNLLRHVDFYVMPVVNVDGYDYSWKKNRMWRK
6CPA   (69) HSREWITQATGVWFAKKFTENYGQNPSFTAILDSMDIFLEIVTNPNGFAFTHSENRLWRK
1KWM_A (161) HAREWISPAFCQWFVREAVRTYGREIQVTELLNKLDFYVLPVLNIDGYIYTWTKSRFWRK
             *.****:  *    **   .   **    . *  *   : *::: *  *  :*  :: .:.*.***

Catalytic Domain (115-423)
        .............................................................
        241                                                        300
bTAFI (241) NRSFYANNRCIGTDLNRNFASKHWCEEGASSFSCSETYCGLYPESEPEAKAVANFLRRNI
6CPA  (129) TRSVTSSSLCVGVDANRNWDAG-FGKAGASSSPCSETYHGKYANSEVEVKSIVDFVK-NH
1KWM_A (221) TRSTHTGSSCIGTDPNRNFDAG-WCEIGASRNPCDETYCGPAAESEKETKALADFIRNKL
             .**   :..   *:*.*  ***:     :  :   ***  .*.***  *   .:**  *.*:::.:*::  :

.............................................................
        301                                                        360
bTAFI (301) NHIKAYISMHSYSQHIVFPYSYTRSKSKDHEELSLVASEAVRAIQKTSKNIRYTHGRGSE
6CPA  (187) GNFKAFLSIHSYSQLLLYPYGYTTQSIPDKTELNQVAKSAVAAL-KSLYGTSYKYGSIIT
1KWM_A (280) SSIKAYLTIHSYSQMMIYPYSYAYKLGENNAELNALAKATVKEL-ASLHGTKYTYGPGAT
             .  :**:::::*****  :::**.*:  .    :: **. :*.  :*    :   .   *.:*

.............................................................
        361                                                        420
bTAFI (361) TLYLAPGGADDWIYDLGIKYSFTIELRDTGKYGFLLPERYIKPTCKDAFAAVSKIAWHVI
6CPA  (246) TIYQASGGSIDWSYNQGIKYSFTFELRDTGRYGFLLPASQIIPTAQETWLGVLTIMEHTV
1KWM_A (339) TIYPAAGGSDDWAYDQGIRYSFTFELRDTGRYGFLLPESQIRATCEETFLAIKYVASYVL
             *:*  *.**: ** *: ** :*:****:******:******   *   .*.:::::  .: : :.:

....|
                  421
bTAFI (421) RNV-
6CPA  (306) NN--
1KWM_A (399) EHLY
              .:
```

FIG. 8

```
TAFI_BABOON    MKLCSLAVLVPIVLFCEQHVFAFQSGQVLAALPRTSRQVQVLQNLTTTYEIVLWQPVTAD
TAFI_HUMAN     MKLCSLAVLVPIVLFCEQHVFAFQSGQVLAALPRTSRQVQVLQNLTTTYEIVLWQPVTAD
               ************************************************************

TAFI_BABOON    LIEKKKQVHFFVNSSDVDNVKAHLNVSGIPCSVLLADVEDLIQQQISNDTVSPRASASYY
TAFI_HUMAN     LIVKKKQVHFFVNASDVDNVKAHLNVSGIPCSVLLADVEDLIQQQISNDTVSPRASASYY
               ** *********:***********************************************

TAFI_BABOON    EQYHSLNEIYSWIELITEKYPDMLTKIHIGSSYEKHPLYVLKVSGKEQTAKNAMWIDCGI
TAFI_HUMAN     EQYHSLNEIYSWIEFITERHPDMLTKIHIGSSFEKYPLYVLKVSGKEQTAKNAIWIDCGI
               **************:***::************:**:*****************:*****

TAFI_BABOON    HAREWISPAFCLWFIGHITEYYGIIGEYTNLLRHVDFYVMPVVNVDGYDYSWKKNRMWRK
TAFI_HUMAN     HAREWISPAFCLWFIGHITQFYGIIGQYTNLLRLVDFYVMPVVNVDGYDYSWKKNRMWRK
               *******************::****:******:***************************

TAFI_BABOON    NRSFYANNRCIGTDLNRNFASKHWCEEGASSFSCSETYCGLYPESEPEAKAVANFLRRNI
TAFI_HUMAN     NRSFYANNHCIGTDLNRNFASKHWCEEGASSSSCSETYCGLYPESEPEVKAVASFLRRNI
               ********:**********************:****************:****:*****

TAFI_BABOON    NHIKAYISMHSYSQHIVFPYSYTRSKSKDHEELSLVASEAVRAIQKTSKNIRYTHGRGSE
TAFI_HUMAN     NQIKAYISMHSYSQHIVFPYSYTRSKSKDHEELSLVASEAVRAIEKTSKNTRYTHGHGSE
               *:*****************************************:*****.*****:***

TAFI_BABOON    TLYLAPGGADDWIYDLGIKYSFTIELRDTGKYGFLLPERYIKPTCKDAFAAVSKIAWHVI
TAFI_HUMAN     TLYLAPGGGDDWIYDLGIKYSFTIELRDTGTYGFLLPERYIKPTCREAFAAVSKIAWHVI
               ********.*********************.*************::*************

TAFI_BABOON    RNV
TAFI_HUMAN     RNV
               ***
```

FIG. 9

```
hTAFI    MKLCSLAVLVPIVLFCEQHVFAFQSGQVLAALPRTSRQVQVLQNLTTTYEIVLWQPVTAD
6CPA_    ------------------------------------------------------------
1KWMA    ---------------HHGGEHFEGEKVFRVNVEDENHINIIRELASTTQIDFWKPDSVT hTAFI    LIVKKKQVHFFVNASDVDNVKAHLNVSGIPCSVLLADVEDLIQQQISNDTVSPRASASYY
6CPA_    ---------------------------------------------------ARSTNTFNY
1KWMA    QIKPHSTVDFRVKAEDTVTVENVLKQNELQYKVLISNLRNVVEAQFDS---RVRATGHSY
                                                            :.    * hTAFI    EQYHSLNEIYSWIEFITERHPDMLTKIHIGSSFEKYPLYVLKVSGKEQTAKNAIWIDCGI
6CPA_    ATYHTLDEIYDFMDLLVAQHPELVSKLQIGRSYEGRPIYVLKFS-TGGSNRPAIWIDLGI
1KWMA    EKYNKWETIEAWTQQVATENPALISRSVIGTTFEGRAIYLLKVG-KAGQNKPAIFMDCGF
           *:.  : *    :   : :. .:*  ::::   ** ::*  .:*:**..    : **:;* *:

hTAFI    HAREWISPAFCLWFIGHITQFYGIIGQYTNLLRLVDFYVMPVVNVDGYDYSWKKNRMWRK
6CPA_    HSREWITQATGVWFAKKFTENYGQNPSFTAILDSMDIFLEIVTNPNGFAFTHSENRLWRK
1KWMA    HAREWISPAFCQWFVREAVRTYGREIQVTELLNKLDFYVLPVLNIDGYIYTWTKSRFWRK
         *:****: *      ...    . * :*  :*:::   * * :*: ::  .:.*:*** hTAFI    NRSFYANNHCIGTDLNRNFASKHWCEEGASSSSCSETYCGLYPESEPEVKAVASFLRRNI
6CPA_    TRSVTSSSLCVGVDANRNWDAG-FGKAGASSSPCSETYHGKYANSEVEVKSIVDFVK-NH
1KWMA    TRSTHTGSSCIGTDPNRNFDAG-WCEIGASRNPCDETYCGPAAESEKETKALADFIRNKL
         .**   :..  *:*.*  ***:  :       : : ***  ..*.*** *   .:** *.*::..*:: :

hTAFI    NQIKAYISMHSYSQHIVFPYSYTRSKSKDHEELSLVASEAVRAIEKTSKNTRYTHGHGSE
6CPA_    GNFKAFLSIHSYSQLLLYPYGYTTQSIPDKTELNQVAKSAVAAL-KSLYGTSYKYGSIIT
1KWMA    SSIKAYLTIHSYSQMMIYPYSYAYKLGENNAELNALAKATVKEL-ASLHGTKYTYGPGAT
            ..:::::* :::.*:  .     :: **. :*.  :*   :    . * *..:* hTAFI    TLYLAPGGGDDWIYDLGIKYSFTIELRDTGTYGFLLPERYIKPTCREAFAAVSKIAWHVI
6CPA_    TIYQASGGSIDWSYNQGIKYSFTFELRDTGRYGFLLPASQIIPTAQETWLGVLTIMEHTV
1KWMA    TIYPAAGGSDDWAYDQGIRYSFTFELRDTGRYGFLLPESQIRATCEETFLAIKYVASYVL
         *:* *.**.  **  *; **:****:****** ******   *  .*..*::  .:   :   :.:

hTAFI    RNV-
6CPA_    NN--
1KWMA    EHLY
```

NUCLEIC ACID MOLECULES AND POLYPEPTIDES ENCODING BABOON TAFI

This application is a continuation-in-part Application of and claims benefit to provisional application U.S. Ser. No. 60/361,523 filed Mar. 4, 2002, under 35 U.S.C. 119(e). The entire teachings of the referenced application are incorporated herein by reference.

INTRODUCTION

The present invention relates to the isolation and identification of novel baboon nucleic acid molecules and proteins and polypeptides encoded by such nucleic acid molecules, or degenerate variants thereof, which proteins and polypeptides comprise novel baboon thrombin-activatable fibrinolysis inhibitors or "TAFI" enzyme molecules. Because the novel baboon TAFI proteins and polypeptides of the invention inhibit the breakdown of blood clots, they may be therapeutically useful for the treatment of blood disorders wherein clotting needs to be regulated or promoted, such as hemophilia or von Willebrand's disease or in other situations, such as trauma, wherein blood clotting or coagulation needs to be regulated or promoted.

The sequences of the invention are also useful in screening methods for the identification of compounds that modulate the expression of the baboon TAFI nucleic acids and/or the activity of the baboon TAFI proteins and polypeptides of the invention. Such agonist or antagonist compounds may be useful in the treatment of various blood clotting disorders and conditions requiring hemostatic control such as hemophilia or various thrombotic diseases such as deep venous thrombosis, coronary artery disease, stroke associated with atrial fibrillation and recurrent thrombosis following stroke or myocardial infarction.

BACKGROUND OF THE INVENTION

The control of blood flow in the body is regulated by two competing pathways or cascades: the coagulation cascade and the fibrinolytic cascade. In the coagulation cascade, which promotes blood clot formation, the thrombin enzyme cleaves fibrinogen leading to the formation of a clot comprised of insoluble fibrin mononers. In the fibrinolytic cascade, which promotes clot dissolution, plasminogen is converted to plasmin, which degrades fibrin and thus acts to eliminate fibrin clots. These two pathways are balanced in a healthy body via various promoters and inhibitors of the separate cascades. For example, tissue plasminogen activator (t-PA) is a protein enzyme that promotes the conversion of plasminogen to plasmin. Maintaining a proper balance between the fibrinolytic and coagulation cascades is important in maintaining the blood in an appropriate fluid state in the vasculature while minimizing, via appropriate blood clotting, any blood loss which may occur upon trauma to the body.

TAFI enzymes are proteins that inhibit fibrinolysis by inhibiting the conversion by t-PA of plasminogen to plasmin, thus inhibiting the formation of the plasmin protein that promotes blood clot degradation. Thus, TAFI proteins promote blood coagulation. More specifically, the TAFI protein is a 60 kD glycoprotein present in human plasma, which protein is cleaved by thrombin or a thrombin-thrombomodulin complex to its activated form, a 92 residue activation peptide bearing a catalytic domain. The TAFI protein cleaves C-terminal lysine and arginine from partially-degraded fibrin, thus preventing binding and efficient activation of plasminogen to plasmin. For a review of TAFI proteins and their activities, see Bouma et al., 2001, Thrombosis Research 101: 329–354.

The TAFI protein is also known in the art as plasma carboxypeptidase B ("PCPB"). Carboxypeptidase enzymes are known to hydrolyze carboxyl-terminal amide bonds of polypeptides. More specifically, PCPB hydrolyzes carboxyl-terminal amide bonds wherein the adjoining carboxy-terminal amino acids are Lys or Arg (Eaton et al., 1991, J. Biol. Chem. 266: 21833–21838). The DNA sequence encoding human PCPB and its deduced amino acid sequence are described in U.S. Pat. No. 5,206,161 (see also, U.S. Pat. Nos. 5,364,934, 5,474,901, and 5,593,674). Two naturally-occurring polymorphs of human PCPB are disclosed in U.S. Pat. No. 5,985,562.

In view of their function in inhibiting the fibrinolytic cascade, the baboon TAFI proteins and polypeptides of the invention are useful for treating blood disorders wherein clotting needs to be regulated or promoted, such as hemophilia. The present nucleic acids, proteins and polypeptides are also useful in screening assays for other proteins and factors that can modulate TAFI activity and hence, the fibrinolytic and/or coagulation cascades.

SUMMARY OF THE INVENTION

The present invention relates to the isolation and identification of novel TAFI nucleic acid molecules and proteins and polypeptides encoded by such nucleic acid, or degenerate variants thereof, which TAFI proteins and polypeptides are useful in inhibiting fibrinolysis. More specifically, the nucleic acid molecules of the invention include a specific novel baboon gene that encodes a TAFI protein or polypeptide involved in inhibiting the fibrinolytic cascade. The baboon TAFI may also have uses that are similar to the human TAFI ortholog. Such uses are described in U.S. Pat. No. 5,206,161; U.S. Pat. No. 5,364,934; U.S. Pat. No. 5,474,901; U.S. Pat. No. 5,593,674; which are hereby incorporated by reference in their entirety herein.

According to one embodiment of the invention, a novel baboon cDNA, termed herein "bTAFI", and the amino acid sequence of its derived expressed protein, is disclosed. The nucleic acid and amino acid sequences of bTAFI are depicted in FIGS. 1 and 2A–C, respectively.

The compositions of this invention include bTAFI nucleic acids, including recombinant DNA molecules, cloned genes or degenerate variants thereof, especially naturally occurring variants, which encode novel bTAFI gene products, and antibodies directed against such gene products or conserved variants or fragments thereof.

In particular, the compositions of the present invention include nucleic acid molecules (also referred to herein as "bTAFI nucleic acids") which comprise the following sequences: (a) nucleotide sequences of the novel baboon bTAFI gene depicted in FIGS. 1A–B and as deposited with the American Type Culture Collection (ATCC) as disclosed infra, as well as allelic variants and homologs thereof; (b) nucleotide sequences that encode the novel bTAFI gene product amino acid sequences depicted in FIGS. 1A–B; (c) nucleotide sequences that encode portions of the bTAFI gene products of the invention corresponding to functional domains and individual exons; (d) nucleotide sequences comprising the novel bTAFI gene sequences disclosed herein that encode mutants of the corresponding gene product in which all or a part of one or more of the domains is deleted or altered; (e) nucleotide sequences that encode fusion proteins comprising the bTAFI gene product, or one or more of its domains, fused to a heterologous polypeptide; (f) nucleotide sequences of or within the bTAFI gene, as well as chromosome sequences flanking those genes, that can be utilized as part of the methods of the present invention for the diagnosis or treatment of human disease; and (g) complements of the nucleotide sequences of (a) through (f) above. The nucleic acid molecules of the invention include, but are not limited to, cDNA and genomic DNA sequences of the bTAFI gene.

The present invention also encompasses gene products of the nucleic acid molecules listed above; i.e., proteins and/or polypeptides that are encoded by the above-disclosed bTAFI nucleic acid molecules and are expressed in recombinant host systems.

Antagonists and agonists of the bTAFI genes and/or gene products disclosed herein are also included in the present invention. Such antagonists and agonists will include, for example, small molecules, large molecules, and antibodies directed against the bTAFI gene products of the invention. Antagonists and agonists of the invention also include nucleotide sequences, such as antisense and ribozyme molecules, and gene or regulatory sequence replacement constructs, that can be used to inhibit or enhance expression of the disclosed bTAFI nucleic acid molecules.

The present invention further encompasses cloning vectors, including expression vectors, that contain the nucleic acid molecules of the invention and can be used to express those nucleic acid molecules in host organisms. The present invention also relates to host cells engineered to contain and/or express the nucleic acid molecules of the invention. Further, host organisms that have been transformed with these nucleic acid molecules are also encompassed in the present invention, e.g., transgenic animals, particularly transgenic non-human animals, and particularly transgenic non-human mammals.

The present invention also relates to methods and compositions for the diagnosis of human disease involving the fibrinolytic or coagulation pathways such as blood clotting disorders, e.g., hemophilia or thrombotic disease. Such methods comprise, for example, measuring expression of the TAFI gene in a patient sample, or detecting a mutation in the gene in the genome of a mammal, including a human, suspected of having such a blood disorder. Given the high degree of sequence homology between the baboon nucleic acid molecules of the invention and the human TAFI gene, the nucleic acids of this invention can also be used as diagnostic hybridization probes or as primers for diagnostic PCR analysis to identify human TAFI gene mutations, allelic variations, or regulatory defects, such as defects in the expression of the gene. Such diagnostic PCR analyses can be used to diagnose individuals with disorders associated with a particular TAFI gene mutation, allelic variation, or regulatory defect. Such diagnostic PCR analyses can also be used to identify individuals susceptible to blood clotting disorders.

Methods and compositions, including pharmaceutical compositions, for the treatment of blood clotting disorders are also included in the invention. Such methods and compositions are capable of modulating the level of TAFI gene expression and/or the level of activity of the respective gene product. Such methods include, for example, modulating the expression of the TAFI gene and/or the activity of the TAFI gene product for the treatment of a blood clotting disorder that is mediated by a defect in some other gene.

Such methods also include screening methods for the identification of compounds that modulate the expression of TAFI nucleic acids and/or the activity of TAFI proteins and polypeptides, e.g., assays that measure TAFI mRNA and/or gene product levels, and assays that measure levels of TAFI activity such as the ability of TAFI to inhibit the activation of plasminogen in the presence of t-PA and fibrinogen or the ability of TAFI to act on known substrates.

For example, cellular and non-cellular assays are known that can be used to identify compounds that interact with the TAFI gene and/or gene product, e.g., modulate the activity of the gene and/or the gene product. Such cell-based assays of the invention utilize cells, cell lines, or engineered cells or cell lines that express the gene product.

In one embodiment of the invention, such methods comprise contacting a compound to a cell that expresses the bTAFI nucleic acid sequence of the invention, measuring the level of gene expression, gene product expression, or gene product activity, and comparing this level to the level of the bTAFI gene expression, gene product expression, or gene product activity produced by the cell in the absence of the compound, such that if the level obtained in the presence of the compound differs from that obtained in its absence, a compound that modulates the expression of the bTAFI gene and/or the synthesis or activity of the gene product has been identified. The compounds identified by these methods, e.g., TAFI agonists or antagonists, include therapeutic compounds that can be used as pharmaceutical compositions to treat blood clotting disorders such as hemophilia or thrombotic disease.

The invention is also directed to an isolated nucleic acid comprising (a) a nucleic acid sequence that encodes a polypeptide having the amino acid sequence of FIGS. 1A–B (SEQ ID NO:2); or (b) the complement of the nucleic acid sequence of (a).

The invention is also directed to an isolated nucleic acid comprising a nucleic acid sequence encoding a bTAFI protein or polypeptide having an activity of a naturally-occurring bTAFI protein.

The invention is also directed to an isolated nucleic acid comprising (a) the nucleic acid sequence of FIGS. 1A–B (SEQ ID NO:2); or (b) a nucleic acid sequence having at least a 96.3% or greater identity with the nucleic acid sequence of FIGS. 1A–B (SEQ ID NO:2).

The invention is also directed to an isolated nucleic acid comprising the nucleic acid sequence of FIGS. 1A–B (SEQ ID NO:2), wherein the nucleic acid is genomic or cDNA.

The invention is also directed to an isolated nucleic acid comprising the nucleic acid sequence of FIGS. 1A–B (SEQ ID NO:2); which is RNA.

The invention is also directed to an isolated nucleic acid comprising the nucleic acid sequence of FIGS. 1A–B (SEQ ID NO:2); further comprising a label.

The invention is also directed to an isolated nucleic acid comprising the nucleic acid sequence of FIGS. 1A–B (SEQ ID NO:2).

The invention is also directed to an isolated nucleic acid wherein the nucleic acid encodes an bTAFI protein or polypeptide that is linked in frame to a nucleic acid sequence that encodes a heterologous protein, polypeptide or peptide.

The invention is also directed to a nucleic acid comprising a nucleic acid sequence encoding a deletion mutant of the nucleic acid of SEQ ID NO:1, or the complement thereof.

The invention is also directed to a nucleic acid comprising a nucleic acid sequence encoding a substitution mutant of the nucleic acid of SEQ ID NO:1, or the complement thereof.

The invention is also directed to a recombinant vector comprising a nucleic acid of SEQ ID NO:1, or a polynucleotide described herein.

The invention is also directed to a recombinant vector comprising a nucleic acid of SEQ ID NO:1, or a polynucleotide described herein, operatively associated with a regulatory nucleotide sequence containing transcriptional and translational regulatory information that controls expression of the nucleic acid in a host cell.

The invention is also directed to a delivery complex comprising an expression vector comprising a nucleic acid of SEQ ID NO:1, or a polynucleotide described herein, operatively associated with a regulatory nucleotide sequence containing transcriptional and translational regulatory information that controls expression of the nucleic acid in a host cell and a targeting means.

The invention is also directed to a method of making a bTAFI polypeptide comprising the steps of: (a) culturing a bTAFI host cell in an appropriate culture medium to produce an bTAFI polypeptide; and (b) isolating the bTAFI polypeptide.

The invention is also directed to a transgenic animal comprising a nucleic acid of SEQ ID NO:1, the complement thereof, or a polynucleotide described herein.

The invention is also directed to a substantially pure polypeptide encoded by a nucleic acid of SEQ ID NO:1, the complement thereof, or a polynucleotide described herein.

The invention is also directed to a substantially pure bTAFI polypeptide having (a) the amino acid sequence as depicted in FIGS. 1A–B (SEQ ID NO:2); or (b) at least a 94.4% or greater identity with the amino acid sequence of FIGS. 1A–B (SEQ ID NO:2).

The invention is also directed to an antibody preparation that binds specifically to an epitope of a polypeptide of the present invention.

The invention is also directed to a fusion protein comprising a polypeptide of SEQ ID NO:2, or a polypeptide of the present invention, and a second heterologous protein, polypeptide or peptide.

The invention is also directed to a pharmaceutical preparation comprising a therapeutically effective amount of the polypeptide of SEQ ID NO:2, or a polypeptide of the present invention, and a pharmaceutically acceptable carrier.

The invention is also directed to a test kit for detecting and/or quantitating a wild type or mutant TAFI nucleic acid molecule in a sample, comprising the steps of contacting the sample with a nucleic acid of SEQ ID NO:1, the complement thereof, or a polynucleotide of the present invention; and detecting and/or quantitating the label as an indication of the presence or absence and/or amount of a wild type or mutant TAFI nucleic acid.

The invention is also directed to a test kit for detecting and/or quantitating a wild type or mutant TAFI polypeptide in a sample, comprising the steps of contacting the sample with an antibody of the present invention; and detecting and/or quantitating a polypeptide-antibody complex as an indication of the presence or absence and/or amount of a wild type or mutant bTAFI nucleic acid.

The invention is also directed to a method for identifying compounds that modulate TAFI activity comprising: (a) contacting a test compound to a cell that expresses a nucleic acid of SEQ ID NO:2, the complement thereof, or a polynucleotide of the present invention; (b) measuring the level of bTAFI gene expression in the cell; and (c) comparing the level obtained in (b) with the bTAFI gene expression obtained in the absence of the compound; such that if the level obtained in (b) differs from that obtained in the absence of the compound, a compound that modulates bTAFI activity is identified.

The invention is also directed to a method for identifying compounds that regulate blood clotting disorders, comprising: (a) contacting a test compound to a cell that expresses a nucleic acid of SEQ ID NO:2, the complement thereof, or a polynucleotide of the present invention and (b) determining whether the test compound modulates bTAFI activity.

The invention is also directed to a method for identifying compounds that regulate blood clotting disorders comprising: (a) contacting a test compound to a nucleic acid of SEQ ID NO:2, the complement thereof, or a polynucleotide of the present invention; and (b) determining whether the test compound interacts with the nucleic acid of claim SEQ ID NO:2, the complement thereof, or a polynucleotide of the present invention.

The invention is also directed to a method for identifying compounds that regulate blood clotting disorders, comprising: (a) contacting a test compound with a cell or cell lysate containing a reporter gene operatively associated with a bTAFI regulatory element; and (b) detecting expression of the reporter gene product.

The invention is also directed to a method for identifying compounds that regulate blood clotting disorders comprising: (a) contacting a test compound with a cell or cell lysate containing bTAFI transcripts; and (b) detecting the translation of the bTAFI transcript.

The invention is also directed to a method for modulating blood clotting disorders in a subject, comprising administering to the subject a therapeutically effective amount of a bTAFI polypeptide of SEQ ID NO:2, or a polypeptide of the present invention.

The invention is also directed to a method for modulating blood clotting disorders in a subject, comprising administering to the subject a therapeutically effective amount of a bTAFI polypeptide of SEQ ID NO:2, or a polypeptide of the present invention, wherein the subject is a human.

The invention is also directed to a method of gene therapy, comprising administering to a subject an effective amount of a delivery complex of the present invention.

The invention is also directed to a method for the treatment of blood clotting disorders, comprising modulating the activity of a bTAFI polypeptide.

The invention is also directed to a method for the treatment of blood clotting disorders, comprising modulating the activity of a bTAFI polypeptide, wherein the method comprises administering an effective amount of a compound that agonizes or antagonizes the activity of a bTAFI polypeptide.

The invention is also directed to a method for the treatment of blood clotting disorders, comprising administering an effective amount of a compound that decreases expression of a bTAFI gene.

The invention is also directed to a method for the treatment of blood clotting disorders, comprising administering an effective amount of a compound that decreases expression of a bTAFI gene, wherein the compound is an oligonucleotide encoding an antisense or ribozyme molecule that targets bTAFI transcripts and inhibits translation.

The invention is also directed to a method for the treatment of blood clotting disorders, comprising administering an effective amount of a compound that increases expression of a bTAFI gene.

The invention is also directed to a pharmaceutical formulation for the treatment of blood clotting disorders, comprising a compound that activates or inhibits bTAFI activity, mixed with a pharmaceutically acceptable carrier.

The invention also provides a computer for producing a three-dimensional representation of a molecule or molecular complex, wherein said molecule or molecular complex comprises the structural coorrdinates of the model bTAFI in accordance with Table I, or a three-dimensional representation of a homologue of said molecule or molecular complex, wherein said homologue comprises backbone atoms that have a root mean square deviation from the backbone atoms of not more than about 0.25, or 0.1 Angstroms, wherein said computer comprises: A machine-readable data storage medium, comprising a data storage material encoded with machine readable data, wherein the data is defined by the set of structure coordinates of the model bTAFI according to Table I, or a homologue of said model, wherein said homologue comprises backbone atoms that have a root mean square deviation from the backbone atoms of not more than about 0.25, or 0.1 Angstroms; a working memory for storing instructions for processing said machine-readable data; a central-processing unit coupled to said working memory and to said machine-readable data storage medium for processing said machine readable data into said three-dimensional representation; and a display coupled to said central-processing unit for displaying said three-dimensional representation.

The invention also provides a machine readable storage medium which comprises the structure coordinates of bTAFI, including all or any parts conserved thrombin-activatable fibrinolysis inhibitors regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the bTAFI polypeptide. Such compounds are potential inhibitors of bTAFI or its homologues.

The invention also provides a machine-readable data storage medium, comprising a data storage material encoded with machine readable data, wherein the data is defined by the structure coordinates of the model bTAFI according to Table I or a homologue of said model, wherein said homologue comprises any kind of surrogate atoms that have a root mean square deviation from the backbone atoms of the complex of not more than about 0.25, 0.1, or less Angstroms.

The invention also provides a machine-readable data storage medium, comprising a data storage material encoded with machine readable data, wherein the data is defined by the structure coordinates of the model bTAFI according to Table I or a homologue of said model, wherein said homologue comprises any kind of surrogate atoms that have a root mean square deviation from the backbone atoms of the complex of not more than about 0.25, 0.1, or less Angstroms.

The invention also provides a model comprising all or any part of the model defined by structure coordinates of bTAFI according to Table I, or a mutant or homologue of said molecule or molecular complex.

The invention also provides a method for identifying a mutant of bTAFI with altered biological properties, function, or reactivity, the method comprising one or more of the following steps: (a) use of the model or a homologue of said model according to Table I, for the design of protein mutants with altered biological function or properties which exhibit any combination of therapeutic effects described herein; and/or (b) use of the model or a homologue of said model, for the design of a protein with mutations in the active site region comprised of the amino acids D63-P74, V109-N110, R122-N127, T139-F145, G154, E162-Y164, Y192-V203, S207, L248-D256, F268-D274, and/or G279-F280 of the catalytic domain (residue 1 of the catalytic domain corresponds to residue 115 of SEQ ID NO:2) according to Table I with altered biological function or properties which exhibit any combination of therapeutic effects described herein.

The method also relates to a method for identifying modulators of bTAFI biological properties, function, or reactivity, the method comprising the step of modeling test compounds that fit spatially into the active site region defined by all or any portion of residues D63-P74, V109-N110, R122-N127, T139-F145, G154, E162-Y164, Y192-V203, S207, L248-D256, F268-D274, and/or G279-F280 of the three-dimensional structural model according to Table I, or using a homologue or portion thereof, or analogue in which the original C, N, and O atoms have been replaced with other elements The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the bTAFI polypeptide. Such compounds are potential inhibitors of bTAFI or its homologues.

The invention also relates to a method of using said structure coordinates as set forth in Table I to identify structural and chemical features of bTAFI; employing identified structural or chemical features to design or select compounds as potential bTAFI modulators; employing the three-dimensional structural model to design or select compounds as potential bTAFI modulators; synthesizing the potential bTAFI modulators; screening the potential bTAFI modulators in an assay characterized by binding of a protein to the bTAFI. The invention also relates to said method wherein the potential bTAFI modulator is selected from a database. The invention further relates to said method wherein the potential bTAFI modulator is designed de novo. The invention further relates to a method wherein the potential bTAFI modulator is designed from a known modulator of activity.

The invention also provides a computer for producing a three-dimensional representation of a molecule or molecular complex, wherein said molecule or molecular complex comprises the structural coorrdinates of the model hTAFI in accordance with Table II, or a three-dimensional representation of a homologue of said molecule or molecular complex, wherein said homologue comprises backbone atoms that have a root mean square deviation from the backbone atoms of not more than about 0.25, or 0.1 Angstroms, wherein said computer comprises: A machine-readable data storage medium, comprising a data storage material encoded with machine readable data, wherein the data is defined by the set of structure coordinates of the model hTAFI according to Table II, or a homologue of said model, wherein said homologue comprises backbone atoms that have a root mean square deviation from the backbone atoms of not more than about 0.25, or 0.1 Angstroms; a working memory for storing instructions for processing said machine-readable data; a central-processing unit coupled to said working memory and to said machine-readable data storage medium for processing said machine readable data into said three-dimensional representation; and a display coupled to said central-processing unit for displaying said three-dimensional representation.

The invention also provides a machine readable storage medium which comprises the structure coordinates of hTAFI, including all or any parts conserved thrombin-activatable fibrinolysis inhibitors regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the hTAFI polypeptide. Such compounds are potential inhibitors of hTAFI or its homologues.

The invention also provides a machine-readable data storage medium, comprising a data storage material encoded with machine readable data, wherein the data is defined by the structure coordinates of the model hTAFI according to Table II or a homologue of said model, wherein said homologue comprises any kind of surrogate atoms that have a root mean square deviation from the backbone atoms of the complex of not more than about 0.25, 0.1, or less Angstroms.

The invention also provides a machine-readable data storage medium, comprising a data storage material encoded with machine readable data, wherein the data is defined by the structure coordinates of the model hTAFI according to Table II or a homologue of said model, wherein said homologue comprises any kind of surrogate atoms that have a root mean square deviation from the backbone atoms of the complex of not more than about 0.25, 0.1, or less Angstroms The invention also provides a model comprising all or any part of the model defined by structure coordinates of hTAFI according to Table II, or a mutant or homologue of said molecule or molecular complex.

The invention also provides a method for identifying a mutant of hTAFI with altered biological properties, function, or reactivity, the method comprising one or more of the following steps: (a) use of the model or a homologue of said model according to Table II, for the design of protein mutants with altered biological function or properties which exhibit any combination of therapeutic effects described herein; and/or (b) use of the model or a homologue of said model, for the design of a protein with mutations in the active site region comprised of the amino acids D63-P74, V109-N110, R122-N127, T139-F145, G154, E162-Y164, Y192-V203, S207, L248-D256, F268-D274, and/or G279-F280 of the catalytic domain (residue 1 of the catalytic domain corresponds to residue 115 of SEQ ID NO:17) according to Table II with altered biological function or properties which exhibit any combination of therapeutic effects described herein.

The method also relates to a method for identifying modulators of hTAFI biological properties, function, or reactivity, the method comprising the step of modeling test compounds that fit spatially into the active site region defined by all or any portion of residues D63-P74, V109-N110, R122-N127, T139-F145, G154, E162-Y164, Y192-V203, S207, L248-D256, F268-D274, and/or G279-F280 of the three-dimensional structural model according to Table II, or using a homologue or portion thereof, or analogue in which the original C, N, and O atoms have been replaced with other elements The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the hTAFI polypeptide. Such compounds are potential inhibitors of hTAFI or its homologues.

The invention also relates to a method of using said structure coordinates as set forth in Table II to identify structural and chemical features of hTAFI; employing identified structural or chemical features to design or select compounds as potential hTAFI modulators; employing the three-dimensional structural model to design or select compounds as potential hTAFI modulators; synthesizing the potential hTAFI modulators; screening the potential hTAFI modulators in an assay characterized by binding of a protein to the hTAFI. The invention also relates to said method wherein the potential hTAFI modulator is selected from a database. The invention further relates to said method wherein the potential hTAFI modulator is designed de novo. The invention further relates to a method wherein the potential hTAFI modulator is designed from a known modulator of activity.

DESCRIPTION OF THE FIGURES

FIGS. 1A–B show the polynucleotide sequence (SEQ ID NO:1) and deduced amino acid sequence (SEQ ID NO:2) of the novel bTAFI of the present invention. The standard one-letter abbreviation for amino acids is used to illustrate the deduced amino acid sequence. The polynucleotide sequence contains a sequence of 1272 nucleotides (SEQ ID NO:1), encoding a polypeptide of 423 amino acids (SEQ ID NO:2). An analysis of the bTAFI polypeptide determined that it comprised the following features: a predicted signal peptide located from about amino acid 1 to about amino acid 22 of SEQ ID NO:2 represented by single underlining; three potential N-linked glycosylation sites located at amino acid 73, 85, and/or 108 of SEQ ID NO:2 represented in bold; three predicted zinc binding amino acids located at amino acid 181, 184, and/or 310 of SEQ ID NO:2 represented in light shading; and the following predicted substrate binding amino acids located from amino acid 183, 241, 242, 257, 311, 312, 363, 370, and/or 385 of SEQ ID NO:2 represented by dark shading. The locations of conserved cysteines are noted. Conservation of cysteines at key amino acid residues is indicative of conserved structural features, which may correlate with conservation of protein function and/or activity.

FIGS. 2A–C. Alignment of protein sequences for bTAFI with other reported TAFI protein sequences.

FIG. 3. Schematic depiction of the method used to clone the bTAFI polynucleotide sequence of the invention. The sequence of each of the depicted primers is provided. Restriction sites are denoted in bold, start codons are shown in underlining, while termination codons are shown in italics.

FIG. 4. Depiction of bTAFI sequence indicating portions of protein pre- and post-thrombin cleavage. The bTAFI protein in which the 22-amino acid signal sequence has been removed upon secretion, begins with the 92 amino acid activation peptide. Thrombin cleavage occurs between Arg-92 and Ala-93 to convert the zymogen to the active form, termed TAFIa. The illustrated amino acid numbers for bTAFI represent the conventional numbering for polypeptides comprising a signal sequence whereby the signal peptide is represented by negative numbering and the first amino acid of the mature form of the protein represented by amino acid +1.

FIG. 5. Amino acid sequence alignment between baboon TAFI (upper sequence) of the present invention, bovine carboxypeptidase A (middle sequence, PDB code 6CPA; Genbank Accession No.gi|231202; SEQ ID NO:19), and baboon procarboxypeptidase B (lower sequence, PDB code 1KWM, A chain; Genbank Accession No.gi|21465928; SEQ ID NO:20). Identical residues are denoted with an asterisk ("*"), while a colon (":") denotes similar residues. The residues of baboon TAFI shown in italics form the signaling peptide region, the underlined residues comprise the activation domain of TAFI, and the residues displayed in bold comprise the catalytic domain, or TAFIa (activatable form). The baboon TAFI homology model comprises only the catalytic domain. Sequence numbering for the baboon TAFI homology model residues begins at the first residue in the catalytic domain, Ala (residue 115 of SEQ ID NO:2).

FIG. 8. Sequence alignment between the baboon and human thrombin-activatable fibrinolysis inhibitor polypeptides (SEQ ID NO:2 and 17; respectively). Asterisks ("*") denote identical residues, while colons (":") denote similar residues. Residues shown in italics comprise the peptide signaling domain of TAFI, the underlined residues comprise the activation domain that is cleaved prior to activation of TAFI and were not included in the three dimensional homology models. Residues beginning with amino acid 115 of SEQ ID NO:2 (underlined residues) were the residues used for building the baboon TAFI homology model. Residues beginning with amino acid 115 of SEQ ID NO:2 comprise the activated domain of TAFI which includes the ligand-binding domain. Based upon the latter, the first amino acid residue in the baboon TAFI homology model represents amino acid 115 of SEQ ID NO:2.

FIG. 9. Amino acid sequence alignment between human TAFI (upper sequence; SEQ ID NO:17), bovine carboxypeptidase A (middle sequence, PDB code 6CPA; Genbank Accession No.gi|231202; SEQ ID NO:19), and baboon procarboxypeptidase B (lower sequence, PDB code 1KWM, A chain; Genbank Accession No.gi|21465928; SEQ ID NO:20). Identical residues are denoted with an asterisk ("*"), while a colon (":") denotes similar residues. The residues of human TAFI shown in italics form the signaling peptide region, the underlined residues comprise the activation domain of TAFI, and the residues displayed in bold comprise the catalytic domain, or TAFIa (activatable form). The human TAFI homology model comprises only the catalytic domain. Sequence numbering for the human TAFI homology model residues begins at the first residue in the catalytic domain, Ala (residue 115 of SEQ ID NO:17).

Figure 6:
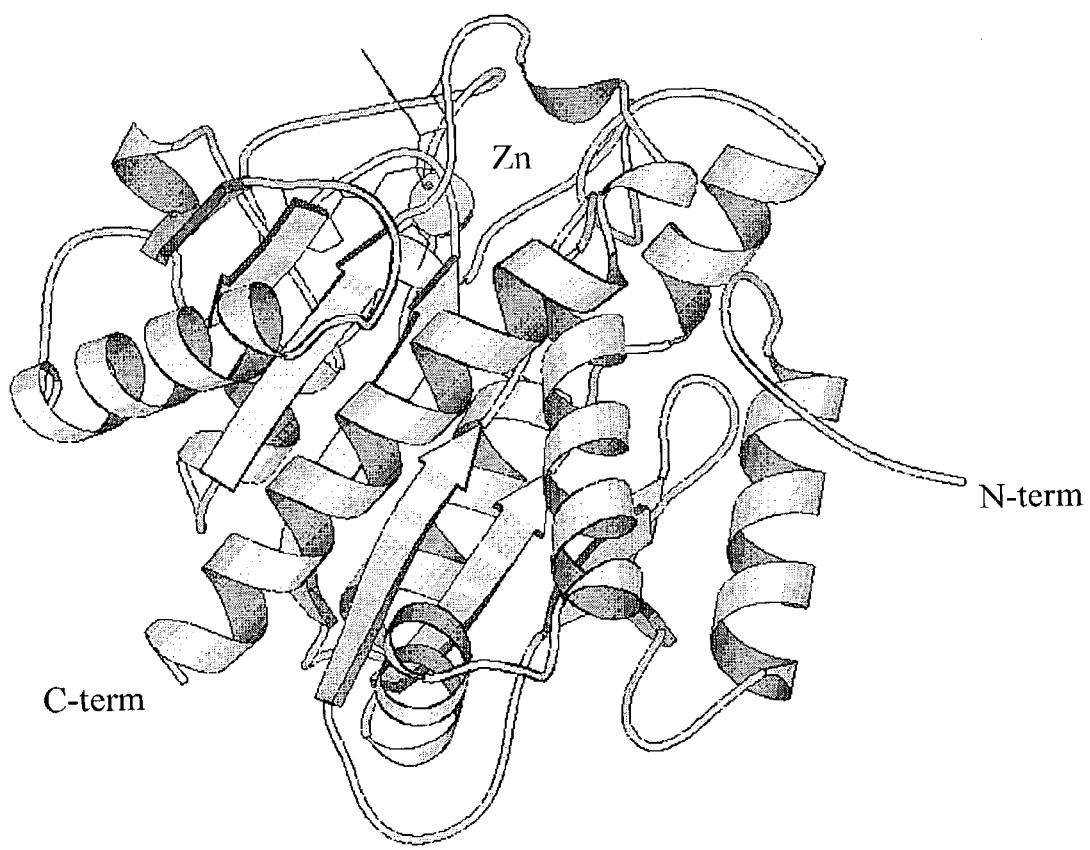
FIG. 6. Schematic representation of the homology model of the baboon TAFI polypeptide (SEQ ID NO:2) based on the sequence alignments against bovine carboxypeptidase A (PDB code 6CPA; Genbank Accession No.gi|231202; SEQ ID NO:19) and baboon procarboxypeptidase B (PDB code 1KWM; Genbank Accession No. gi|21465928; SEQ ID NO:20) shown in FIG. 5. Helices are displayed as ribbons and beta-strands are displayed as flat arrows. The zinc ion, which lies at the center of the catalytic site, is displayed as a ball and denoted as "Zn". The N and C termini are as indicated by "N-term" and "C-term", respectively. MOLSCRIPT™ was used for generating this diagram.

Table I provides the structural coordinates of the homology model of the baboon TAFI ("bTAFI") polypeptide provided in FIG. 6. A description of the headings are as follows: "Atom No" refers to the atom number within the bTAFI homology model; "Atom Name" refers to the element whose coordinates are measured, the first letter in the column defines the element; "Residue" refers to the amino acid of the bTAFI polypeptide within which the atom resides, in addition to the amino acid position in which the atom resides; "X Coord", "Y Coord", and "Z Coord" structurally define the atomic position of the element measured in three dimensions.

Figure 10:
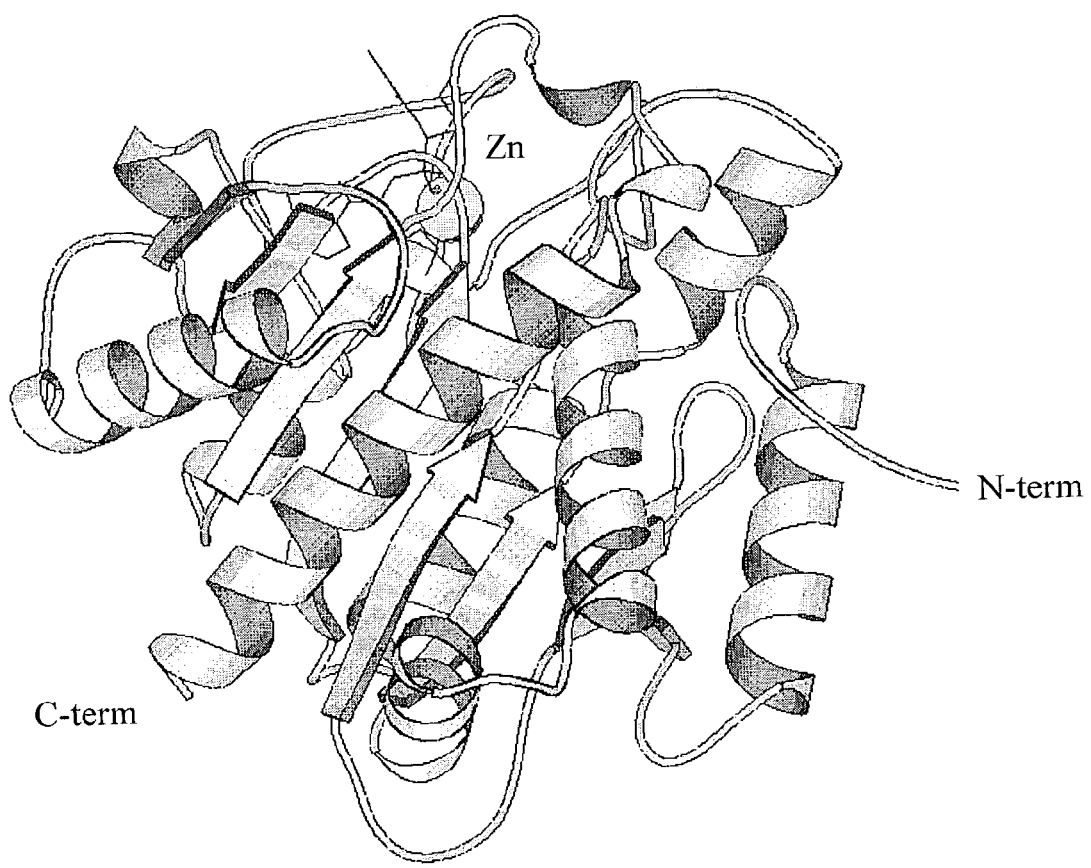
FIG. 10. Schematic representation of the homology model of the human TAFI polypeptide (SEQ ID NO:17) based on the sequence alignments against bovine carboxypeptidase A (PDB code 6CPA; Genbank Accession No.gi|231202; SEQ ID NO:19) and baboon procarboxypeptidase B (PDB code 1KWM; Genbank Accession No.; SEQ ID NO:20) shown in FIG. 9. Helices are displayed as ribbons and beta-strands are displayed as flat arrows. The zinc ion, which lies at the center of the catalytic site, is displayed as a ball and denoted as "Zn". The N and C termini are as indicated by "N-term" and "C-term", respectively. MOLSCRIPT™ was used for generating this diagram.

Table II provides the structural coordinates of the homology model of the human TAFI ("hTAFI") polypeptide provided in FIG. 10. A description of the headings are as follows: "Atom No" refers to the atom number within the hTAFI homology model; "Atom Name" refers to the element whose coordinates are measured, the first letter in the column defines the element; "Residue" refers to the amino acid of the hTAFI polypeptide within which the atom resides, in addition to the amino acid position in which the atom resides; "X Coord", "Y Coord", and "Z Coord" structurally define the atomic position of the element measured in three dimensions.

DETAILED DESCRIPTION OF THE INVENTION

The present invention relates to the isolation and identification of novel baboon nucleic acid molecules and novel proteins and polypeptides encoded by such nucleic acids, which proteins and polypeptides are novel baboon TAFI proteins and polypeptides useful in inhibiting fibrinolysis. More specifically, the invention relates to the novel baboon bTAFI nucleic acid sequence or gene depicted in FIGS. 1A–B and the corresponding bTAFI amino acid sequence or protein as depicted in FIGS. 1A–B useful for the inhibition of fibrinolysis in blood and thus useful in the treatment of blood clotting disorders.

The nucleic acid and amino acid sequences of bTAFI share significant identity to other reported PCPB nucleic acid and amino acid sequences. Specifically, the amino acid sequence of bTAFI was determined to share 94.3% identity to the reported human PCPB amino acid sequence (human tafi; Genbank Accession No. gi|4503005; SEQ ID NO:17). Moreover, the amino acid sequence of bTAFI was determined to share 81.8% identity to the reported rat PCPB amino acid sequence (rat tafi; Genbank Accession No. gi|16758414; SEQ ID NO:16), and to share 82.0% identity to the reported mouse PCPB amino acid sequence (mouse tafi; Genbank Accession No. gi|7416967; SEQ ID NO:18), as determined using the CLUSTALW algorithm with default parameters as described herein. An alignment of the bTAFI polypeptide with the other reported PCPB amino acid sequences is provided in FIGS. 2A–C.

The bTAFI nucleic acid molecules of the present invention include isolated naturally-occurring or recombinantly-produced bTAFI nucleic acid molecules, e.g., DNA molecules, cloned genes or degenerate variants thereof. The compositions of the invention also include isolated, naturally-occurring or recombinantly-produced bTAFI proteins or polypeptides or biologically active derivatives or fragments thereof.

Other embodiments of the invention include antibodies directed to the bTAFI proteins or polypeptides of the invention and methods and compositions for the diagnosis and treatment of human diseases related to blood clot dysfunction as described below.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

bTAFI Nucleic Acid Molecules of the Invention

The bTAFI gene of the invention is a novel baboon nucleic acid molecule that encodes TAFI proteins or polypeptides that act to inhibit fibrinolysis in blood. The TAFI proteins or polypeptides of the invention are therefore useful for the treatment of blood clotting disorders in which blood coagulation needs to be promoted. The TAFI nucleic acid sequences and proteins or polypeptides of the invention are also useful in screening methods for the identification of TAFI inhibitors, which compounds can have a wide therapeutic utility in treating arterial and venous thrombosis as well as the potentiation of thrombolysis.

The bTAFI nucleic acid molecules of the invention comprise the following: (a) a nucleic acid molecule containing the DNA sequence, bTAFI, as shown in FIGS. 1A–B or as contained in the cDNA clone within plasmid pFastBac1 as deposited with the ATCC on Dec. 22, 2001 and having accession number PTA 3949; (b) any nucleic acid sequence that encodes the amino acid sequence for the bTAFI protein as shown in FIGS. 1A–B; and (c) the complements of the nucleic acid sequences of (a) and (b) above.

The bTAFI polypeptide was determined to comprise a signal sequence from about amino acid 1 to about amino acid 22 of SEQ ID NO:2 (FIGS. 1A–B) according to the SPScan computer algorithm (Genetics Computer Group suite of programs). Based upon the predicted signal peptide cleavage site, the mature bTAFI polypeptide is expected to be from about amino acid 23 to about amino acid 423 of SEQ ID NO:2 (FIGS. 1A–B). As this determination was based upon the prediction from a computer algorithm, the exact physiological cleavage site may vary, as discussed more particularly herein. In this context, the term "about" should be construed to mean 1, 2, 3, 4, 5, 6, 7, 8, 9, 10, 11, 12, 13, 14, 15, 16, 17, 18, 19, or 20 more amino acids in either the N- or C-terminal direction of the above referenced polypeptide. Polynucleotides encoding these polypeptides are also provided.

In addition to the mature polypeptide above, the polynucleotides encoding the mature polypeptide are also encompassed by the present invention. Specifically, from about nucleotide position 67 to about nucleotide position 1269 of SEQ ID NO:1 (FIGS. 1A–B).

The present invention encompasses the coding sequences of the bTAFI polypeptide. Specifically, the present invention encompasses the polynucleotide corresponding to nucleotides 1 thru 1269 of SEQ ID NO:1, and the polypeptide corresponding to amino acids 1 thru 423 of SEQ ID NO:2. Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of bTAFI. Specifically, the present invention encompasses the polynucleotide corresponding to nucleotides 4 thru 1269 of SEQ ID NO:1, and the polypeptide corresponding to amino acids 2 thru 423 of SEQ ID NO:2. Also encompassed are recombinant vectors comprising said encoding sequence, and host cells comprising said vector.

The present invention encompasses a polypeptide corresponding to the activation peptide of the bTAFI polypeptide. Specifically, the present invention encompasses the polypeptide corresponding to amino acids 23 thru 114 of SEQ ID NO:2.

In addition to the activation peptide above, the polynucleotides encoding the activation peptide are also encompassed by the present invention. Specifically, from about nucleotide position 67 to about nucleotide position 342 of SEQ ID NO:1 (FIGS. 1A–B). Also encompassed are recombinant vectors comprising said encoding sequence, and host cells comprising said vector.

The present invention also encompasses a polypeptide corresponding to the catalytic domain of the bTAFI polypeptide, referred to as TAFIa upon activation. Specifically, the present invention encompasses the polypeptide corresponding to amino acids 115 thru 423 of SEQ ID NO:2.

In addition to the TAFIa polypeptide above, the polynucleotides encoding the TAFIa polypeptide are also encompassed by the present invention. Specifically, from about nucleotide position 343 to about nucleotide position 1269 of SEQ ID NO:1 (FIGS. 1A–B). Also encompassed are recombinant vectors comprising said encoding sequence, and host cells comprising said vector.

As used herein, the term "bTAFI nucleic acid molecule" may also refer to fragments and/or degenerate variants of DNA sequences (a) through (c), including naturally-occurring variants or mutant alleles thereof. Such fragments may include, for example, nucleotide sequences that encode portions of the bTAFI protein that correspond to functional domains of the protein. Also included within the bTAFI nucleic acid molecules of the invention are nucleic acid molecules, preferably DNA molecules, comprising a bTAFI nucleic acid, as described herein, operatively linked to a nucleotide sequence encoding a heterologous protein, polypeptide or peptide.

Moreover, due to the degeneracy of the genetic code, other DNA sequences that encode substantially the amino acid sequence of bTAFI may be used in the practice of the present invention for the cloning and expression of bTAFI polypeptides. In addition, altered bTAFI DNA sequences that may be used in accordance with the invention include deletions, additions or substitutions of different nucleotide residues resulting in a nucleic acid molecule that encodes the same or a functionally equivalent gene product as those described supra. The gene product itself may contain deletions, additions or substitutions of amino acid residues within the bTAFI protein sequence, which result in a silent change, thus producing a functionally equivalent bTAFI polypeptide. Such amino acid substitutions may be made on the basis of similarity in polarity, charge, solubility, hydrophobicity, hydrophilicity, and/or the amphipatic nature of the residues involved. For example, negatively-charged amino acids include aspartic acid and glutamic acid; positively-charged amino acids include lysine and arginine; amino acids with uncharged polar head groups having similar hydrophilicity values include the following: leucine, isoleucine, valine, glycine, aniline, asparagine, glutamine, serine, threonine, phenylalanine, and tyrosine. A functionally equivalent bTAFI polypeptide can include a polypeptide which displays the same type of biological activity (e.g., inhibition of fibrinolysis) as the native bTAFI protein, but not necessarily to the same extent.

The nucleic acid molecules or sequences of the invention may be engineered in order to alter the bTAFI coding sequence for a variety of ends including but not limited to alterations that modify processing and expression of the gene product. For example, mutations may be introduced using techniques well known in the art, e.g., site-directed mutagenesis, to insert new restriction sites, to alter glycosylation patterns, phosphorylation, etc. For example, in certain expression systems such as yeast, host cells may over-glycosylate the gene product. When using such expression systems, it may be preferable to alter the bTAFI coding sequence to eliminate any N-linked glycosylation sites. In another embodiment of the invention, the bTAFI nucleic acid or a modified bTAFI nucleic acid sequence may be ligated to a heterologous nucleic acid sequence to encode a fusion protein. The fusion protein may be engineered to contain a cleavage site located between the bTAFI sequence and the heterologous protein sequence, so that the bTAFI protein can be cleaved away from the heterologous moiety.

The bTAFI nucleic acid molecules of the invention can also be used as hybridization probes for obtaining bTAFI cDNAs or genomic bTAFI DNA. In addition, the bTAFI nucleic acids of the invention can be used as primers in PCR amplification methods to isolate TAFI cDNAs and genomic DNA, e.g., from other species.

The bTAFI gene sequences of the invention may also used to isolate mutant TAFI gene alleles. Such mutant alleles may be isolated from individuals either known or proposed to have a genotype related to blood clotting dysfunction. Mutant alleles and mutant allele gene products may then be utilized in the screening, therapeutic and diagnostic systems described in herein. Additionally, such bTAFI gene sequences can be used to detect TAFI gene regulatory (e.g., promoter) defects which can affect blood clotting function.

A cDNA of a mutant TAFI gene may be isolated, for example, by using PCR, a technique which is well known to those of skill in the art (see, e.g., U.S. Pat. No. 4,683,202). The first cDNA strand may be synthesized by hybridizing an oligo-dT oligonucleotide to mRNA isolated from tissue known or suspected to be expressed in an individual putatively carrying the mutant TAFI allele, and by extending the new strand with reverse transcriptase. The second strand of the cDNA is then synthesized using an oligonucleotide that hybridizes specifically to the 5' end of the normal human TAFI gene or the bTAFI gene of the present invention (which is highly homologous to the normal human gene). Using these two primers, the product is then amplified via PCR, cloned into a suitable vector, and subjected to DNA sequence analysis through methods well known in the art. By comparing the DNA sequence of the mutant TAFI allele to that of the bTAFI nucleic acid of the invention, the mutation(s) responsible for the loss or alteration of function of the mutant TAFI gene product can be ascertained.

Alternatively, a genomic library can be constructed using DNA obtained from an individual suspected of or known to carry the mutant TAFI allele, or a cDNA library can be constructed using RNA from a tissue known, or suspected, to express the mutant TAFI allele. The bTAFI nucleic acid of the invention or any suitable fragment thereof may then be labeled and used as a probe to identify the corresponding mutant TAFI allele in such libraries. Clones containing the mutant bTAFI gene sequences may then be purified and subjected to sequence analysis according to methods well known in the art.

According to another embodiment, an expression library can be constructed utilizing cDNA synthesized from, for example, RNA isolated from a tissue known, or suspected, to express a mutant TAFI allele in an individual suspected of or known to carry such a mutant allele. Gene products made by the putatively mutant tissue may be expressed and screened using standard antibody screening techniques in conjunction with antibodies raised against the bTAFI gene product of the present invention, as described in herein. For screening techniques, see, for example, Harlow, E. and Lane, eds., 1988, "Antibodies: A Laboratory Manual", Cold Spring Harbor Press, Cold Spring Harbor.

In cases where a TAFI mutation results in an expressed gene product with altered function (e.g., as a result of a missense or a frameshift mutation), a polyclonal set of anti-bTAFI gene product antibodies are likely to cross-react with the mutant TAFI gene product. Library clones detected via their reaction with such labeled antibodies can be purified and subjected to sequence analysis according to methods well known to those of skill in the art.

In an alternate embodiment of the invention, the nucleic acids of the invention, e.g., the coding sequence of bTAFI, or any appropriate fragments or derivatives thereof, can be synthesized in whole or in part, using chemical methods well known in the art, based on the nucleic acid and/or amino acid sequences of the bTAFI genes and proteins disclosed herein. See, for example, Caruthers et al., 1980, Nuc. Acids Res. Symp. Ser. 7: 215–233; Crea and Horn, 1980, Nuc. Acids Res. 9(10): 2331; Matteucci and Caruthers, 1980, Tetrahedron Letters 21: 719; and Chow and Kempe, 1981, Nuc. Acids Res. 9(12): 2807–2817. Similarly, the nucleic acids of the invention that are complements of the bTAFI gene disclosed herein and deposited in connection with this application can be obtained by chemical synthetic methods.

Alternatively, these complements can be obtained by hybridization, e.g., using the deposited bTAFI gene of this invention, under highly stringent conditions, e.g., washing in 6×SSC/0.05% sodium pyrophosphate at 37 degrees C. (for 14-base oligos), 48 degrees C. (for 17-base oligos), 55 degrees C. (for 20-base oligos), and 60 degrees C. (for 23-base oligos). These complementary nucleic acid molecules may encode or act as antisense molecules useful, for example, in TAFI gene regulation or as antisense primers in amplification reactions of TAFI nucleic acid sequences. Further, such sequences may be used as part of ribozyme and/or triple helix sequences, also useful for TAFI gene regulation. Still further, such molecules may be used as components of diagnostic methods whereby, for example, the presence of a particular TAFI allele or alternatively-spliced TAFI transcript responsible for causing or predisposing one to a disorder involving blood clotting dysfunction may be detected.

Similarly, the bTAFI proteins and polypeptides of the invention can be produced using chemical methods to synthesize the bTAFI amino acid sequence disclosed herein, in whole or in part. For example, peptides can be synthesized by solid phase techniques, cleaved from the resin, and purified by preparative high performance liquid chromatography (HPLC) (see, e.g., Creighton, 1983, Proteins Structures And Molecular Principles, W. H. Freeman and Co., N.Y., pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

The present invention encompasses polypeptide sequences which comprise, or alternatively consist of, an amino acid sequence which is at least about 80%, 85%, 90%, 91%, 92%, 93%, 94%, 94.4%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide of the present invention. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least 80%, 85%, 90%, 91%, 92%, 93%, 94%, 94.4%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, a polypeptide sequence encoded by the nucleotide sequence in SEQ ID NO:1, a polypeptide sequence encoded by the cDNA deposited as ATCC deposit no; PTA 3949, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in herein, the ORF (open reading frame), or any fragment specified as described herein.

As a practical matter, whether any particular nucleic acid molecule or polypeptide is at least 80%, 85%, 90%, 91%, 92%, 93%, 94%, 95%, 96%, 96.3%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

The invention also encompasses (a) DNA vectors that contain any of the foregoing bTAFI sequences and their complements (e.g., antisense); (b) DNA expression vectors that contain any of the foregoing bTAFI coding sequences operatively associated with a regulatory element that directs the expression of the coding sequences; and (c) genetically engineered host cells that contain any of the foregoing bTAFI coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The invention still further includes nucleic acid analogs, including but not limited to, peptide nucleic acid analogues, equivalent to the nucleic acid molecules described herein. "Equivalent" as used in this context refers to nucleic acid analogs that have the same primary base sequence as the nucleic acid molecules described above. Nucleic acid analogs and methods for the synthesis nucleic acid analogs are well known to those of skill in the art. See, e.g., Egholm, M. et al., 1993, Nature 365:566–568; and Perry-O'Keefe, H. et al., 1996, Proc. Natl. Acad. USA 93:14670–14675.

bTAFI Proteins and Polypeptides

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 91%, 92%, 93%, 94%, 94.4%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence provided as SEQ ID NO:2 or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table below.

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

The present invention also encompasses mature forms of the polypeptide comprising, or alternatively consisting of, the polypeptide sequence of SEQ ID NO:2, the polypeptide encoded by the polynucleotide described as SEQ ID NO:1, and/or the polypeptide sequence encoded by a cDNA in the deposited clone. The present invention also encompasses polynucleotides encoding mature forms of the present invention, such as, for example the polynucleotide sequence of SEQ ID NO:1, and/or the polynucleotide sequence provided in a cDNA of the deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998;6:122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1 and/or the polynucleotide sequence contained in the cDNA of a deposited clone, in a mammalian cell (e.g., COS cells, as described below). These polypeptides, and the polynucleotides encoding such polypeptides, are contemplated by the present invention.

The bTAFI nucleic acid molecules of the invention may be used to generate recombinant DNA molecules that direct the expression of bTAFI polypeptides, including the full-length bTAFI protein, functionally active or equivalent bTAFI peptides thereof, or bTAFI fusion proteins in appropriate host cells.

In order to express a biologically active bTAFI polypeptide, a nucleic acid molecule coding for the polypeptide, or a functional equivalent thereof as described in herein, is inserted into an appropriate expression vector, i.e., a vector which contains the necessary elements for the transcription and translation of the inserted coding sequence. The bTAFI gene products so produced, as well as host cells or cell lines transfected or transformed with recombinant bTAFI expression vectors, can be used for a variety of purposes. These include, but are not limited to, generating antibodies (i.e., monoclonal or polyclonal) that bind to the bTAFI protein, including those that competitively inhibit binding and thus can "neutralize" bTAFI activity, and the screening and selection of bTAFI analogs or ligands.

Methods which are well known to those skilled in the art are used to construct expression vectors containing the bTAFI coding sequences of the invention and appropriate transcriptional and translational control signals. These methods include in vitro recombinant DNA techniques, synthetic techniques and in vivo recombination/genetic recombination. See, for example, the techniques described in Maniatis et al., 1989, Molecular Cloning, A Laboratory Manual, Cold Spring Harbor Laboratory, N.Y. and Ausubel et al., 1989, Current Protocols in Molecular Biology, Greene Publishing Associates and Wiley Interscience, N.Y. See also Sambrook et al., 1989, Molecular Cloning, A Laboratory Manual, Cold Spring Harbor Press, N.Y.

A variety of host-expression vector systems may be used to express the bTAFI coding sequences of this invention. Such host-expression systems represent vehicles by which the coding sequences of interest may be produced and subsequently purified, but also represent cells which may, when transformed or transfected with the appropriate nucleotide coding sequences, exhibit the corresponding bTAFI gene products in situ and/or function in vivo. These hosts include, but are not limited to, microorganisms such as bacteria (e.g., *E. coli, B. subtilis*) transformed with recombinant bacteriophage DNA, plasmid DNA or cosmid DNA expression vectors containing bTAFI coding sequences; yeast (e.g., Saccharomyces, Pichia) transformed with recombinant yeast expression vectors containing bTAFI coding sequences; insect cell systems infected with recombinant virus expression vectors (e.g., baculovirus) containing bTAFI coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing bTAFI coding sequences; or mammalian cell systems (e.g., COS, CHO, BHK, 293, 3T3) harboring recombinant expression constructs containing promoters derived from the genome of mammalian cells (e.g., the metallothionein promoter) or from mammalian viruses (e.g., the adenovirus late promoter or vaccinia virus 7.5K promoter).

The expression elements of these systems can vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of bTAFI DNA, SV40-, BPV- and EBV-based vectors may be used with an appropriate selectable marker.

In bacterial systems, a number of expression vectors may be advantageously selected depending upon the use intended for the bTAFI expressed. For example, when large quantities of a bTAFI polypeptide are to be produced, e.g., for the generation of antibodies or the production of the bTAFI gene product, vectors which direct the expression of high levels of fusion protein products that are readily purified may be desirable. Such vectors include, but are not limited to, the *E. coli* expression vector pUR278 (Ruther et al., 1983, EMBO J. 2: 1791), in which the bTAFI coding sequence may be ligated into the vector in frame with the lacZ coding region so that a hybrid bTAFI/lacZ protein is produced; pIN vectors (Inouye & Inouye, 1985, Nucleic Acids Res. 13: 3101–3109; Van Heeke & Schuster, 1989, J. Biol. Chem. 264: 5503–5509); and the like. pGEX vectors may also be used to express foreign polypeptides as fusion proteins with glutathione S-transferase (GST). In general, such fusion proteins are soluble and can easily be purified from lysed cells by affinity chromatography, e.g., adsorption to glutathione-agarose beads followed by elution in the presence of free glutathione. The pGEX vectors are designed to include thrombin or factor Xa protease cleavage sites so that the cloned polypeptide of interest can be released from the GST moiety. See also Booth et al., 1988, Immunol. Lett. 19: 65–70; and Gardella et al., 1990, J. Biol. Chem. 265: 15854–15859; Pritchett et al., 1989, Biotechniques 7: 580.

In yeast, a number of vectors containing constitutive or inducible promoters may be used. For a review, see Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Cold Spring Harbor Press, Vols. I and II.

In an insect system, *Autographa californica* nuclear polyhidrosis virus (AcNPV) can be used as a vector to express foreign genes. The virus grows in *Spodoptera frugiperda* cells. The bTAFI coding sequence may be cloned into non-essential regions (for example, the polyhedrin gene) of the virus and placed under control of an AcNPV promoter (for example, the polyhedrin promoter). Successful insertion of the bTAFI coding sequence will result in inactivation of the polyhedrin gene and production of non-occluded recombinant virus (i.e., virus lacking the proteinaceous coat coded for by the polyhedrin gene). These recombinant viruses can then be used to infect *Spodoptera frugiperda* cells in which the inserted gene is expressed (see e.g., Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the bTAFI coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing bTAFI in infected hosts (see, e.g., Logan & Shenk, 1984, Proc. Natl. Acad. Sci.

(USA) 81: 3655–3659). Alternatively, the vaccinia 7.5K promoter may be used (see, e.g., Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931).

Specific initiation signals may also be required for efficient translation of inserted bTAFI coding sequences. These signals include the ATG initiation codon and adjacent sequences. In cases where the entire bTAFI gene, including its own initiation codon and adjacent sequences, is inserted into the appropriate expression vector, no additional translational control signals may be needed. However, in cases where only a portion of the bTAFI coding sequence is inserted, exogenous translational control signals, including the ATG initiation codon, must be provided. Furthermore, the initiation codon must be in phase with the reading frame of the bTAFI coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, WI38, etc.

For long-term, high-yield production of recombinant proteins, stable expression is preferred. For example, cell lines which stably express the bTAFI proteins or polypeptides of this invention may be engineered. Thus, rather than using expression vectors which contain viral origins of replication, host cells can be transformed with bTAFI nucleic acid molecules, e.g., DNA, controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express bTAFI proteins or polypeptides on the cell surface. Such engineered cell lines are particularly useful in screening for bTAFI analogs or ligands.

In instances where the mammalian cell is a human cell, among the expression systems by which the bTAFI nucleic acid sequences of the invention can be expressed are human artificial chromosome (HAC) systems (see, e.g., Harrington et al., 1997, Nature Genetics 15: 345–355).

bTAFI gene products can also be expressed in transgenic animals such as mice, rats, rabbits, guinea pigs, pigs, micropigs, sheep, goats, and non-human primates, e.g., baboons, monkeys, and chimpanzees. The term "transgenic" as used herein refers to animals expressing bTAFI nucleic acid sequences from a different species (e.g., mice expressing human bTAFI nucleic acid sequences), as well as animals that have been genetically engineered to overexpress endogenous (i.e., same species) bTAFI nucleic acid sequences.

Transgenic animals according to this invention may be produced using techniques well known in the art, including but not limited to, pronuclear microinjection (Hoppe, P. C. and Wagner, T. E., 1989, U.S. Pat. No. 4,873,191), retrovirus mediated gene transfer into germ lines (Van der Putten et al., 1985, Proc. Natl. Acad. Sci., USA 82: 6148–6152), gene targeting in embryonic stem cells (Thompson et al., 1989, Cell 56: 313–321), electroporation of embryos (Lo, 1983, Mol Cell. Biol. 3: 1803–1814), and sperm-mediated gene transfer (Lavitrano et al., 1989, Cell 57: 717–723), etc. For a review of such techniques, see Gordon, 1989, Transgenic Animals, Intl. Rev. Cytol. 115: 171–229.

In addition, any technique known in the art may be used to produce transgenic animal clones containing a bTAFI transgene, for example, nuclear transfer into enucleated oocytes of nuclei from cultured embryonic, fetal or adult cells induced to quiescence (Campbell et al., 1996, Nature 380: 64–66; Wilmut et al., 1997, Nature 385: 810–813).

Host cells which contain the bTAFI coding sequence and which express a biologically active gene product may be identified by at least four general approaches; (a) DNA-DNA or DNA-RNA hybridization; (b) the presence or absence of "marker" gene functions; (c) assessing the level of transcription as measured by the expression of bTAFI mRNA transcripts in the host cell; and (d) detection of the gene product as measured by immunoassay or by its biological activity.

In the first approach, the presence of the bTAFI coding sequence inserted in the expression vector can be detected by DNA-DNA or DNA-RNA hybridization using probes comprising nucleotide sequences that are homologous to the bTAFI coding sequence, respectively, or portions or derivatives thereof.

In the second approach, the recombinant expression vector/host system can be identified and selected based upon the presence or absence of certain "marker" gene functions. For example, if the bTAFI coding sequence is inserted within a marker gene sequence of the vector, recombinants containing the bTAFI coding sequence can be identified by the absence of the marker gene function. Alternatively, a marker gene can be placed in tandem with the bTAFI sequence under the control of the same or different promoter used to control the expression of the bTAFI coding sequence. Expression of the marker in response to induction or selection indicates expression of the bTAFI coding sequence.

Selectable markers include resistance to antibiotics, resistance to methotrexate, transformation phenotype, and occlusion body formation in baculovirus. In addition, thymidine kinase activity (Wigler et al., 1977, Cell 11: 223), hypoxanthine-guanine phosphoribosyltransferase (Szybalska & Szybalski, 1962, Proc. Natl. Acad. Sci. USA 48: 2026) and adenine phosphoribosyltransferase (Lowy et al., 1980, Cell 22: 817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Proc. Natl. Acad. Sci. USA 77: 3567; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin, et al., 1981, J. Mol.

Biol. 150: 1); and hygro, which confers resistance to hygromycin (Santerre et al., 1984, Gene 30: 147). Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue, 1987, in Current Communications in Molecular Biology, Cold Spring Harbor Laboratory ed.).

In the third approach, transcriptional activity for the bTAFI coding region can be assessed by hybridization assays. For example, RNA can be isolated and analyzed by Northern blot using a probe homologous to the bTAFI coding sequence or particular portions thereof. Alternatively, total nucleic acids of the host cell may be extracted and assayed for hybridization to such probes.

In the fourth approach, the expression of the bTAFI protein product can be assessed immunologically, for example by Western blots, immunoassays such as radioimmuno-precipitation, enzyme-linked immunoassays and the like. The ultimate test of the success of the expression system, however, involves the detection of biologically active bTAFI gene product. A number of assays can be used to detect bTAFI activity including, but not limited to, binding assays and biological assays for bTAFI activity.

Once a clone that produces high levels of a biologically active bTAFI polypeptide is identified, the clone may be expanded and used to produce large amounts of the polypeptide which may be purified using techniques well known in the art, including but not limited to, immunoaffinity purification using antibodies, immunoprecipitation or chromatographic methods including high performance liquid chromatography (HPLC).

Where the bTAFI coding sequence is engineered to encode a cleavable fusion protein, purification may be readily accomplished using affinity purification techniques. For example, a collagenase cleavage recognition consensus sequence may be engineered between the carboxy terminus of bTAFI and protein A. The resulting fusion protein may be readily purified using an IgG column that binds the protein A moiety. Unfused bTAFI may be readily released from the column by treatment with collagenase. Another example would be the use of pGEX vectors that express foreign polypeptides as fusion proteins with glutathionine S-transferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In fact, any cleavage site or enzyme cleavage substrate may be engineered between the bTAFI gene product sequence and a second peptide or protein that has a binding partner which could be used for purification, e.g., any antigen for which an immunoaffinity column can be prepared.

In addition, bTAFI fusion proteins may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

Alternatively, the bTAFI proteins and polypeptides of the invention can be produced using chemical methods to synthesize the bTAFI amino acid sequences in whole or in part. For example, peptides can be synthesized by solid phase techniques, cleaved from the resin, and purified by preparative high performance liquid chromatography (see, e.g., Creighton, 1983, Proteins Structures And Molecular Principles, W. H. Freeman and Co., N.Y., pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

The bTAFI proteins, polypeptides and peptide fragments, mutated, truncated or deleted forms of bTAFI and/or bTAFI fusion proteins can be prepared for various uses, including but not limited to, the generation of antibodies, as reagents in diagnostic assays, the identification of other cellular gene products involved in the blood clotting cascades, as well as reagents in assays for screening for compounds for use in the treatment of blood clotting disorders such as hemophilia, von Willebrand's disease or thrombotic diseases such as deep venous thrombosis, coronary artery disease, stroke associated with atrial fibrillation and recurrent thrombosis following stroke or myocardial infarction.

As will be appreciated by the skilled practitioner, should the amino acid fragment comprise an antigenic epitope, for example, biological function per se need not be maintained. The terms bTAFI polypeptide and bTAFI protein are used interchangeably herein to refer to the encoded product of the bTAFI nucleic acid sequence according to the present invention.

Antibodies to bTAFI Polypeptides

The present invention also includes antibodies directed to the bTAFI polypeptides of this invention and methods for the production of those antibodies, including antibodies that specifically recognize one or more bTAFI epitopes or epitopes of conserved variants or peptide fragments of bTAFI. Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

Given the high degree of homology between the human TAFI protein and the bTAFI protein of the invention (studies have indicated that the bTAFI protein of the invention cross-reacts with antibodies to the human TAFI protein), antibodies to bTAFI may be used, for example, in the detection of a TAFI protein or polypeptide in an biological sample and may, therefore, be utilized as part of a diagnostic or prognostic technique whereby patients may be tested for abnormal levels of TAFI, and/or for the presence of abnormal forms of the protein. Such antibodies may also be utilized in conjunction with, for example, compound screening protocols for the evaluation of the effect of test compounds on TAFI levels and/or activity. Additionally, such antibodies can be used in conjunction with the gene therapy techniques described in herein, for example, to evaluate normal and/or genetically-engineered bTAFI-expressing cells prior to their introduction into the patient.

For the production of antibodies against bTAFI, various host animals may be immunized by injection with the protein or a portion thereof. Such host animals include rabbits, mice, rats, and baboons. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a bTAFI polypeptide, or an antigenic functional derivative thereof. For the production of polyclonal antibodies, host animals such as those described above, may be immunized by injection with the bTAFI polypeptide supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein (1975, Nature 256: 495–497; and U.S. Pat. No. 4,376,110), the human B-cell hybridoma technique (Kosbor et al., 1983, Immunology Today 4: 72; Cole et al., 1983, Proc. Natl. Acad. Sci. USA 80: 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridomas producing the monoclonal antibodies of this invention may be cultivated in vitro or in vivo.

In addition, techniques developed for the production of chimeric antibodies (Morrison et al., 1984, Proc. Natl. Acad. Sci., 81: 6851–6855; Neuberger et al., 1984, Nature 312: 604–608; Takeda et al., 1985, Nature 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S. Pat. No. 4,816,397).

In addition, techniques have been developed for the production of humanized antibodies (see, e.g., Queen, U.S. Pat. No. 5,585,089). Humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242: 423–426; Huston et al., 1988, Proc. Natl. Acad. Sci. USA 85: 5879–5883; and Ward et al., 1989, Nature 334: 544–546) can be used in the production of single chain antibodies against bTAFI. Single chain antibodies are formed by linking the heavy and light chain fragments of the Fv region via an amino acid bridge, resulting in a single chain polypeptide.

Furthermore, antibody fragments which recognize specific epitopes of bTAFI may be produced by techniques well known in the art. For example, such fragments include but are not limited to, $F(ab')_2$ fragments which can be produced by pepsin digestion of the antibody molecule and Fab fragments which can be generated by reducing the disulfide bridges of the $F(ab')_2$ fragments. Alternatively, Fab expression libraries may be constructed (Huse et al., 1989, Science 246: 1275–1281) to allow rapid and easy identification of monoclonal Fab fragments with the desired specificity.

Uses of the bTAFI Nucleic Acid Molecules, Proteins and Polypeptides, and Antibodies of the Invention As discussed supra, the bTAFI nucleic acid molecules of this invention encode proteins that are involved in the inhibition of fibrinolysis or the dissolution of blood clots. Thus, these proteins are important in maintaining the appropriate balance between the fluidity of blood flow versus blood coagulation in the body. Given the important role of these proteins in hemostatic control in the body and the high degree of homology between the baboon nucleic acids and proteins and polypeptides of the invention and human TAFI sequences, the bTAFI nucleic acid molecules, proteins and polypeptides of this invention are useful for the diagnosis and treatment of a variety of human disease conditions that involve blood coagulation dysfunction, e.g., hemophilia, von Willebrand's disease or thrombotic diseases such as deep venous thrombosis, coronary artery disease, stroke associated with atrial fibrillation and recurrent thrombosis following stroke or myocardial infarction.

Among the uses for the nucleic acid molecules, proteins and polypeptides of the invention are the prognostic and diagnostic evaluation of human disorders involving blood clotting dysfunction, and the identification of subjects with a predisposition to such disorders, as described below. Other uses include methods for the treatment of such blood clotting disorders and for the modulation of TAFI gene-mediated activity.

In addition, the nucleic acid molecules, proteins and polypeptides of the invention can be used in assays for the identification of compounds that modulate the expression of TAFI genes and/or the activity of TAFI gene products. Such compounds can include, for example, compounds, including but not limited to, other cellular products or small molecule compounds, which are involved in the blood coagulation and/or fibrinolytic cascades.

Diagnosis and Prognosis of Blood Clotting Disorders

Methods of the invention for the diagnosis and prognosis of human diseases involving blood clotting dysfunction, such as hemophilia or thrombotic disease, may utilize reagents such as the bTAFI nucleic acid molecules and sequences described in herein, or antibodies directed against bTAFI polypeptides, including peptide fragments thereof, as described in herein, supra. Specifically, such reagents may be used, for example, for: (1) the detection of the presence of TAFI gene mutations, or the detection of either over- or under-expression of TAFI gene mRNA relative to the non-dysfunctional state or the qualitative or quantitative detection of alternatively-spliced forms of TAFI transcripts which may correlate with certain blood clotting isorders or susceptibility toward such disorders; and (2) the detection of either an over- or an under-abundance of TAFI gene product, i.e., proteins and/or polypeptides, relative to the non-dysfunctional state or the presence of a modified (e.g., less than full length) TAFI gene product which correlates with a blood coagulation dysfunctional state or a progression toward such a state.

The methods described herein may be performed, for example, by utilizing pre-packaged diagnostic test kits comprising at least one specific bTAFI gene nucleic acid or anti-bTAFI gene antibody reagent described herein, which may be conveniently used, e.g., in clinical settings, to screen and diagnose patients exhibiting blood clotting or other hemostatic abnormalities and to screen and identify those individuals exhibiting a predisposition to such abnormalities.

For the detection of TAFI mutations, any nucleated cell can be used as a starting source for genomic nucleic acid. For the detection of TAFI transcripts or TAFI gene products, any cell type or tissue in which the TAFI gene is expressed may be utilized such as liver cells.

Nucleic acid-based detection techniques are described in herein, whereas peptide-based detection techniques are described in herein.

Detection of bTAFI Gene Nucleic Acid Molecules

Mutations or polymorphisms within the TAFI gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving TAFI gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen, T. J. et al., 1991, Genomics 11:199–205; Perry, D. J. & Carrell, R. W., 1992), denaturing gradient gel electrophoresis (DGGE; Myers, R. M. et al., 1985, Nucl. Acids Res. 13:3131–3145), chemical mismatch cleavage (Cotton, R. G. et al., 1988, Proc. Natl. Acad. Sci. USA 85:4397–4401) and oligonucleotide hybridization (Wallace, R. B. et al., 1981, Nucl. Acids Res. 9:879–894; Lipshutz, R. J. et al., 1995, Biotechniques 19:442–447).

Diagnostic methods for the detection of TAFI gene specific nucleic acid molecules, in patient samples or other appropriate cell sources, may involve the amplification of specific gene sequences, e.g., by PCR, followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the TAFI gene in order to determine whether a TAFI gene mutation exists. Given the high degree of homology between the bTAFI gene of the present invention and the normal human gene, the bTAFI nucleic acids of this invention can be used as a substitute for the normal TAFI gene control in such diagnostic methods.

Further, well-known genotyping techniques can be performed to type polymorphisms that are in close proximity to mutations in the TAFI gene itself. These polymorphisms can be used to identify individuals in families likely to carry mutations. If a polymorphism exhibits linkage disequilibrium with mutations in the TAFI gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

A bTAFI probe derived from the bTAFI nucleic acid sequences of the invention can be used to directly identify RFLPs. Additionally, such bTAFI probes or primers could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of TAFI gene-specific mutations or polymorphisms can include hybridization techniques which involve, for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including the bTAFI nucleic acid molecules of the invention, including recombinant DNA molecules, cloned genes or degenerate variants thereof, as described in herein, under conditions favorable for the specific annealing of these reagents to their complementary sequences within the TAFI gene. Preferably, the lengths of these nucleic acid reagents are at least 15 to 30 nucleotides. After incubation, all non-annealed nucleic acids are removed from the nucleic acid:bTAFI molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid molecules of the invention as described in herein are easily removed. Detection of the remaining, annealed, labeled bTAFI nucleic acid reagents is accomplished using standard techniques well-known to those in the art. The TAFI gene sequences to which the bTAFI nucleic acid molecules of the invention have annealed can be compared to the annealing pattern expected from a normal TAFI gene sequence in order to determine whether a TAFI gene mutation is present.

Quantitative and qualitative aspects of TAFI gene expression can also be assayed. For example, RNA from a cell type or tissue known, or suspected, to express the TAFI gene may be isolated and tested utilizing hybridization or PCR techniques as described supra. The isolated cells can be derived from cell culture or from a patient. The analysis of cells taken from culture may be a necessary step in the assessment of cells to be used as part of a cell-based gene therapy technique or, alternatively, to test the effect of compounds on the expression of the TAFI gene. Such analyses may reveal both quantitative and qualitative aspects of the expression pattern of the TAFI gene, including activation or inactivation of TAFI gene expression and/or the presence of alternatively-spliced TAFI transcripts.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the bTAFI nucleic acid molecules of the invention as described in herein. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in TAFI transcript size which may be due to normal or abnormal alternative splicing. Additionally, such techniques can be utilized to detect quantitative differences between levels of full length and/or alternatively-spliced TAFI transcripts detected in normal individuals relative to those individuals exhibiting blood clotting dysfunction disorders or exhibiting a predisposition to toward such disorders.

In the case where detection of specific alternatively-spliced species is desired, appropriate primers and/or hybridization probes can be used, such that, in the absence of such sequence, no amplification would occur. Alternatively, primer pairs may be chosen utilizing the bTAFI sequence depicted in FIGS. 1A–B to choose primers which will yield fragments of differing size depending on whether a particular exon is present or absent from the TAFI transcript being analyzed.

As an alternative to amplification techniques, standard Northern analyses can be performed if a sufficient quantity of the appropriate cells can be obtained. Utilizing such techniques, quantitative as well as size-related differences between TAFI transcripts can also be detected.

Additionally, it is possible to perform TAFI gene expression assays in situ, i.e., directly upon tissue sections (fixed and/or frozen) of patient tissue obtained from biopsies or resections, such that no nucleic acid purification is necessary. The bTAFI nucleic acid molecules of the invention as described in herein may be used as probes and/or primers for such in situ procedures (see, for example, Nuovo, G. J., 1992, "PCR In Situ Hybridization: Protocols And Applications", Raven Press, NY).

Detection of bTAFI Gene Products

Antibodies directed against TAFI gene products or conserved variants or peptide fragments thereof, such as the bTAFI antibodies of the invention as described supra, may also be used for the diagnosis and prognosis of blood clotting-related disorders. Such diagnostic methods may be used to detect abnormalities in the level of TAFI gene expression or abnormalities in the structure and/or temporal, tissue, cellular, or subcellular location of TAFI gene products. Moreover, bTAFI antibodies, or fragments of antibodies, of the present invention may be used to screen for potentially therapeutic compounds in vitro to determine their effects on TAFI gene expression and TAFI peptide production. The compounds which have beneficial effects on blood clotting disorders can be identified and a therapeutically effective dose determined.

In addition, in vitro immunoassays may be used to assess the efficacy of cell-based gene therapy for blood-clotting disorders. For example, antibodies of the invention directed against bTAFI peptides may be used in vitro to determine the level of TAFI gene expression achieved in cells genetically engineered to produce TAFI peptides. Such analysis will allow for a determination of the number of transformed cells necessary to achieve therapeutic efficacy in vivo, as well as optimization of the gene replacement protocol.

The tissue or cell type to be analyzed will generally include those which are known, or suspected, to express the TAFI gene such as liver cells. The protein isolation methods employed may, for example, be such as those described in Harlow, E. and Lane, D., 1988, "Antibodies: A Laboratory Manual", Cold Spring Harbor Laboratory Press, Cold Spring Harbor, N.Y. The isolated cells can be derived from cell culture or from a patient. The analysis of cells taken from culture may be a necessary step in the assessment of cells to be used as part of a cell-based gene therapy technique or, alternatively, to test the effect of compounds on the expression of the TAFI gene.

Preferred diagnostic methods for the detection of TAFI gene products or conserved variants or peptide fragments thereof, may involve, for example, immunoassays wherein the TAFI gene products or conserved variants, including gene products which are the result of alternatively-spliced transcripts, or peptide fragments are detected by their interaction with an anti-bTAFI gene product-specific antibody. For example, antibodies, or fragments of antibodies, such as those described in herein, may be used to quantitatively or qualitatively detect the presence of TAFI gene products or conserved variants or peptide fragments thereof. The antibodies (or fragments thereof) may, additionally, be employed histologically, as in immunofluorescence or immunoelectron microscopy, for in situ detection of TAFI gene products or conserved variants or peptide fragments thereof. In situ detection may be accomplished by removing a histological specimen from a patient, and applying thereto a labeled bTAFI antibody of the present invention. The antibody (or fragment) is preferably applied by overlaying the labeled antibody (or fragment) onto a biological sample. Through the use of such a procedure, it is possible to determine not only the presence of the TAFI gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for TAFI gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying TAFI gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled bTAFI gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-bTAFI gene product antibody may be determined according to well known methods. Those skilled in the art will be able to determine operative and optimal assay conditions for each determination by employing routine experimentation.

One of the ways in which the bTAFI gene peptide-specific antibody can be detectably labeled is by linking the antibody to an enzyme in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments of the invention, it is possible to detect TAFI gene peptides through the use of a radioimmunoassay (RIA) (see, for example, Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently-labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Screening Assays for Compounds that Modulate TAFI Activity

Screening assays can be used to identify compounds that modulate TAFI activity. These compounds can include, but are not limited to, peptides, small organic or inorganic molecules or macromolecules such as nucleic acid molecules or proteins, and may be utilized in the regulation and control of blood clotting disorders. These compounds may also be useful, e.g., in elaborating the biological functions of TAFI gene products, i.e., proteins and polypeptides, modulating those biological functions and for ameliorating symptoms of blood clotting disorders.

The compositions of the invention include pharmaceutical compositions comprising one or more of these compounds. Such pharmaceutical compositions can be formulated as discussed in herein.

More specifically, these compounds can include compounds that bind to TAFI gene products, compounds that bind to other proteins that interact with a TAFI gene product and/or interfere with the interaction of the TAFI gene product with other proteins, and compounds that modulate the activity of the TAFI gene, i.e., modulate the level of TAFI gene expression and/or modulate the level of TAFI gene product or protein activity.

For example, functional assays can be used to screen for compounds that modulate TAFI gene product activity. In such assays, compounds are screened for agonistic or antagonistic activity with respect to a biological activity or function of the TAFI protein or polypeptide, such as changes in the activation of plasminogen to plasmin by t-PA, or changes in the activity of the TAFI protein on a known substrate.

According to preferred embodiments, assays utilizing TAFI substrates such as hippuryl arginine or N-benzoyl-Ala-Arg can be used to determine the agonistic or antagonistic effect of a compound on the bTAFI protein and/or polypeptides of the invention. Briefly, the bTAFI protein is activated, e.g., in the presence of thrombin and thrombomodulin, or alternatively, trypsin, prior to the assay. The bTAFI protein is then mixed with the substrate either alone or in the presence of a test compound and the hydrolysis of the substrate is measured, e.g., via HPLC or by detection of fluorescence, depending on the assay used. A test compound that decreases the hydrolytic activity of the bTAFI protein compared to a control in the assay is identified as a TAFI antagonist whereas a test compound that increases the bTAFI protein activity is identified as a TAFI agonist. For details of two such assays, see Examples herein.

Compounds that have an agonistic, i.e., stimulatory, modulatory effect on bTAFI activity are compounds that produce an increased inhibition of fibrinolysis, e.g., a decrease in plasminogen activation to plasmin in vivo, whereas those compounds having an antagonistic modulatory effect on bTAFI activity are those that produce a decrease in fibrinolysis inhibition. Given the high degree of homology between the bTAFI gene products of the invention and human TAFI, the compounds identified by these assays may be useful, e.g., in modulating the activity of wild type and/or mutant human TAFI gene products in vivo, in elaborating the biological function of the human TAFI gene product in vivo, and in screens for identifying compounds that disrupt normal human TAFI protein interactions in vivo, or may in themselves disrupt such interactions.

Screening assays may also be designed to identify compounds capable of binding to the bTAFI gene products of the invention. By virtue of such binding, these compounds may also be useful in modulating or elucidating the activity of human TAFI proteins in vivo. The principle of such screening assays to identify compounds that bind to the bTAFI gene product involves preparing a reaction mixture of the bTAFI gene product and the test compound under conditions and for a time sufficient to allow the two components to interact with, i.e., bind to, and thus form a complex, which can represent a transient complex, which can be removed and/or detected in the reaction mixture. For example, one assay involves anchoring a bTAFI gene product or the test substance onto a solid phase and detecting bTAFI gene product/test compound complexes anchored on the solid phase at the end of the reaction. In one embodiment of such a method, the bTAFI gene product may be anchored onto a solid surface, and the test compound, which is not anchored, may be labeled, either directly or indirectly.

The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected, e.g., using an immobilized antibody specific for bTAFI gene product or the test compound to anchor any complexes formed in solution, and a labeled antibody specific for the other component of the possible complex to detect anchored complexes.

Similarly, compounds that modulate TAFI gene product activity can also include compounds that bind to other proteins that interact with the bTAFI gene product of the invention. These modulatory compounds can be identified by first identifying those proteins that interact with the bTAFI gene product, e.g., by standard techniques known in the art for detecting protein-protein interactions, such as co-immunoprecipitation, crosslinking and co-purification through gradients or chromatographic columns. Utilizing procedures such as these allows for the isolation of proteins that interact with bTAFI gene products or polypeptides of the invention as described supra. Once isolated, such a protein can be identified and can, in turn, be used, in conjunction with standard techniques, to identify additional proteins with which it interacts.

Additionally, methods may be employed that result in the simultaneous identification of genes which encode proteins interacting with TAFI gene products or polypeptides. These methods include, for example, probing expression libraries with labeled bTAFI gene products of the invention, using TAFI protein or polypeptide in a manner similar to the well known technique of antibody probing of λgt11 libraries. One method that detects protein interactions in vivo is the two-hybrid system. A version of this system in described by Chien et al., 1991, Proc. Natl. Acad. Sci. USA, 88:9578–9582 and is commercially available from Clontech (Palo Alto, Calif.).

Compounds that disrupt TAFI interactions with its interacting or binding partners, as determined immediately above, may be useful in regulating the activity of the TAFI gene product, including mutant TAFI proteins and polypeptide. Such compounds may include, but are not limited to, molecules such as peptides, and the like, which may bind to the bTAFI gene product as described above.

The basic principle of the assay systems used to identify compounds that interfere with the interaction between the TAFI gene product and its interacting partner or partners involves preparing a reaction mixture containing the bTAFI gene product of the invention, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of bTAFI gene product and its interacting partner. Control reaction mixtures are incubated without the test compound or with a placebo. The formation of any complexes between the bTAFI gene product and the interacting partner is then detected. The formation of a complex in the control reaction, but not in the reaction mixture containing the test compound, indicates that the compound interferes with the interaction of the bTAFI gene product and the interacting partner. Additionally, complex formation within reaction mixtures containing the test compound and the bTAFI gene product may also be compared to complex formation within reaction mixtures containing the test compound and a mutant TAFI gene product. This comparison may be important in those cases wherein it is desirable to identify compounds that disrupt interactions of mutant but not normal TAFI proteins.

The assay for compounds that interfere with the interaction of TAFI gene products and interacting partners can be conducted in a heterogeneous or homogeneous format. Heterogeneous assays involve anchoring either the bTAFI gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the bTAFI gene products and the interacting partners, e.g., by competition, can be identified by conducting the reaction in the presence of the test substance; i.e., by adding the test substance to the reaction mixture prior to or simultaneously with the bTAFI gene product and interacting partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the bTAFI gene product or the interacting partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the TAFI gene product or interacting partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the interacting components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment, a preformed complex of the bTAFI gene protein and the interacting partner is prepared in which either the bTAFI gene product or its interacting partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt bTAFI gene protein/interacting partner interaction can be identified.

In another embodiment of the invention, these same techniques can be employed using peptide fragments that correspond to the binding domains of the bTAFI protein and/or the interacting partner, in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected.

Sequence analysis of the genes encoding the respective proteins will reveal the mutations that correspond to the region of the protein involved in interacting, e.g., binding. Alternatively, one protein can be anchored to a solid surface using methods described herein above, and allowed to interact with, e.g., bind, to its labeled interacting partner, which has been treated with a proteolytic enzyme, such as trypsin. After washing, a short, labeled peptide comprising the interacting, e.g., binding, domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

In addition, cellular assays are known that can be used to identify compounds that interact with the TAFI gene and/or gene product, e.g., modulate the activity of the gene and/or bind to the gene product. Such cell-based assays of the invention utilize cells, cell lines, or engineered cells or cell lines that express a bTAFI gene product of the invention.

According to one embodiment, such methods comprise contacting a compound to a cell that expresses the bTAFI nucleic acid sequence of the invention, measuring the level of gene expression, gene product expression, or gene product activity, and comparing this level to the level of the bTAFI gene expression, gene product expression, or gene product activity produced by the cell in the absence of the compound, such that if the level obtained in the presence of the compound differs from that obtained in its absence, a compound that modulates the expression of the bTAFI gene and/or the synthesis or activity of the gene product has been identified. In an alternative embodiment, such methods comprise administering a compound to a host organism, e.g., a transgenic animal that expresses a bTAFI transgene or a mutant bTAFI transgene, and measuring the level of bTAFI gene expression, gene product expression, or gene product activity. The measured level is compared to the level of bTAFI gene expression, gene product expression, or gene product activity in a host that is not exposed to the compound, such that if the level obtained when the host is exposed to the compound differs from that obtained when the host is not exposed to the compound, a compound that modulates the expression of the bTAFI gene and/or the synthesis or activity of bTAFI gene products has been identified.

The compounds identified by these methods include therapeutic compounds that can be used as pharmaceutical compositions to treat blood clotting disorders such as hemophilia, von Willebrand's disease or thrombotic disease.

Methods and Compositions for the Treatment of Blood Clotting Disorders

The present invention also relates to methods and compositions for the treatment or modulation of any disorder or cellular process that is mediated or regulated by TAFI gene product expression or function, e.g., TAFI-mediated fibrinolysis inhibition, such as the various blood clotting disorders disclosed supra.

The methods of the invention include methods that modulate TAFI gene and gene product activity. In certain instances, the treatment will require an increase, upregulation or activation of TAFI activity, while in other instances, the treatment will require a decrease, downregulation or suppression of TAFI activity. "Increase" and "decrease" refer to the differential level of TAFI activity relative to TAFI activity in the cell type of interest in the absence of modulatory treatment. Methods for the decrease of TAFI activity are discussed in herein. Methods for the increase of TAFI activity are discussed in herein. Methods which can either increase or decrease TAFI activity depending on the particular manner in which the method is practiced are discussed in herein.

Methods for Decreasing TAFI Activity

Successful treatment of blood clotting disorders that involve an increase in TAFI activity, such as thrombotic disease, can be brought about by methods which serve to decrease the fibrinolysis inhibitory activity of the TAFI protein. Activity can be decreased by, e.g., directly decreasing TAFI gene product activity and/or by decreasing the level of TAFI gene expression.

For example, compounds such as those identified through assays described in herein, that decrease TAFI gene product activity can be used in accordance with the invention to ameliorate symptoms associated with these blood clotting disorders. As discussed supra, such molecules can include, but are not limited to peptides, including soluble peptides, and small organic or inorganic molecules, and can be referred to as TAFI antagonists or inhibitors. Techniques for the determination of effective doses and administration of such compounds are described in herein.

In addition, antisense and ribozyme molecules that inhibit TAFI gene expression can also be used to reduce the level of TAFI gene expression, thus effectively reducing the level of TAFI gene product present, thereby decreasing the level of TAFI activity. Still further, triple helix molecules can be utilized in reducing the level of TAFI gene expression. Such molecules can be designed to reduce or inhibit either wild type, or if appropriate, mutant target gene activity. Techniques for the production and use of such molecules are well known to those of skill in the art.

Antisense oligonucleotides may be single or double stranded. Double stranded RNA's may be designed based upon the teachings of Paddison et al., Proc. Nat. Acad. Sci., 99:1443–1448 (2002); and International Publication Nos. WO 01/29058, and WO 99/32619; which are hereby incorporated herein by reference.

For example, antisense approaches involve the design of oligonucleotides (either DNA or RNA) that are complementary to TAFI gene mRNA. The antisense oligonucleotides will bind to the complementary TAFI gene mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Using the bTAFI nucleic acid sequences of the invention, oligonucleotides complementary to TAFI mRNA can be generated for use in an antisense approach to inhibit translation of endogenous TAFI gene mRNA. The bTAFI antisense nucleic acids of the invention should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, results obtained using the antisense oligonucleotide are preferably compared with those obtained using a control oligonucleotide. It is preferred that the control oligonucleotide is of approximately the same length as the antisense oligonucleotide and that the nucleotide sequence of the control oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc.

The oligonucleotide may also include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Application No. WO88/09810) or the blood-brain barrier (see, e.g., PCT Application No. WO 89/10134), or hybridization-triggered cleavage agents (see, e.g., Krol et al., 1988, BioTechniques 6:958–976) or intercalating agents (see, e.g., Zon, 1988, Pharm. Res. 5:539–549). For example, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). In another embodiment, the oligonucleotide is a 2-0-methylribonucleotide (Inoue et al., 1987, Nucl. Acids Res. 15:6131–6148), or a chimeric RNA-DNA analogue (Inoue et al., 1987, FEBS Lett. 215: 327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The antisense molecules should be delivered to cells which express the TAFI gene in vivo. A number of methods have been developed for delivering antisense DNA or RNA to cells; e.g., antisense molecules can be injected directly into the tissue site or modified antisense molecules designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Thus, a preferred approach utilizes a recombinant DNA construct in which the bTAFI antisense oligonucleotide is placed under the control of a strong pol III or pol II promoter. The use of such a construct to transfect target cells in the patient will result in the transcription of sufficient amounts of single stranded RNAs that will form complementary base pairs with the endogenous TAFI gene transcripts and thereby prevent translation of the TAFI gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art that are used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3 prime long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review, see, e.g., Rossi, J., 1994, Current Biology 4:469–471). The mechanism of ribozyme action involves sequence-specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. Thus, the bTAFI nucleic acid sequences of the invention can be used to generate the appropriate ribozyme for use according to this approach.

Also, within the scope of the invention are engineered hammerhead motif ribozyme molecules that specifically and efficiently catalyze endonucleolytic cleavage of RNA sequences encoding target gene proteins. The ribozymes of the present invention also include RNA endoribonucleases (hereinafter referred to as "Cech-type ribozymes") such as the one which occurs naturally in *Tetrahymena Thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; PCT Patent Application No. WO 88/04300; Been and Cech, 1986, Cell, 47:207–216). The Cech-type ribozymes have an eight base pair active site which hybridizes to a target RNA sequence, after which cleavage of the target RNA takes place. The invention encompasses those Cech-type ribozymes which target eight base-pair active site sequences that are present in the bTAFI gene of the invention.

As in the antisense approach, the ribozymes can be composed of modified oligonucleotides (e.g., for improved stability, targeting, etc.) and should be delivered to cells that express the TAFI gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous TAFI gene messages and inhibit translation. Because ribozymes, unlike antisense molecules, are catalytic, a lower intracellular concentration is required for efficiency.

In instances wherein the antisense and ribozyme molecules described herein are utilized to inhibit mutant TAFI gene expression, it is possible that the technique may so efficiently reduce or inhibit the translation of mRNA produced by normal target gene alleles that the concentration of normal target gene product present may be lower than is necessary for a normal phenotype. In such cases, to ensure that substantially normal levels of TAFI gene activity are maintained, nucleic acid molecules that encode and express bTAFI gene polypeptides exhibiting normal target gene activity can be introduced into cells via gene therapy methods that do not contain sequences susceptible to whatever antisense, ribozyme, or triple helix treatments are being utilized. In instances where the target gene encodes an extracellular protein, it can be preferable to coadminister normal target gene protein in order to maintain the requisite level of target gene activity.

Antisense RNA and DNA and ribozyme molecules of the invention can be prepared by any method known in the art, e.g., methods for chemically synthesizing oligodeoxyribonucleotides and oligoribonucleotides well known in the art such as solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In addition, well-known modifications to DNA molecules can be introduced into the bTAFI nucleic acid molecules of the invention as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Methods for Increasing TAFI Activity

Successful treatment of blood clotting disorders that involve a decrease in normal TAFI activity, such as hemophilia, can also be brought about by techniques which serve to increase the level of TAFI activity. Activity can be increased by, for example, directly increasing TAFI gene product activity and/or by increasing the level of TAFI gene expression.

For example, compounds such as those identified through the assays described in herein, that increase TAFI activity can be used to treat such blood clotting disorders. Such molecules can include, but are not limited to peptides, including soluble peptides, and small organic or inorganic molecules, and can be referred to as TAFI agonists.

For example, a compound can, at a level sufficient to treat blood clotting disorders and symptoms, be administered to a patient exhibiting such symptoms. One of skill in the art will readily know how to determine the concentration of effective, non-toxic doses of the compound, utilizing techniques such as those described infra.

In instances wherein the compound to be administered is a peptide compound, DNA sequences encoding the peptide compound can be directly administered to a patient exhibiting a blood clotting disorder or symptoms, at a concentration sufficient to produce a level of peptide compound sufficient to ameliorate the symptoms of the disorder. Any of the techniques discussed infra, which achieve intracellular administration of compounds, such as, for example, liposome administration, can be utilized for the administration of such DNA molecules. In the case of peptide compounds which act extracellularly, the DNA molecules encoding such peptides can be taken up and expressed by any cell type, so long as a sufficient circulating concentration of peptide results for the elicitation of a reduction in the blood clotting disorder symptoms.

In cases where the disorder can be localized to a particular portion or region of the body, the DNA molecules encoding such modulatory peptides may be administered as part of a delivery complex. Such a delivery complex can comprise an appropriate nucleic acid molecule and a targeting means. Such targeting means can comprise, for example, sterols, lipids, viruses or target cell specific binding agents. Viral vectors can include, but are not limited to adenovirus, adeno-associated virus, and retrovirus vectors, in addition to other particles that introduce DNA into cells, such as liposomes.

Further, in instances wherein the blood clotting disorder involves an aberrant TAFI gene, patients can be treated by gene replacement therapy. One or more copies of the bTAFI gene or a portion of the gene that directs the production of a functional TAFI gene protein, can be inserted into cells, via, for example a delivery complex as described supra.

Such gene replacement techniques can be accomplished either in vivo or in vitro. Techniques which select for expression within the cell type of interest are preferred. For in vivo applications, such techniques can, for example, include appropriate local administration of bTAFI gene sequences of the invention.

Additional methods which may be utilized to increase the overall level of TAFI activity include the introduction of appropriate bTAFI gene-expressing cells, preferably autologous cells, into a patient at positions and in numbers which are sufficient to ameliorate the symptoms of the blood clotting disorder. The bTAFI gene sequences are introduced into autologous cells in vitro. These cells expressing the bTAFI gene sequence are then reintroduced, preferably by intravenous administration, into the patient until the disorder is treated and symptoms of the disorder are ameliorated. The cells can be administered at the anatomical site of expression, or as part of a tissue graft located at a different site in the body. Such cell-based gene therapy techniques are well known to those skilled in the art (see, e.g., Anderson, et al., U.S. Pat. No. 5,399,349; Mulligan and Wilson, U.S. Pat. No. 5,460,959).

Additional Modulatory Techniques

The present invention also includes modulatory techniques which, depending on the specific application for which they are utilized, can yield either an increase or a decrease in TAFI activity levels leading to the amelioration of blood clotting disorders such as those described above.

Antibodies exhibiting modulatory capability can be utilized according to the methods of this invention to treat blood clotting disorders. Depending on the specific antibody, the modulatory effect can be an increase or decrease in TAFI activity. Such antibodies can be generated using standard techniques described in herein, against the full length bTAFI proteins of the invention, or against polypeptides or peptides corresponding to portions of the proteins. The antibodies include, but are not limited to, polyclonal, monoclonal, Fab fragments, single chain antibodies, chimeric antibodies, etc.

Lipofectin or liposomes can be used to deliver the bTAFI antibody or a fragment of the Fab region which binds to the TAFI gene product epitope to cells expressing the gene product. Where fragments of the antibody are used, the smallest inhibitory fragment which binds to the TAFI protein's binding domain is preferred. For example, peptides having an amino acid sequence corresponding to the domain of the variable region of the antibody that binds to the TAFI protein can be used. Such peptides can be synthesized chemically or produced via recombinant DNA technology using methods well known in the art (e.g., see Creighton, 1983, supra and Sambrook et al., 1989, above). Alternatively, single chain antibodies, such as neutralizing antibodies, which bind to TAFI epitopes can also be administered. Such single chain antibodies can be administered, for example, by expressing nucleotide sequences encoding single-chain antibodies within the target cell population by utilizing, for example, techniques such as those described in Marasco et al., 1993, Proc. Natl. Acad. Sci. USA 90:7889–7893).

Pharmaceutical Preparations and Methods of Administration

The compounds of the invention, e.g., bTAFI nucleic acid sequences, proteins, polypeptides, peptides, and recombinant cells as well as bTAFI inhibitors and agonists identified by the methods of the invention as described supra can be administered to a patient at therapeutically effective doses to treat or ameliorate blood clotting disorders. A therapeutically effective dose refers to that amount of a compound or cell population sufficient to result in amelioration of the disorder symptoms, or alternatively, to that amount of a nucleic acid sequence sufficient to express a concentration of TAFI gene product which results in the amelioration of the disorder symptoms.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the) route of administration utilized. For any compound used in the methods of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. It is preferred that bTAFI-expressing cells be introduced into patients via intravenous administration.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

EXAMPLE

Identification of a Novel bTAFI Gene and its Encoded Protein

The section below describes the identification of novel baboon gene sequences encoding a novel baboon TAFI protein.

Cloning of Novel bTAFI DNA Sequences

In general, all routine molecular biology procedures followed standard protocols or relied on widely available commercial kits and reagents. The cDNA sequence of baboon TAFI was cloned from a baboon liver lambda phage library (Stratagene Catalog No. 936104). Using this cDNA library as a template, segments of baboon TAFI were cloned sequentially by PCR using primers 1 thru 13 (SEQ ID NO:3 thru 15) as depicted in FIG. 3 (using either Clontech Advantage PCR kit, Catalog No. K1909-Y, lot no. 9080543 or Stratagene clone Pfu DNA polymerase Catalog No. 600153). The starting PCR primers were chosen from DNA sequences of the closely related protein, human TAFI (GenBank, accession no. M75106) and mouse TAFI (GenBank, accession no. AF 164524). Sequentially, segments were cloned with primers based on DNA sequences from either reference TAFI or the baboon TAFI sequence itself as it was being determined.

The DNA sequence for bTAFI is depicted in FIGS. 1A–B. The derived protein, i.e., amino acid, sequence encoded by the bTAFI gene is depicted in FIGS. 1A–B.

Expression and Purification of a Novel bTAFI Protein

For expression of bTAFI protein, a bTAFI/pFastBac expression plasmid was constructed in a two-step process as follows: First, the KpnI-BamHI segment of the bTAFI gene was cloned into pCR2.1 (Invitrogen, Carlsbad, Calif., Original TA cloning kits, Catalog No. K2000-01) to gain access to a 5' SpeI site, and second, the BamHI-EcoRV segment was cloned into pD16.MCS to gain access to a 3' XhoI site. Both segments were excised and purified before ligation into a pFastBac 1 plasmid (Invitrogen Catalog No. 10360-014) that had been restricted with SpeI and XhoI, yielding the final bTAFI/pFastBac expression plasmid (see, e.g., FIG. 3). This bTAFI/pFastBac plasmid was deposited with the American Type Culture Collection under accession no. PTA 3949. This plasmid was used to prepare a serum-free virus stock according manufacturer's instructions (GibcoBRL Bac-to-Bac Baculovirus Expression Systems instruction manual Catalog No. 10686-016).

bTAFI was then expressed in baculovirus infected sf9 cells in ESF921 medium (Expression Systems, Woodland, Calif.). To a series of 1 liter shake flasks containing $1 \times 10^6$ cells/ml, the infection was performed at an MOI of 0.5. The flasks were placed on a shaker at 27° C. for 96 hours. The cell viability after 96 hours was about 85%. The conditioned media containing the recombinant bTAFI was separated from the cells by filtration through a 0.22 μ filter. The expression titers were measured by an ELISA assay (Enzyme Research Laboratories, South Bend, Ind.) using a known TAFI as a reference standard.

The expressed bTAFI protein was purified as follows: 10 liters of baculovirus conditioned media from the expression system described above were concentrated 10 fold by tangential flow filtration on a 10 kD cut off membrane (Millipore, Bedford, Mass.). The concentrated supernatant was buffer exchanged using 5 volumes of 20 mM HEPES (pH 7.5). All solutions and chromatography steps were performed at 4° C. The solution was filtered through a 1 μ filter and run on a 5×5 cm column of Q-Sepharose-HP (Amersham Pharmacia, Piscataway, N.J.) at a flow rate of 10 ml/min. The column was washed with 5 column volumes of 20 mM HEPES (pH 7.5) followed by a gradient of NaCl from 0–0.2M NaCl in 4.5 column volumes and then with a gradient of 0.2–2 M NaCl over 6 column volumes. The bTAFI in the flow, wash and early part of the NaCl gradient (0–100 mM NaCl) was pooled and the pH was adjusted to 7.2 with 1 M HEPES-HCl. The solution was loaded on a 3.7×2.6 column of SP-Sepharose-HP (Amersham Pharmacia, Piscataway, N.J.) at a flow rate of 10 ml/min. The column was washed with 12 column volumes of 20 mM HEPES (pH 7.2), followed by a gradient from 0–0.45M NaCl over 40 column volumes. The bTAFI eluted between 0.3–0.4 M NaCl.

The molecular weight of the purified bTAFI protein as determined by SDS-PAGE (reduced conditions, MES buffer, 4–12% Novex NuPAGE gel; Invitrogen, Carlsbad, Calif.) was approximately 50 kD and the protein was approximately 95% pure as determined by densitometry.

The bTAFI was also activated by treatment with thrombin under conditions essentially as set forth in Bajzar et al., 1995, JBC 270: 14477–14484. bTAFI at 0.3 mg/ml in 50 mM HEPES, 0.15 M NaCl, 10 mM $CaCl_2$, pH 7.4, was incubated with 18 Units/ml thrombin at room temperature. At specific times of incubation, i.e., 0, 5, 10, 15, 30, 60, and 90 min, aliquots were removed, quenched into SDS sample buffer containing 5% mercaptoethanol and run on an SDS-PAGE gel. The SDS-PAGE indicated that the 50 kD band of the purified bTAFI protein was converted to a 36 kD activated bTAFI protein (bTAFIa) and a 25 kD activation peptide (see FIG. 4). The theoretical molecular weights of bTAFIa and the activation peptide without post-translational modifications are 36,101 Da and 10,088 Da, respectively. Three potential N-linked glycosylation sites exist on the activation peptide at Asn residues N-51, N-63 and N-86, but none are predicted to be within the catalytic domain. The apparent higher molecular weight of the activation peptide on SDS-PAGE is consistent with this glycosylation.

Finally, the zero and 90 min time point aliquots were run on SDS-PAGE and transferred to a PVDF (polyvinylidene difluoride) membrane (Invitrogen) for N-terminal sequence analysis of the purified bTAFI and bTAFIa proteins. The N-terminal sequence analysis indicated an N-terminal sequence of FQSGQ for the bTAFI protein and an N-terminal sequence of ASASY for the bTAFIa protein. These sequences are in accordance with other reported TAFI and PCPB N-terminal sequences.

Functional Assays for Screening for TAFI Antagonists and Agonists

The following assay was used to identify compounds that either inhibit TAFI activity (antagonists) or compounds that enhance TAFI activity (agonists). The assay was carried out as follows:

First, the recombinant bTAFI produced by the expression system described supra was activated with thrombin and thrombomodulin. 80 μl thrombin (0.4 U/ml) was mixed with 80 μl thrombomodulin (160 nM )(from Haematologic Technologies Inc., Cat. No. RTM-2020, Lot No. 922; rabbit lung thrombomodulin) in 20 mM HEPES/5 mM $CaCL_2$/0.01% Tween 80 (polyoxyethylenesorbitan monooleate) (pH 7.4) buffer. Equal volumes of this thrombin-thrombomodulin activation mixture and recombinant bTAFI at, e.g., 0.5 μg/ml in 20 mM HEPES (pH 7.4), were mixed and incubated for 10 min at room temperature. The reaction was then stopped by the addition of the thrombin inhibitor, PPACK (CalBiochem, La Jolla, Calif.).

The activated TAFI was then mixed with the substrate hippuryl arginine (from Sigma, FW=335.4) either alone or in the presence of varying concentrations of test compound with additional reagents, e.g., as depicted below:

|  | BLANK | CONTROLS | test compound | Calibrator |
|---|---|---|---|---|
| ADDITIONS (reagents | ul | ul | ul | ul |
| activated TAFI | — | 10 | 10 | — |
| 20 mM HEPES | 10 | — | — | — |
| Hippuric Acid, 2.25 mM | — | — | — | 10 |
| test compound | 15 | 15 | 15 | 15 |
| Substrate: 48 mM hippuryl arginine | 25 | 25 | 25 | 25 |

Each test compound (in 50 mM HEPES buffer, 1% DMSO) was tested in this assay with a corresponding PCI (potato carboxypeptidase inhibitor; e.g., from Sigma, St. Louis, Mo.) or a DMSO blank control (3.33% in 50 mM HEPES, pH 8). PCI is a TAFI inhibitor and so was run as a control with which to compare the inhibitory activity of the test compound. The substrate, hippuryl arginine was prepared as a 48 mM stock solution in HPLC assay buffer, 50 mM HEPES buffer, (pH 8). Hippuric acid (2.25 mM)(from Aldrich Chem. Co., Milwaukee, Wis., Cat. No. 11200-3; FW=179.18) was used as a reagent for calibration.

The reaction mixture was incubated for 30 min at 37° C. and then HCl was added to stop the reaction:

| 1M HCl | 50 | 50 | 50 | 50 |
|---|---|---|---|---|
| O-methylhippuric acid, 15 mM | 10 | 10 | 10 | 10 |
| Ethyl Acetate | 300 | 300 | 300 | 300 |

The O-methyhippuric acid (MHA) reagent (an internal standard; from Aldrich Chem. Co., Cat. No. 32,800-6; FW=193.2) was dissolved in 100% ETOH and diluted four-fold with water to a concentration of 15 mM.

The reaction mixture was then vortexed for 30 sec and centrifuged for 2 min at high speed in a microfuge. A 200 ul aliquot of the supernatant was evaporated at 120° C. for 5 min or until dry on heating block and then redissolved in 150 ul of mobile phase (12.3 mM solution of phosphoric acid brought to a pH of 3.5 with KOH, with acetonitrile added to a concentration of 30% v/v). 15 µl was injected for HPLC analysis using a YMC-Pack Pro $C_{18}$ column (150×4.6 mm I.D., YMC, Inc., Wilmington, N.C.). Each was run was monitored at $A_{228}$ in mobile phase for 5 min. See also, Schatteman et al., 1999, Clinical Chemistry 45:6, 807–813, 1999; Hendriks et al., 1985, Clinical Chemistry 31(12): 1936–1939; Schatteman et al., 1999, Thromb Haemost 82:1718–21 and Silveira et al., 2000, Thromb Haemost 84:364–8 for details of typical HPLC activity assays.

The hydrolysis of the HipArg substrate to hippuric acid in the reaction mixture of this assay was measured by the HPLC and used to determine the effect of the test compound on TAFI activity, i.e., whether the test compound enhanced TAFI activity compared to controls and was therefore a TAFI agonist or inhibited TAFI activity compared to controls and was therefore a TAFI inhibitor or antagonist.

An alternative assay for obtaining TAFI antagonists or agonists was carried out as follows: bTAFI of the invention at 3 µg/ml was activated to bTAFIa by incubation with 1 µg/ml bovine trypsin (Sigma, T1426; St. Louis, Mo.) in 20 mM HEPES, 10 mM $CaCL_2$/0.01% Tween 80 (pH 7.4) buffer for 15 min at room temperature. The reaction was terminated by the addition of 1.6 µM TLCK (1-chloro-3-tosylamido-7-amino-L-2-heptanone (Roche Diagnostics, Indianapolis, Ind.). In a black bottom 96-well plate (Corning, Acton, Mass.), 35 µl of HEPES-PEG buffer (25 mM HEPES, 0.1 M NaCl, 1 mg/ml polyethylene glycol-8000 (pH 7.4)) was added, followed by 5 µl of the bTAFIa solution.

The reaction was started with the addition of 10 µl of 10 mM N-benzoyl-Ala-Arg substrate (Bachem Bioscience, Inc., King of Prussia, Pa.) in HEPES-PEG buffer. After incubation for 1 h at room temperature, 50 µl 1 M $Na_2HPO_4$ was added, mixed for 1 min, and 100 µl 0.4 mg/ml OPA (o-phthaldialdehyde (Sigma)) in 2% ethanol, 0.1% mercaptoethanol, 1M $Na_2HPO_4$ was added. The solution was mixed for 30 min and the fluorescence emission was read at 465 nm using an excitation wavelength of 340 nm.

The activated bTAFI acts on the N-benzoyl-Ala-Arg substrate to release Arg which is then detected by fluorescence. As with the HPLC assay above, a test compound that inhibits the activity of the bTAFIa in this assay, i.e., causes a decrease in fluorescence compared to a standardized control, is identified as a TAFI antagonist or inhibitor whereas a test compound that increases the activity of the bTAFIa, i.e., detected by an increase in flourescence in this assay, is identified as a TAFI agonist.

The bTAFI polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a bTAFI polypeptide, or a bindable peptide fragment, of this invention, comprising providing a plurality of compounds, combining the bTAFI polypeptide, or a bindable peptide fragment, with each of a plurality of compounds for a time sufficient to allow binding under suitable conditions and detecting binding of the bTAFI polypeptide or peptide to each of the plurality of test compounds, thereby identifying the compounds that specifically bind to the bTAFI polypeptide or peptide.

Methods of identifying compounds that modulate the activity of the novel bTAFI polypeptides and/or peptides are provided by the present invention and comprise combining a potential or candidate compound or drug modulator of thrombin-activatable fibrinolysis inhibitors biological activity with an bTAFI polypeptide or peptide, for example, the bTAFI amino acid sequence as set forth in SEQ ID NO:2, and measuring an effect of the candidate compound or drug modulator on the biological activity of the bTAFI polypeptide or peptide. Such measurable effects include, for example, physical binding interaction; the ability to cleave a suitable thrombin-activatable fibrinolysis inhibitors substrate; effects on native and cloned bTAFI-expressing cell line; and effects of modulators or other thrombin-activatable fibrinolysis inhibitors-mediated physiological measures.

Another method of identifying compounds that modulate the biological activity of the novel bTAFI polypeptides of the present invention comprises combining a potential or candidate compound or drug modulator of a thrombin-activatable fibrinolysis inhibitors biological activity with a host cell that expresses the bTAFI polypeptide and measuring an effect of the candidate compound or drug modulator on the biological activity of the bTAFI polypeptide. The host cell can also be capable of being induced to express the bTAFI polypeptide, e.g., via inducible expression. Physiological effects of a given modulator candidate on the bTAFI polypeptide can also be measured. Thus, cellular assays for particular thrombin-activatable fibrinolysis inhibitors modulators may be either direct measurement or quantification of the physical biological activity of the bTAFI polypeptide, or they may be measurement or quantification of a physiological effect. Such methods preferably employ a bTAFI polypeptide as described herein, or an overexpressed recombinant bTAFI polypeptide in suitable host cells containing an expression vector as described herein, wherein the bTAFI polypeptide is expressed, overexpressed, or undergoes upregulated expression.

Another aspect of the present invention embraces a method of screening for a compound that is capable of modulating the biological activity of a bTAFI polypeptide, comprising providing a host cell containing an expression vector harboring a nucleic acid sequence encoding a bTAFI polypeptide, or a functional peptide or portion thereof (e.g., SEQ ID NOS:2); determining the biological activity of the expressed bTAFI polypeptide in the absence of a modulator compound; contacting the cell with the modulator compound and determining the biological activity of the expressed bTAFI polypeptide in the presence of the modulator compound. In such a method, a difference between the activity of the bTAFI polypeptide in the presence of the modulator compound and in the absence of the modulator compound indicates a modulating effect of the compound.

Essentially any chemical compound can be employed as a potential modulator or ligand in the assays according to the present invention. Compounds tested as thrombin-activatable fibrinolysis inhibitors modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel bTAFI polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261: 1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274-1520–1522) and U.S. Pat. No. 5,593, 853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a bTAFI polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a bTAFI polypeptide or peptide to measure a biological binding or ligand binding activity, the source may be a whole cell lysate that can be prepared by successive freeze-thaw cycles (e.g., one to three) in the presence of standard protease inhibitors. The bTAFI polypeptide may be partially or completely purified by standard protein purification methods, e.g., affinity chromatography using specific antibody described infra, or by ligands specific for an epitope tag engineered into the recombinant bTAFI polypeptide molecule, also as described herein. Binding activity can then be measured as described.

Compounds which are identified according to the methods provided herein, and which modulate or regulate the biological activity or physiology of the bTAFI polypeptides according to the present invention are a preferred embodiment of this invention. It is contemplated that such modulatory compounds may be employed in treatment and therapeutic methods for treating a condition that is mediated by the novel bTAFI polypeptides by administering to an individual in need of such treatment a therapeutically effective amount of the compound identified by the methods described herein.

In addition, the present invention provides methods for treating an individual in need of such treatment for a disease, disorder, or condition that is mediated by the bTAFI polypeptides of the invention, comprising administering to the individual a therapeutically effective amount of the bTAFI-modulating compound identified by a method provided herein.

Method of Creating N- and C-Terminal Deletion Mutants Corresponding to the bTAFI Polypeptide of the Present Invetion The present invention encompasses the creation of N- and C-terminal deletion mutants, in addition to any combination of N- and C-terminal deletions thereof, corresponding to the bTAFI polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length bTAFI polypeptide sequence (as described in Example 9, for example), appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the F23 to V423 N-terminal deletion mutant, the following primers could be used to amplify a cDNA fragment corresponding to this deletion mutant:

```
5' Primer 5'-GCAGC GCGGCCGC TTTCAGAGTGGCCAGGTTCTAGCTG-3'   (SEQ ID NO:21)
                 NotI 3' Primer 5'-GCAGCA GTCGAC AACATTCCTAATGACATGCCAAGC-3'    (SEQ ID NO:22)
                   SalI
```

For example, in the case of the M1 to I401 C-terminal deletion mutant, the following primers could be used to amplify a cDNA fragment corresponding to this deletion mutant:

```
5' Primer 5'-GCAGCA GCGGCCGC ATGAAGCTTTGCAGTCTTGCAGTCC-3'  (SEQ ID NO:23)
                   NotI 3' Primer 5'-GCAGCA GTCGAC GATGTAACGCTCAGGCAGCAAG-3'       (SEQ ID NO:24)
                   SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of bTAFI), 200 uM 4 dNTPs, 1 uM primers, 0.25U Taq DNA polymerase (PE), and standard Taq DNA polymerase buffer. Typical PCR cycling condition are as follows:

| 20–25 cycles: | 45 sec, 93 degrees |
| --- | --- |
|  | 2 min, 50 degrees |
|  | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E.coli cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the bTAFI gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac-sequences, etc.).

The 3' primer sequence for amplifying any additional N-terminal deletion mutants may be determined by reference to the following formula: (S+(X*3)) to ((S+(X*3))–25), wherein 'S' is equal to the nucleotide position of the initiating start codon of the bTAFI gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

In preferred embodiments, the following N-terminal bTAFI deletion polypeptides are encompassed by the present invention: M1-V423, K2-V423, L3-V423, C4-V423, S5-V423, L6-V423, A7-V423, V8-V423, L9-V423, V10-V423, P11-V423, I12-V423, V13-V423, L14-V423, F15-V423, C16-V423, E17-V423, Q18-V423, H19-V423, V20-V423, F21-V423, A22-V423, F23-V423, Q24-V423, S25-V423, G26-V423, Q27-V423, V28-V423, L29-V423, A30-V423, A31-V423, L32-V423, P33-V423, R34-V423, T35-V423, S36-V423, R37-V423, Q38-V423, V39-V423, Q40-V423, V41-V423, L42-V423, Q43-V423, N44-V423, L45-V423, T46-V423, T47-V423, T48-V423, Y49-V423, E50-V423, I51-V423, V52-V423, L53-V423, W54-V423, Q55-V423, P56-V423, V57-V423, T58-V423, A59-V423, D60-V423, L61-V423, I62-V423, E63-V423, K64-V423, K65-V423, K66-V423, Q67-V423, V68-V423, H69-V423, F70-V423, F71-V423, V72-V423, N73-V423, S74-V423, S75-V423, D76-V423, V77-V423, D78-V423, N79-V423, V80-V423, K81-V423, A82-V423, H83-V423, L84-V423, N85-V423, V86-V423, S87-V423, G88-V423, I89-V423, P90-V423, C91-V423, S92-V423, V93-V423, L94-V423, L95-V423, A96-V423, D97-V423, V98-V423, E99-V423, D100-V423, L101-V423, I102-V423, Q103-V423, Q104-V423, Q105-V423, I106-V423, S107-V423, N108-V423, D109-V423, T110-V423, V111-V423, S112-V423, P113-V423, R114-V423, A115-V423, S116-V423, A117-V423, S118-V423, Y119-V423, Y120-V423, E121-V423, Q122-V423, Y123-V423, H124-V423, S125-V423, L126-V423, N127-V423, E128-V423, I129-V423, Y130-V423, S131-V423, W132-V423, I133-V423, E134-V423, L135-V423, I136-V423, T137-V423, E138-V423, K139-V423, Y140-V423, P141-V423, D142-V423, M143-V423, L144-V423, T145-V423, K146-V423, I147-V423, H148-V423, I149-V423, G150-V423, S151-V423, S152-V423, Y153-V423, E154-V423, K155-V423, H156-V423, P157-V423, L158-V423, Y159-V423, V160-V423, L161-V423, K162-V423, V163-V423, S164-V423, G165-V423, K166-V423, E167-V423, Q168-V423, T169-V423, A170-V423, K171-V423, N172-V423, A173-V423, M174-V423, W175-V423, I176-V423, D177-V423, C178-V423, G179-V423, I180-V423, H181-V423, A182-V423, R183-V423, E184-V423, W185-V423, I186-V423, S187-V423, P188-V423, A189-V423, F190-V423, C191-V423, L192-V423, W193-V423, F194-V423, I195-V423, G196-V423, H197-V423, I198-V423, T199-V423, E200-V423, Y201-V423, Y202-V423, G203-V423, I204-V423, I205-V423, G206-V423, E207-V423, Y208-V423, T209-V423, N210-V423, L211-V423, L212-V423, R213-V423, H214-V423, V215-V423, D216-V423, F217-V423, Y218-V423, V219-V423, M220-V423, P221-V423, V222-V423, V223-V423, N224-V423, V225-V423, D226-V423, G227-V423, Y228-V423, D229-V423, Y230-V423, S231-V423, W232-V423, K233-V423, K234-V423, N235-V423, R236-V423, M237-V423, W238-V423, R239-V423, K240-V423, N241-V423, R242-V423, S243-V423, F244-V423, Y245-V423, A246-V423, N247-V423, N248-V423, R249-V423, C250-V423, I251-V423, G252-V423, T253-V423, D254-V423, L255-V423, N256-V423, R257-V423, N258-V423, F259-V423, A260-V423, S261-V423, K262-V423, H263-V423, W264-V423, C265-V423, E266-V423, E267-V423, G268-V423, A269-V423, S270-V423, S271-V423, F272-V423, S273-V423, C274-V423, S275-V423, E276-V423, T277-V423, Y278-V423, C279-V423, G280-V423, L281-V423, Y282-V423, P283-V423, E284-V423, S285-V423, E286-V423, P287-V423, E288-V423, A289-V423, K290-V423, A291-V423, V292-V423, A293-V423, N294-V423, F295-V423, L296-V423, R297-V423, R298-V423, N299-V423, I300-V423, N301-

V423, H302-V423, I303-V423, K304-V423, A305-V423, Y306-V423, I307-V423, S308-V423, M309-V423, H310-V423, S311-V423, Y312-V423, S313-V423, Q314-V423, H315-V423, I316-V423, V317-V423, F318-V423, P319-V423, Y320-V423, S321-V423, Y322-V423, T323-V423, R324-V423, S325-V423, K326-V423, S327-V423, K328-V423, D329-V423, H330-V423, E331-V423, E332-V423, L333-V423, S334-V423, L335-V423, V336-V423, A337-V423, S338-V423, E339-V423, A340-V423, V341-V423, R342-V423, A343-V423, I344-V423, Q345-V423, K346-V423, T347-V423, S348-V423, K349-V423, N350-V423, I351-V423, R352-V423, Y353-V423, T354-V423, H355-V423, G356-V423, R357-V423, G358-V423, S359-V423, E360-V423, T361-V423, L362-V423, Y363-V423, L364-V423, A365-V423, P366-V423, G367-V423, G368-V423, A369-V423, D370-V423, D371-V423, W372-V423, I373-V423, Y374-V423, D375-V423, L376-V423, G377-V423, I378-V423, K379-V423, Y380-V423, S381-V423, F382-V423, T383-V423, I384-V423, E385-V423, L386-V423, R387-V423, D388-V423, T389-V423, G390-V423, K391-V423, Y392-V423, G393-V423, F394-V423, L395-V423, L396-V423, P397-V423, E398-V423, R399-V423, Y400-V423, I401-V423, K402-V423, P403-V423, T404-V423, C405-V423, K406-V423, D407-V423, A408-V423, F409-V423, A410-V423, A411-V423, V412-V423, S413-V423, K414-V423, I415-V423, A416-V423, and/or W417-V423 of SEQ ID NO:2. Polynucleotide sequences encoding these polypeptides are also provided. The present invention also encompasses the use of these N-terminal bTAFI deletion polypeptides as immunogenic and/or antigenic epitopes as described elsewhere herein.

In preferred embodiments, the following C-terminal bTAFI deletion polypeptides are encompassed by the present invention: M1-V423, M1-N422, M1-R421, M1-I420, M1-V419, M1-H418, M1-W417, M1-A416, M1-I415, M1-K414, M1-S413, M1-V412, M1-A411, M1-A410, M1-F409, M1-A408, M1-D407, M1-K406, M1-C405, M1-T404, M1-P403, M1-K402, M1-I401, M1-Y400, M1-R399, M1-E398, M1-P397, M1-L396, M1-L395, M1-F394, M1-G393, M1-Y392, M1-K391, M1-G390, M1-T389, M1-D388, M1-R387, M1-L386, M1-E385, M1-I384, M1-T383, M1-F382, M1-S381, M1-Y380, M1-K379, M1-I378, M1-G377, M1-L376, M1-D375, M1-Y374, M1-I373, M1-W372, M1-D371, M1-D370, M1-A369, M1-G368, M1-G367, M1-P366, M1-A365, M1-L364, M1-Y363, M1-L362, M1-T361, M1-E360, M1-S359, M1-G358, M1-R357, M1-G356, M1-H355, M1-T354, M1-Y353, M1-R352, M1-I351, M1-N350, M1-K349, M1-S348, M1-T347, M1-K346, M1-Q345, M1-I344, M1-A343, M1-R342, M1-V341, M1-A340, M1-E339, M1-S338, M1-A337, M1-V336, M1-L335, M1-S334, M1-L333, M1-E332, M1-E331, M1-H330, M1-D329, M1-K328, M1-S327, M1-K326, M1-S325, M1-R324, M1-T323, M1-Y322, M1-S321, M1-Y320, M1-P319, M1-F318, M1-V317, M1-I316, M1-H315, M1-Q314, M1-S313, M1-Y312, M1-S311, M1-H310, M1-M309, M1-S308, M1-I307, M1-Y306, M1-A305, M1-K304, M1-I303, M1-H302, M1-N301, M1-I300, M1-N299, M1-R298, M1-R297, M1-L296, M1-F295, M1-N294, M1-A293, M1-V292, M1-A291, M1-K290, M1-A289, M1-E288, M1-P287, M1-E286, M1-S285, M1-E284, M1-P283, M1-Y282, M1-L281, M1-G280, M1-C279, M1-Y278, M1-T277, M1-E276, M1-S275, M1-C274, M1-S273, M1-F272, M1-S271, M1-S270, M1-A269, M1-G268, M1-E267, M1-E266, M1-C265, M1-W264, M1-H263, M1-K262, M1-S261, M1-A260, M1-F259, M1-N258, M1-R257, M1-N256, M1-L255, M1-D254, M1-T253, M1-G252, M1-I251, M1-C250, M1-R249, M1-N248, M1-N247, M1-A246, M1-Y245, M1-F244, M1-S243, M1-R242, M1-N241, M1-K240, M1-R239, M1-W238, M1-M237, M1-R236, M1-N235, M1-K234, M1-K233, M1-W232, M1-S231, M1-Y230, M1-D229, M1-Y228, M1-G227, M1-D226, M1-V225, M1-N224, M1-V223, M1-V222, M1-P221, M1-M220, M1-V219, M1-Y218, M1-F217, M1-D216, M1-V215, M1-H214, M1-R213, M1-L212, M1-L211, M1-N210, M1-T209, M1-Y208, M1-E207, M1-G206, M1-I205, M1-I204, M1-G203, M1-Y202, M1-Y201, M1-E200, M1-T199, M1-I198, M1-H197, M1-G196, M1-I195, M1-F194, M1-W193, M1-L192, M1-C191, M1-F190, M1-A189, M1-P188, M1-S187, M1-I186, M1-W185, M1-E184, M1-R183, M1-A182, M1-H181, M1-I180, M1-G179, M1-C178, M1-D177, M1-I176, M1-W175, M1-M174, M1-A173, M1-N172, M1-K171, M1-A170, M1-T169, M1-Q168, M1-E167, M1-K166, M1-G165, M1-S164, M1-V163, M1-K162, M1-L161, M1-V160, M1-Y159, M1-L158, M1-P157, M1-H156, M1-K155, M1-E154, M1-Y153, M1-S152, M1-S151, M1-G150, M1-I149, M1-H148, M1-I147, M1-K146, M1-T145, M1-L144, M1-M143, M1-D142, M1-P141, M1-Y140, M1-K139, M1-E138, M1-T137, M1-I136, M1-L135, M1-E134, M1-I133, M1-W132, M1-S131, M1-Y130, M1-I129, M1-E128, M1-N127, M1-L126, M1-S125, M1-H124, M1-Y123, M1-Q122, M1-E121, M1-Y120, M1-Y119, M1-S118, M1-A117, M1-S116, M1-A115, M1-R114, M1-P113, M1-S112, M1-V111, M1-T110, M1-D109, M1-N108, M1-S107, M1-I106, M1-Q105, M1-Q104, M1-Q103, M1-I102, M1-L101, M1-D100, M1-E99, M1-V98, M1-D97, M1-A96, M1-L95, M1-L94, M1-V93, M1-S92, M1-C91, M1-P90, M1-I89, M1-G88, M1-S87, M1-V86, M1-N85, M1-L84, M1-H83, M1-A82, M1-K81, M1-V80, M1-N79, M1-D78, M1-V77, M1-D76, M1-S75, M1-S74, M1-N73, M1-V72, M1-F71, M1-F70, M1-H69, M1-V68, M1-Q67, M1-K66, M1-K65, M1-K64, M1-E63, M1-I62, M1-L61, M1-D60, M1-A59, M1-T58, M1-V57, M1-P56, M1-Q55, M1-W54, M1-L53, M1-V52, M1-I51, M1-E50, M1-Y49, M1-T48, M1-T47, M1-T46, M1-L45, M1-N44, M1-Q43, M1-L42, M1-V41, M1-Q40, M1-V39, M1-Q38, M1-R37, M1-S36, M1-T35, M1-R34, M1-P33, M1-L32, M1-A31, M1-A30, M1-L29, M1-V28, M1-Q27, M1-G26, M1-S25, M1-Q24, M1-F23, M1-A22, M1-F21, M1-V20, M1-H19, M1-Q18, M1-E17, M1-C16, M1-F15, M1-L14, M1-V13, M1-I12, M1-P11, M1-V10, M1-L9, M1-V8, and/or M1-A7 of SEQ ID NO:2. Polynucleotide sequences encoding these polypeptides are also provided. The present invention also encompasses the use of these C-terminal bTAFI deletion polypeptides as immunogenic and/or antigenic epitopes as described elsewhere herein.

Three-Dimensional Structure of Baboon TAFI

Homology models are useful when there is no experimental information available on the protein of interest. A three-dimensional model can be constructed on the basis of the known structure of a homologous protein (Greer et al, Comparative modeling of homologous proteins. Methods In Enzymology 202 239–52, 1991, Lesk, et al, Homology Modeling: Inferences from Tables of Aligned Sequences. Curr. Op. Struc. Biol. (2) 242–247, 1992, Cardozo, et al, Homology modeling by the ICM method. Proteins 23, 403–14, 1995, Yuan, et al, 1995). The three-dimensional structure represented in the homology model of baboon TAFI (see FIG. 6) is defined by a set of structure coordinates as set forth in Table I.

Those skilled in the art will understand that a homology model is constructed on the basis of first identifying a template, or, protein of known structure which is similar in sequence to the protein without known structure. This can be accomplished by thorough pairwise alignment of sequences using such programs as FASTA (Pearson, et al Rapid and sensitive sequence comparison with FASTP and FASTA. Methods In Enzymology 18363–98, 1990) and BLAST (Altschul, et al, Basic local alignment search tool. J. Mol. Biol. 215, 403–10 1990).). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et al, Identification of native protein folds amongst a large number of incorrect models.

The calculation of low energy conformations from potentials of mean force. J. Mol. Biol. 216(1), 167–80, 1990), where the compatibility of a particular sequence with the three-dimensional fold of a potential template protein is gauged on the basis of a knowledge-based potential. Following the initial sequence alignment, the query template can be optimally aligned by manual manipulation or by incorporation of other features (motifs, secondary structure predictions, and allowed conservations). Next, structurally conserved regions can be identified and used to construct secondary core structure recognition (protein threading; Hendlich, et al, Identification of native protein folds amongst a large number of incorrect models. The calculation of low energy conformations from potentials of mean force. J. Mol. Biol. 216(1), 167–80, 1990). Loops can be added using knowledge-based techniques, and refined performing forcefield (Sali, et al., Evaluation of comparative protein modeling by MODELLER. PROTEINS 23, 318–26 1995)

The complete amino acid sequence of baboon TAFI is shown in FIG. 5 with the catalytic domain in boldface. The first 23 residues which are italicized comprise the signal peptide preceding the TAFI expressed protein, the next 91 residues, shown underlined, make up the activation domain which gets cleaved off by thrombin prior to activation, and the next 309 residues, appearing in boldface, comprise the TAFI catalytic domain. Only the baboon TAFI catalytic resiudes were modeled. Residues 1 to 114 (e.g., residues that are not in boldface in FIG. 5) were not considered.

The 309 residues which form the catalytic domain, will henceforth be referred to as residues 1–309 (residues 115 to 423 of SEQ ID NO:2). This convention is also the basis for the numbering of residue names in Table I for the baboon TAFI model atom coordinates.

The term "structure coordinates" refers to Cartesian coordinates generated from the building of a homology model. In the present invention, the homology model of residues 1 to 309 of baboon TAFI was derived by first carrying out a sequence similarity search for a suitable homolog using PSI-BLAST (Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402. ) on the database of PDB structures. The two most significant hits, as judged both by the lowest E-scores (Karlin, S. & Altschul, S. F. (1990) "Methods for assessing the statistical significance of molecular sequence features by using general scoring schemes." Proc. Natl. Acad. Sci. USA 87:2264–2268 ; Dembo, A., Karlin, S. & Zeitouni, O. (1994) "Limit distribution of maximal non-aligned two-sequence segmental score." Ann. Prob. 22:2022–2039) and sequence identities (45%), were reported as 1KWM, the PDB structure of baboon pancreatic procarboxypeptidase B [Pereira, P. J. B., Segura-Martin, S., Oliva, B., Ferrer-Orta, C., Aviles, F.-X., Coll, M., Gomis-Rueth, F.-X., Vendrell, J.: Baboon Procarboxypeptidase B: Three-Dimensional Structure and Implications for Thrombin-Activatable Fibrinolysis Inhibitor (Tafi), J.Mol.Biol. 321 pp. 537 (2002); Genbank Accession No.gi|21465928; SEQ ID NO:20], and 6CPA, the PDB structure of bovine pancreatic carboxypeptidase A [Kim, H., Lipscomb, W. N.: Crystal structure of the complex of carboxypeptidase A with a strongly bound phosphonate in a new crystalline form: comparison with structures of other complexes. Biochemistry 29 pp. 5546 (1990); Genbank Accession No.gi|231202; SEQ ID NO:19].

The multiple sequence alignment corresponding to these hits is shown in FIG. 5 and was used as the template for the homology model. Because of the relatively high E-score and sequence identity, and in particular the fact that the residues defining the catalytic site were preserved (see FIG. 5), it was deemed unnecessary to attempt using more sophisticated sequence alignment methods (such as threading) for producing sequence alignments.

Using the sequence alignment shown in FIG. 5, the COMPOSER module from the SYBYL program (version 6.7; Tripos Inc., St. Louis, Mo.) was used to build the homology model consisting of complete backbone and side-chain conformations. The insertions in the baboon TAFI sequence relative to its homologs consisted of no more than one residue and were away from the active site. The final model was optimized by relaxing the structure using an energy-minimization protocol in SYBYL (version 6.7; Tripos Inc., St. Louis, Mo.). The backbone atoms were held fixed while the sidechain atoms were relaxed in order to minimize the unfavorable interactions arising from steric bumps. In this initial refinement protocol, electrostatic effects were ignored.

Figure 7:
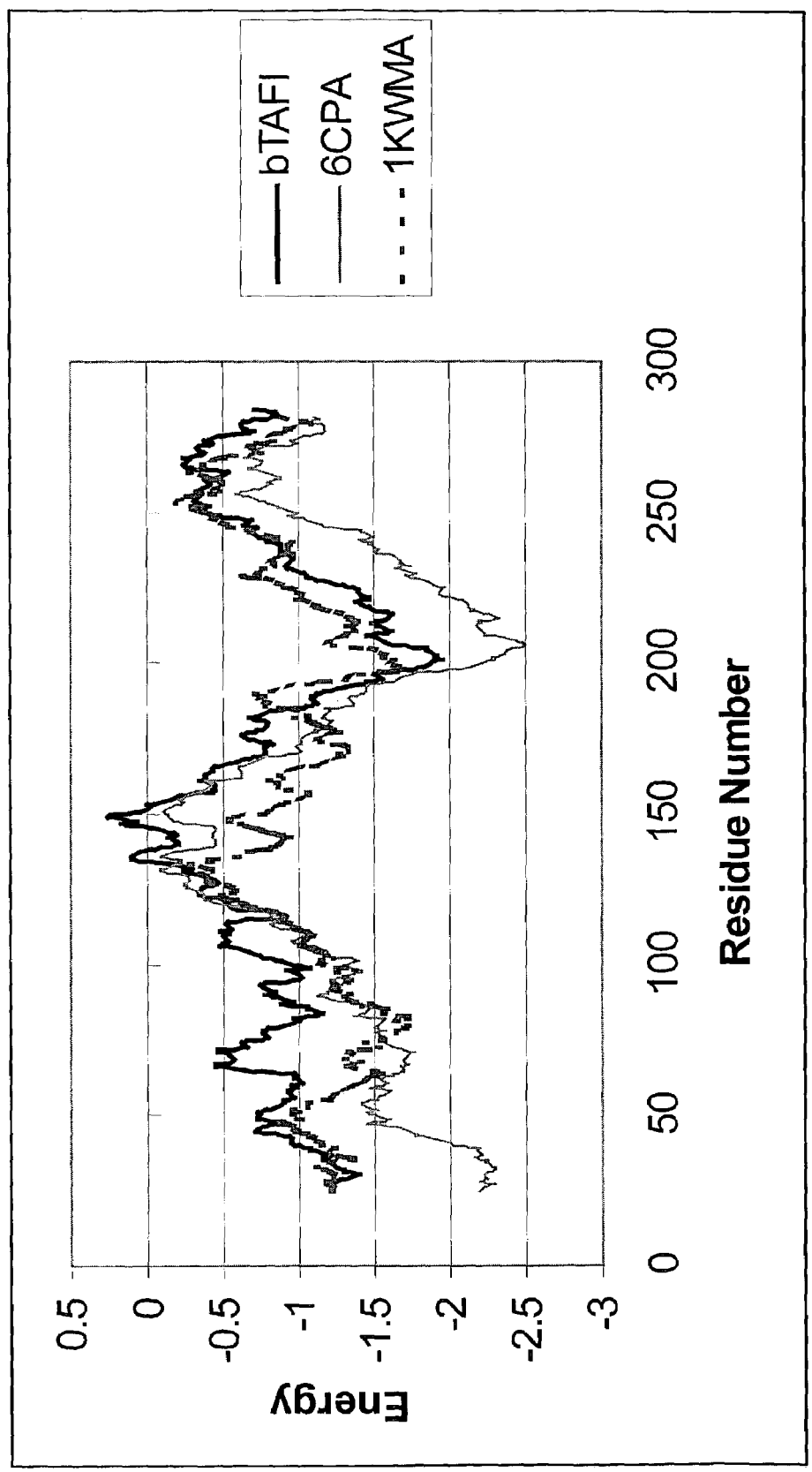
FIG. 7. Comparative variation of energy as a function of residue position in the sequence for the three proteins, baboon TAFI polypeptide of the present invention (SEQ ID NO:2), bovine carboxypeptidase A (6CPA; Genbank Accession No.gi|231202; SEQ ID NO:19), and baboon procarboxypeptidase B (1KWM; Genbank Accession No.; SEQ ID NO:20). The PROSAII program from Proceryon was used for calculating the energies as described herein.

The structural quality of the model, thusly refined, was assessed in two ways. First, the SYBYL program ProTable (Tripos Inc., St. Louis, Mo.) was used to ensure that in the final model, (i) there were no bad contacts, and (ii) the dihedral angles defining the backbone geometry had reasonable values consistent with known (($\phi$, $\psi$) distributions in proteins. Secondly, the PROSA program (Proceryon Biosciences Inc., New York, N.Y.) was used to calculate the energy distributions of residues in the model relative to those in the template they were built from (FIG. 7). This was done by threading each sequence through its structure and calculating the threading energies at each residue position. In order to smooth severe erratic behavior in the data, the data points were averaged over a 50-residue window. That is, each data point shown in FIG. 7 represents the energy average of 25 residues on either side of a given residue position. The results with the three energy plots overlaid are shown in FIG. 7. It is noted that the residue energies lie below 0, implying both local and global structural stability. The energy vs. residue number graph below shows the propensity of amino acids in the model sequence (baboon TAFI) for environments defined by the structural templates (1KWM and 6CPA), based on the sequence alignment shown in FIG. 5. The energies were calculated using the Proceryon software as described in the text.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates and/or using different methods in generating the homology model, will have minor effects on the overall shape. Variations in coordinates may also be generated because of mathematical manipulations of the structure coordinates. For example, the structure coordinates set forth in Table I could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of baboon TAFI described above as to be considered the same. Such analyses may be carried out in current software applications, such as SYBYL version 6.7/6.8 or INSIGHTII (Molecular Simulations Inc., San Diego, Calif.) version 2000 and as described in the accompanying User's Guides.

Using the superimposition tool in the program SYBYL comparisons can be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within SYBYL is defined by user input, for the purpose of this invention we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by SYBYL.

For the purpose of this invention, any homology model of baboon TAFI that has a root mean square deviation of conserved residue backbone atoms (N, Cα, C, O) of less than about 0.25 Å when superimposed on the corresponding backbone atoms described by structure coordinates listed in Table A are considered identical. More preferably, the root mean square deviation is less than about 0.1 Å.

In another embodiment of this invention, structural models wherein backbone atoms have been substituted with other elements which when superimposed on the corresponding backbone atoms have low root mean square deviations are considered to be identical.

For example, an homology model where the original backbone carbon, and/or nitrogen and/or oxygen atoms are replaced with other elements having a root mean square deviation of about 0.25 angstroms when superimposed on the corresponding backbone atoms described by structure coordinates listed in Table I is considered identical. More preferably, the root mean square deviation is less than about 0.1 Å.

For example, a homology model where the original backbone carbon, and/or nitrogen and/or oxygen atoms are replaced with other elements having a root mean square deviation of about 0.1 angstroms when superimposed on the corresponding backbone atoms described by structure coordinates listed in Table I is considered identical.

This invention as embodied by the homology model enables the structure-based design of modulators of the biological function of baboon TAFI, as well as mutants with altered biological function and/or specificity.

For purposes of the present invention, the active site region specifies the amino acids D63-P74, V109-N110, R122-N127, T139-F145, G154, E162-Y164, Y192-V203, S207, L248-D256, F268-D274, G279-F280, Zn whose structure coordinates appear in Table I, or analogue of said molecule involving simple truncations and/or mutations of amino acids, or in which the original C,N, and O atoms in said molecule are replaced with other elements.

In a preferred embodiment of the present invention, the molecule comprises at least a portion of the active site region defined by structure coordinates of baboon TAFI amino acids D63-P74, V109-N110, R122-N127, T139-F145, G154, E162-Y164, Y192-V203, S207, L248-D256, F268-D274, G279-F280, Zn according to Table I, or analogue of said molecule involving simple truncations and/or mutations of amino acids, or replacement in said molecule of the original C, N, and O atoms with other elements.

For purposes of the present invention, by "at least a portion of" it is meant all or any parts of the active site region defined by these structure coordinates according to Table I. More preferred are molecules comprising all or any parts of the active site region, according to Table I, or a mutant or homologue or analogue of said molecule or molecular complex. By mutant or homologue of the molecule it is meant a molecule that has a root mean square deviation from the backbone atoms of said baboon TAFI amino acids of not more than about 0.25 Angstroms.

By analogue is meant any structure involving simple substitution of the original backbone atoms with other elements such that the root mean square deviation from the backbone atoms of said baboon TAFI is-not more than about 0.1 Angstroms.

For purposes of the present invention, by "at least a portion of" it is meant all or any parts of the active site region defined by these structure coordinates according to Table I. More preferred are molecules comprising all or any parts of the active site region, according to Table I, or a mutant or homologue or analogue of said molecule or molecular complex. By mutant or homologue of the molecule it is meant a molecule that has a root mean square deviation from the backbone atoms of said baboon TAFI amino acids of not more than about 0.25 Angstroms.

By analogue is meant any structure involving simple substitution of the original backbone atoms with other elements such that the root mean square deviation from the backbone atoms of said baboon TAFI is not more than about 0.1 Angstroms.

For purposes of the present invention, by "at least a portion of" it is meant all or any parts of the active site region defined by these structure coordinates according to Table I. More preferred are molecules comprising all or any parts of the active site region, according to Table I, or a mutant or homologue or analogue of said molecule or molecular complex. By mutant or homologue of the molecule it is meant a molecule that has a root mean square deviation from the backbone atoms of said baboon TAFI amino acids of not more than about 0.25 Angstroms.

By analogue is meant any structure involving simple substitution of the original backbone atoms with other elements such that the root mean square deviation from the backbone atoms of said baboon TAFI is not more than about 0.1 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of the baboon TAFI portion of the complex as defined by the structure coordinates described herein.

The structure coordinates of a baboon TAFI homology model or portions thereof are stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table I.

For the first time, the present invention permits the use of structure-based or rational drug design techniques to design, select, and synthesize chemical entities that are capable of modulating the biological function of baboon TAFI.

Accordingly, the present invention is also directed to the active site binding region in baboon TAFI, on the basis of which a small molecule may be designed to bind to at least part of the region defined by the amino D63-P74, V109-N110, R122-N127, T139-F145, G154, E162-Y164, Y192-V203, S207, L248-D256, F268-D274, G279-F280, Zn or some portion thereof, according to Table I. By active site binding region, it is also meant to include mutants or homologues thereof, or transformations involving simple substitution of the original C, N, and O atoms with other elements. In a preferred embodiment, the mutants or homologues have at least 25% identity, more preferably 50% identity, more preferably 75% identity, and most preferably 90% identity D63-P74, V109-N110, R122-N127, T139-F145, G154, E162-Y164, Y192-V203, S207, L248-D256, F268-D274, G279-F280, Zn according to Table I.

The three-dimensional model structure of the baboon TAFI will also provide methods for identifying modulators of biological function. Various methods or combination thereof can be used to identify these compounds.

For example, test compounds can be modeled that fit spatially into the active site region in baboon TAFI embodied in the sequence D63-P74, V109-N110, R122-N127, T139-F145, G154, E162-Y164, Y192-V203, S207, L248-D256, F268-D274, G279-F280, Zn or some portion thereof, according to Table I.

Structure coordinates of the active site binding region in baboon TAFI defined by the amino acids D63-P74, V109-N110, R122-N127, T139-F145, G154, E162-Y164, Y192-V203, S207, L248-D256, F268-D274, G279-F280, Zn can also be used to identify structural and chemical features. Identified structural or chemical features can then be employed to design or select compounds as potential baboon TAFI ligands. By structural and chemical features it is meant to include, but is not limited to, covalent bonding, van der Waals interactions, hydrogen bonding interactions, charge interaction, hydrophobic bonding interaction, and dipole interaction. Alternatively, or in conjunction, the three-dimensional structural model can be employed to design or select compounds as potential baboon TAFI ligands. Compounds identified as potential baboon TAFI ligands can then be synthesized and screened in an assay characterized by binding of a test compound to the baboon TAFI, or in characterizing the ability of baboon TAFI to modulate a protease target in the presence of a small molecule. Examples of assays useful in screening of potential baboon TAFI ligands include, but are not limited to, screening in silico, in vitro assays and high throughput assays. Finally, these methods may also involve modifying or replacing one or more amino acids D63-P74, V109-N110, R122-N127, T139-F145, G154, E162-Y164, Y192-V203, S207, L248-D256, F268-D274, G279-F280, Zn from baboon TAFI according to Table I.

However, as will be understood by those of skill in the art upon this disclosure, other structure-based design methods can be used. Various computational structure-based design methods have been disclosed in the art.

For example, a number of computer modeling systems are available in which the sequence of the baboon TAFI and the baboon TAFI structure (i.e., atomic coordinates of baboon TAFI and/or the atomic coordinates of the active site region as provided in Table I) can be input. This computer system then generates the structural details of one or more these regions in which a potential baboon TAFI modulator binds so that complementary structural details of the potential modulators can be determined. Design in these modeling systems is generally based upon the compound being capable of physically and structurally associating with baboon TAFI. In addition, the compound must be able to assume a conformation that allows it to associate with baboon TAFI. Some modeling systems estimate the potential inhibitory or binding effect of a potential baboon TAFI modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in one or more of the cleaved reactive loop binding region, the heparin binding region, or the reactive loop in baboon TAFI. Docking is accomplished using software such as INSIGHTII, QUANTA and SYBYL, following by energy minimization and molecular dynamics with standard molecular mechanic force fields such as, MMFF, CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and baboon TAFI can be visualized and then assembled into a single potential modulator. Programs useful in assembling the individual chemical entities include, but are not limited to CAVEAT (Bartlett et al. 1989) and 3D Database systems (Martin 1992).

Alternatively, compounds may be designed de novo using either an empty active site or optionally including some portion of a known inhibitor. Methods of this type of design include, but are not limited to LUDI (Bohm 1992) and LeapFrog (Tripos Inc., St. Louis Mo.).

In addition, baboon TAFI is overall well suited to modern methods including combinatorial chemistry.

Programs such as DOCK (Kuntz et al. 1982) can be used with the atomic coordinates from the homology model to identify potential ligands from databases or virtual databases which potentially bind the in the active site binding region which may therefore be suitable candidates for synthesis and testing.

Additionally, the three-dimensional homology model of baboon TAFI will aid in the design of mutants with altered biological activity.

Three-Dimensional Structure of Human TAFI

The three-dimensional structure represented in the homology model of human TAFI (see FIG. 10) is defined by a set of structure coordinates as set forth in Table II.

The complete amino acid sequence of human TAFI is shown is FIG. 9 (SEQ ID NO:17) with the catalytic domain in boldface. The first 23 residues which are italicized comprise the signal peptide preceding the TAFI expressed protein, the next 91 residues, shown underlined, make up the activation domain which gets cleaved off by thrombin prior to activation, and the next 309 residues, appearing in boldface, comprise the TAFI catalytic domain. The model only comprises the human TAFI catalytic domain (residues 115 to 443 of SEQ ID NO:17), and does not include the first 114 residues (those residues that are not in boldface) will not be considered further in the discussion that follows below. The 309 residues which form the catalytic domain, will henceforth be referred to as residues 1–309. This convention is also the basis for the numbering of residue names in Table II for the human TAFI model atom coordinates.

The term "structure coordinates" refers to Cartesian coordinates generated from the building of a homology model. In this invention, the homology model of residues 1 to 309 of human TAFI was derived by first carrying out a sequence similarity search for a suitable homolog using PSI-BLAST (Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402.) on the database of PDB structures. The two most significant hits, as judged both by the lowest E-scores (Karlin, S. & Altschul, S. F. (1990) "Methods for assessing the statistical significance of molecular sequence features by using general scoring schemes." Proc. Natl. Acad. Sci. USA 87:2264–2268 ; Dembo, A., Karlin, S. & Zeitouni, O. (1994) "Limit distribution of maximal non-aligned two-sequence segmental score." Ann. Prob. 22:2022–2039) and sequence identities (45%), were reported as 1KWM (Genbank Accession No.gi|21465928; SEQ ID NO:20), the PDB structure of human pancreatic procarboxypeptidase B [Pereira, P. J. B., Segura-Martin, S., Oliva, B., Ferrer-Orta, C., Aviles, F.-X., Coll, M., Gomis-Rueth, F.-X., Vendrell, J.: Human Procarboxypeptidase B: Three-Dimensional Structure and Implications for Thrombin-Activatable Fibrinolysis Inhibitor (Tafi) J.Mol.Biol. 321 pp. 537 (2002)], and 6CPA (Genbank Accession No.gi|231202; SEQ ID NO:19), the PDB structure of bovine pancreatic carboxypeptidase A [Kim, H., Lipscomb, W. N.: Crystal structure of the complex of carboxypeptidase A with a strongly bound phosphonate in a new crystalline form: comparison with structures of other complexes. Biochemistry 29 pp. 5546 (1990)].

The multiple sequence alignment corresponding to these hits is shown in FIG. 9 and was used as the template for the homology model. Because of the relatively high E-score and sequence identity, and in particular the fact that the residues defining the catalytic site were preserved (see FIG. 9), it was deemed unnecessary to attempt using more sophisticated sequence alignment methods (such as threading) for producing sequence alignments.

Using the sequence alignment shown in FIG. 9, the COMPOSER module from the SYBYL program (version 6.7; Tripos Inc., St. Louis, Mo.) was used to build the homology model consisting of complete backbone and side-chain conformations. The insertions in the human TAFI sequence relative to its homologs consisted of no more than one residue and were away from the active site. The final model was optimized by relaxing the structure using an energy-minimization protocol in SYBYL (version 6.7; Tripos Inc., St. Louis, Mo.). The backbone atoms were held fixed while the sidechain atoms were relaxed in order to minimize the unfavorable interactions arising from steric bumps. In this initial refinement protocol, electrostatic effects were ignored.

Figure 11:
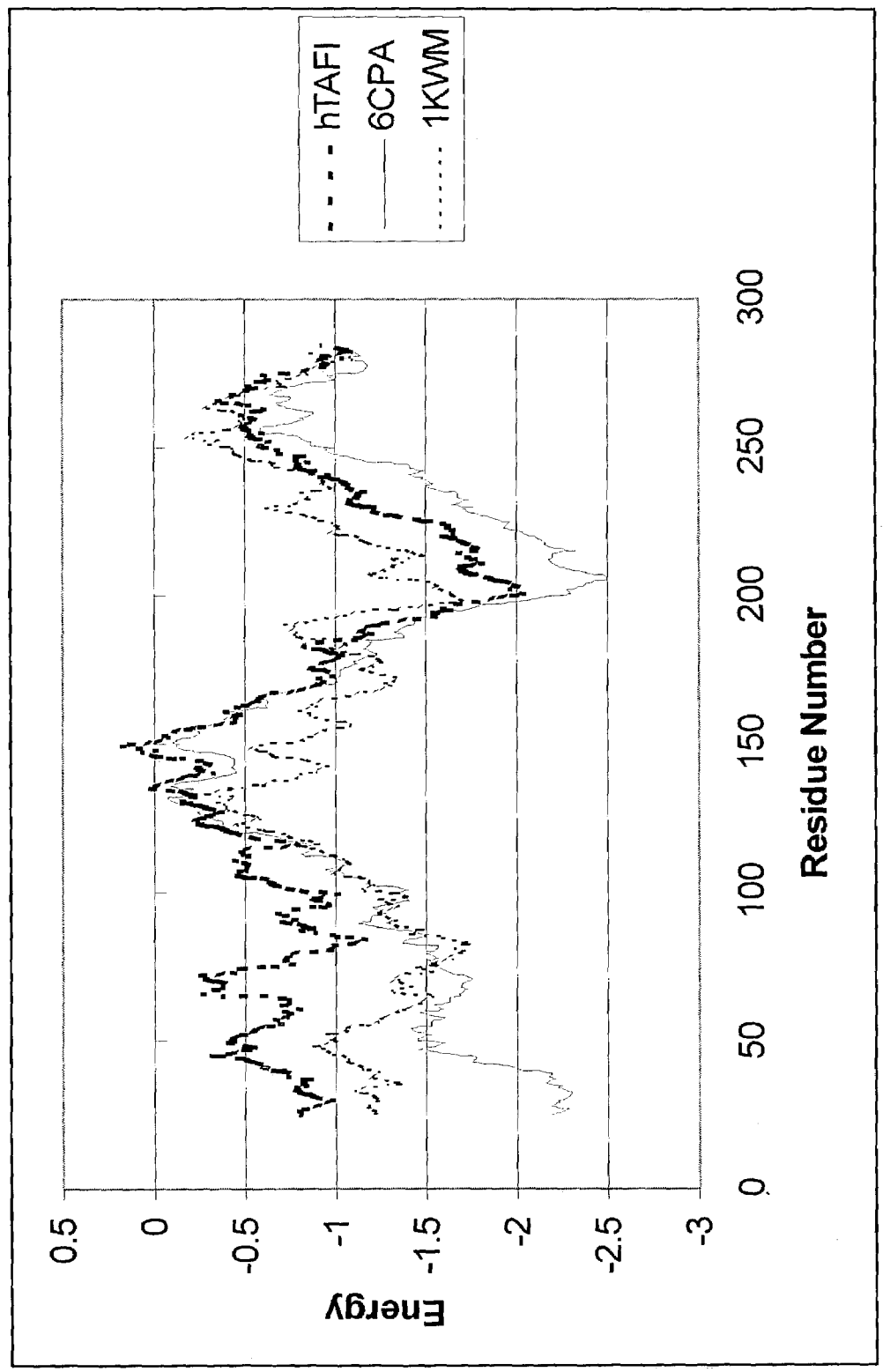
FIG. 11. Comparative variation of energy as a function of residue position in the sequence for the three proteins, human TAFI polypeptide (SEQ ID NO:17), bovine carboxypeptidase A (6CPA; Genbank Accession No.gi|231202; SEQ ID NO:19), and baboon procarboxypeptidase B (1KWM; Genbank Accession No.; SEQ ID NO:20). The PROSAII program from Proceryon was used for calculating the energies as described herein.

The structure quality of the model, thusly refined, was assessed in two ways. First, the SYBYL program ProTable (Tripos Inc., St. Louis, Mo.) was used to verify that in the final model, (i) there were no bad contacts, and (ii) the dihedral angles defining the backbone geometry had reasonable values consistent with known (($\phi$, $\psi$) distributions in proteins. Secondly, the PROSA program (Proceryon Biosciences Inc., New York, N.Y.) was used to calculate the energy distributions of residues in the model relative to those in the template they were built from (FIG. 11). This was done by threading each sequence through its structure and calculating the threading energies at each residue position. In order to smooth severe erratic behavior in the data, the data points were averaged over a 50-residue window. That is, each data point shown in Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates and/or using different methods in generating the homology model, will have minor effects on the overall shape. Variations in coordinates may also be generated because of mathematical manipulations of the structure Table II coordinates. For example, the structure coordinates set forth in could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of human TAFI described above as to be considered the same. Such analyses may be carried out in current software applications, such as SYBYL version 6.7/6.8 or INSIGHTII (Molecular Simulations Inc., San Diego, Calif.) version 2000 and as described in the accompanying User's Guides.

Using the superimposition tool in the program SYBYL comparisons can be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within SYBYL is defined by user input, for the purpose of this invention we will define equivalent atoms as protein backbone atoms (N, C$\alpha$, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by SYBYL.

For the purpose of this invention, any homology model of human TAFI that has a root mean square deviation of conserved residue backbone atoms (N, Cα, C, O) of less than about 0.25 Å when superimposed on the corresponding backbone atoms described by structure coordinates listed in Table II are considered identical. More preferably, the root mean square deviation is less than about 0.1 Å.

In another embodiment of this invention, structural models wherein backbone atoms have been substituted with other elements which when superimposed on the corresponding backbone atoms have low root mean square deviations are considered to be identical.

For example, an homology model where the original backbone carbon, and/or nitrogen and/or oxygen atoms are replaced with other elements having a root mean square deviation of about 0.25 angstroms when superimposed on the corresponding backbone atoms described by structure coordinates listed in Table II is considered identical. More preferably, the root mean square deviation is less than about 0.1 Å.

This invention as embodied by the homology model enables the structure-based design of modulators of the biological function of human TAFI, as well as mutants with altered biological function and/or specificity.

For purposes of the present invention, the active site region specifies the amino acids D63-P74, V109-N110, R122-N127, T139-F145, G154, E162-Y164, Y192-V203, S207, L248-D256, F268-D274, G279-F280, Zn whose structure coordinates appear in Table II, or analogue of said molecule involving simple truncations and/or mutations of amino acids, or in which the original C,N, and O atoms in said molecule are replaced with other elements.

In a preferred embodiment of the present invention, the molecule comprises at least a portion of the active site region defined by structure coordinates of human TAFI amino acids D63-P74, V109-N110, R122-N127, T139-F145, G154, E162-Y164, Y192-V203, S207, L248-D256, F268-D274, G279-F280, Zn according to Table II, or analogue of said molecule involving simple truncations and/or mutations of amino acids, or replacement in said molecule of the original C, N, and O atoms with other elements.

For purposes of the present invention, by "at least a portion of" it is meant all or any parts of the active site region defined by these structure coordinates according to Table II. More preferred are molecules comprising all or any parts of the active site region, according to Table II, or a mutant or homologue or analogue of said molecule or molecular complex. By mutant or homologue of the molecule it is meant a molecule that has a root mean square deviation from the backbone atoms of said human TAFI amino acids of not more than about 0.25 Angstroms.

By analogue is meant any structure involving simple substitution of the original backbone atoms with other elements such that the root mean square deviation from the backbone atoms of said human TAFI is not more than about 0.1 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of the human TAFI portion of the complex as defined by the structure coordinates described herein.

The structure coordinates of a human TAFI homology model or portions thereof are stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table II.

For the first time, the present invention permits the use of structure-based or rational drug design techniques to design, select, and synthesize chemical entities that are capable of modulating the biological function of human TAFI.

Accordingly, the present invention is also directed to the active site binding region in human TAFI, on the basis of which a small molecule may be designed to bind to at least part of the region defined by the amino D63-P74, V109-N110, R122-N127, T139-F145, G154, E162-Y164, Y192-V203, S207, L248-D256, F268-D274, G279-F280, Zn or some portion thereof, according to Table II. By active site binding region, it is also meant to include mutants or homologues thereof, or transformations involving simple substitution of the original C, N, and O atoms with other elements. In a preferred embodiment, the mutants or homologues have at least 25% identity, more preferably 50% identity, more preferably 75% identity, and most preferably 90% identity D63-P74, V109-N110, R122-N127, T139-F145, G154, E162-Y164, Y192-V203, S207, L248-D256, F268-D274, G279-F280, Zn according to Table II.

The three-dimensional model structure of the human TAFI will also provide methods for identifying modulators of biological function. Various methods or combination thereof can be used to identify these compounds.

For example, test compounds can be modeled that fit spatially into the active site region in human TAFI embodied in the sequence D63-P74, V109-N110, R122-N127, T139-F145, G154, E162-Y164, Y192-V203, S207, L248-D256, F268-D274, G279-F280, Zn or some portion thereof, according to Table II.

Structure coordinates of the active site binding region in human TAFI defined by the amino acids D63-P74, V109-N110, R122-N127, T139-F145, G154, E162-Y164, Y192-V203, S207, L248-D256, F268-D274, G279-F280, Zn can also be used to identify structural and chemical features. Identified structural or chemical features can then be employed to design or select compounds as potential human TAFI ligands. By structural and chemical features it is meant to include, but is not limited to, covalent bonding, van der Waals interactions, hydrogen bonding interactions, charge interaction, hydrophobic bonding interaction, and dipole interaction. Alternatively, or in conjunction, the three-dimensional structural model can be employed to design or select compounds as potential human TAFI ligands. Compounds identified as potential human TAFI ligands can then be synthesized and screened in an assay characterized by binding of a test compound to the human TAFI, or in characterizing the ability of human TAFI to modulate a protease target in the presence of a small molecule. Examples of assays useful in screening of potential human TAFI ligands include, but are not limited to, screening in silico, in vitro assays and high throughput assays. Finally, these methods may also involve modifying or replacing one or more amino acids D63-P74, V109-N110, R122-N127, T139-F145, G154, E162-Y164, Y192-V203, S207, L248-D256, F268-D274, G279-F280, Zn from human TAFI according to Table II.

However, as will be understood by those of skill in the art upon this disclosure, other structure-based design methods can be used. Various computational structure-based design methods have been disclosed in the art.

For example, a number of computer modeling systems are available in which the sequence of the human TAFI and the human TAFI structure (i.e., atomic coordinates of human TAFI and/or the atomic coordinates of the active site region as provided in Table II) can be input. This computer system then generates the structural details of one or more these regions in which a potential human TAFI modulator binds so that complementary structural details of the potential modulators can be determined. Design in these modeling systems is generally based upon the compound being capable of physically and structurally associating with human TAFI. In addition, the compound must be able to assume a conformation that allows it to associate with human TAFI. Some modeling systems estimate the potential inhibitory or binding effect of a potential human TAFI modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in one or more of the cleaved reactive loop binding region, the heparin binding region, or the reactive loop in human TAFI. Docking is accomplished using software such as INSIGHTII, QUANTA and SYBYL, following by energy minimization and molecular dynamics with standard molecular mechanic force fields such as, MMFF, CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and human TAFI can be visualized and then assembled into a single potential modulator. Programs useful in assembling the individual chemical entities include, but are not limited to CAVEAT (Bartlett et al. 1989) and 3D Database systems (Martin 1992).

Alternatively, compounds may be designed de novo using either an empty active site or optionally including some portion of a known inhibitor. Methods of this type of design include, but are not limited to LUDI (Bohm 1992) and LeapFrog (Tripos Inc., St. Louis Mo.). In addition, human TAFI is overall well suited to modern methods including combinatorial chemistry.

Programs such as DOCK (Kuntz et al. 1982) can be used with the atomic coordinates from the homology model to identify potential ligands from databases or virtual databases which potentially bind the in the active site binding region which may therefore be suitable candidates for synthesis and testing.

Additionally, the three-dimensional homology model of human TAFI will aid in the design of mutants with altered biological activity.

Comparison Between Baboon and Human TAFI Three Dimensional Homology Models

An alignment of the polypeptide sequence of the baboon TAFI polypeptide of the present invention (SEQ ID NO:2) with the human TAFI (SEQ ID NO:17) is provided in FIG. 8. As discussed elsewhere herein, the baboon TAFI polypeptide shares 94.3% sequence identity with the human TAFI based upon the CLUSTALW algorithm using default parameters.

As a result of the high percent identity, all residues lying within 12 Å of the Zn atom in the binding site, namely D63-P74, V109-N110, R122-N127, T139-F145, G154, E162-Y164, Y192-V203, S207, L248-D256, F268-D274, G279-F280 (residue numbering counting from the first residue in the ligand-binding domain of baboon TAFI with residue 1 representing residue 115 of SEQ ID NO:2 and 17), are conserved in human TAFI.

Figure 12:
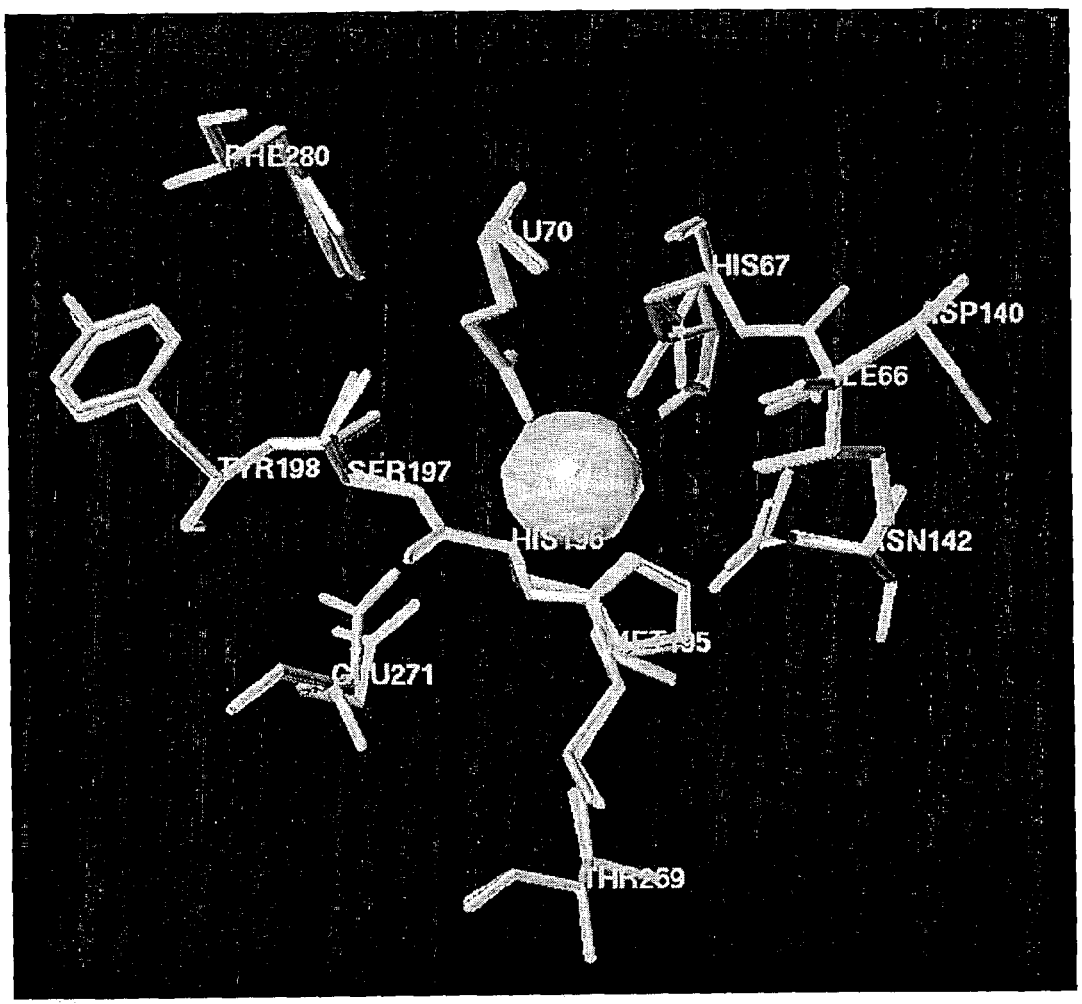
FIG. 12. Overlay of human and baboon TAFI models of the present invention in the 7 Å region around the Zn atom (centrally located ball). The overlapping residues are identical in the two cases, but the orientations of some sidechains (for example His67, Glu271) are somewhat different because of slight differences in packing.

Using a multiple-sequence alignment of human TAFI with the 6CPA and 1KMW structural templates, as performed for the baboon TAFI model, a three-dimensional homology model of human TAFI shows that the active sites of both the human and baboon TAFI polypeptides are very similar. An overlay of residues lying within 7 Å of the Zn ion is shown in FIG. 12.

Deposit of Microorganisms

The following microorganism was deposited with the American Type Culture Collection (ATCC), Rockville, Md., on Dec. 22, 2001 and assigned the indicated accession number:

| Microorganism | ATCC Accession No. |
| --- | --- |
| bTAFI in pFastBacl expression plasmid | PTA 3949 |

REFERENCES

Bartlett et al. Molecular Recognition in Chemical and Biological Problems Special Publication, Royal Chem. Soc. 78:182–196 (1989).

Bode, Wolfram; Brandstetter, Hans; Mather, Timothy; Stubbs, Milton T. Comparative analysis of hemostatic proteinases. Structural aspects of thrombin, factor Xa, factor IXa, and protein C. Thromb. Haemostasis (1997), 78(1), 501–511

Bohm H-J, LUDI: rule-based automatic design of new substituents for enzyme inhibitor leads. J. Comp. Aid. Molec. Design 6:61–78 (1992)

Cardozo T; Totrov M; Abagyan R Homology modeling by the ICM method. Proteins 23:403–14 (1995).

Czapinska, Honorata; Otlewski, Jacek. Structural and energetic determinants of the S1-site specificity in serine proteases. European Journal of Biochemistry (1999), 260 (3), 571–595

Goodford, P. J. A computational procedure for determining energetically favorable binding sites on biologically important macromolecules. J. Med. Chem. 28:849–857 (1985)

Goodsell, D. S. and Olsen, A. J. Automated docking of substrates to proteins by simulated annealing. Proteins 8:195–202 (1990)

Greer J Comparative modeling of homologous proteins. Methods Enzymol 202:239–52 (1991).
Hendlich M; Lackner P; Weitckus S; Floeckner H; Froschauer R; Gottsbacher K; Casari G; Sippl M J Identification of native protein folds amongst a large number of incorrect models. The calculation of low energy conformations from potentials of mean force. J. Mol. Biol. 216:167–80 (1990).
Katz, Bradley A.; Sprengeler, Paul A.; Luong, Christine; Verner, Erik; Elrod, Kyle; Kirtley, Matt; Janc, James; Spencer, Jeffrey R.; Breitenbucher, J. Guy; Hui, Hon; McGee, Danny; Allen, Darin; Martelli, Arnold; Mackman, Richard L. Engineering inhibitors highly selective for the S1 sites of Ser190 trypsin-like serine protease drug targets. Chemistry & Biology (2001), 8(11), 1107–1121
Kuntz I D, Blaney J M, Oatley S J, Langridge R, Ferrin T E. A geometric approach to macromolecule-ligand interactions. J. Mol. Biol. 161:269–288 (1982)
Lee et al., Proc. Natl. Acad. Sci. USA, 88:7233–7237, 1991;
Lesk, A. M., Boswell, D. R., Homology Modeling: Inferences from Tables of Aligned Sequences. Curr. Op. Struc. Biol. 2:242–247 (1992)
Martin, Y. C. 3D database searching in drug design. J. Med. Chem. 35:2145–2154 (1992)
Renatus, Martin; Bode, Wolfram; Huber, Robert; Stuerzebecher, Joerg; Stubbs, Milton T. Structural and Functional Analyses of Benzamidine-Based Inhibitors in Complex with Trypsin: Implications for the Inhibition of Factor Xa, tPA, and Urokinase. Journal of Medicinal Chemistry (1998), 41(27), 5445–5456
Sali A; Potterton L; Yuan F; van Vlijmen H; Karplus M Evaluation of comparative protein modeling by MODELLER. PROTEINS 23:318–26 (1995).
Schechter and Berger, Biochemical and Biophysical Research Communications (1967), 27(2), 157–62

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated nucleic acid molecule comprising a polynucleotide sequence selected from the group consisting of:
   (a) an isolated polynucleotide encoding a polypeptide comprising amino acids 1 to 423 of SEQ ID NO:2;
   (b) an isolated polynucleotide encoding a polypeptide comprising amino acids 2 to 423 of SEQ ID NO:2; and
   (c) an isolated polynucleotide encoding a polypeptide comprising amino acids 23 to 423 of SEQ ID NO:2.

2. The isolated nucleic acid molecule of claim 1, wherein said polynucleotide is (a).

3. The isolated nucleic acid molecule of claim 2, wherein said polynucleotide comprises of nucleotides 1 to 1269 of SEQ ID NO:1.

4. The isolated nucleic acid molecule of claim 1, wherein said polynucleotide is (b).

5. The isolated nucleic acid molecule of claim 4, wherein said polynucleotide comprises nucleotides 4 to 1269 of SEQ ID NO: 1.

6. The isolated nucleic acid molecule of claim 1, wherein said polynucleotide is (c).

7. The isolated nucleic acid molecule of claim 6, wherein said polynucleotide comprises nucleotides 67 to 1269 of SEQ ID NO: 1.

8. An isolated nucleic acid molecule comprising a polynucleotide having a nucleotide sequence that is at least 96.3% identical to a polynucleotide sequence provided in claim 3, 5, or 7, wherein percent identity is calculated using a CLUSTALW global sequence alignment using default parameters, and wherein said polynucleotide encodes a polypeptide that has thrombin-activatable fibrinolysis inhibitor activity.

9. A recombinant vector comprising the isolated nucleic acid molecule of claim 1.

10. An isolated recombinant host cell comprising the recombinant vector of claim 9.

11. A method of making an isolated polypeptide comprising:
   (a) culturing the isolated recombinant host cell of claim 10 under conditions such that said polypeptide is expressed; and
   (b) recovering said polypeptide.

12. The isolated polynucleotide of claim 1 wherein said nucleic acid sequence further comprises a heterologous nucleic acid sequence.

13. The isolated polynucleotide of claim 12 wherein said heterologous nucleic acid sequence encodes a heterologous polypeptide.

14. An isolated polynucleotide which represents the complementary sequence of (a), (b), or (c) of claim 1.

15. The isolated nucleic acid molecule of claim 14, wherein said polynucleotide comprises nucleotides 67 to 342 of SEQ ID NO: 1.

16. The isolated nucleic acid molecule of claim 14, wherein said polynucleotide comprises nucleotides 343 to 1269 of SEQ ID NO:1.

17. An isolated nucleic acid molecule comprising a polynucleotide encoding a polypeptide that it as least 94.4% identical to amino acids 2 to 423 of SEQ ID NO:2, wherein percent identity is calculated using a CLUSTALW global sequence alignment using default parameters, and wherein said polynucleotide encodes a polypeptide that has thrombin-activatable fibrinolysis inhibitor activity.

18. An isolated polynucleotide encoding a polypeptide comprising at least 401 contiguous amino acids of SEQ ID NO:2, wherein said polypeptide has thrombin-activatable fibrinolysis inhibitor activity.

19. The isolated nucleic acid molecule of claim 18, wherein said polynucleotide comprises at least 1203 contiguous nucleotides of SEQ ID NO:1.

20. An isolated polynucleotide comprising a polynucleotide encoding amino acids 2 to 423 of the polypeptide provided as SEQ ID NO:2 comprising at least one amino acid substitution at amino acid residues 181, 184, and 310, wherein said polypeptide has thrombin-activatable fibrinolysis inhibitor activity, or is catalytically inactive yet retains ability to bind to thrombin.

21. An isolated polynucleotide encoding a polypeptide comprising amino acids 23 to 114 of SEQ ID NO:2.

22. An isolated polynucleotide encoding a polypeptide comprising amino acids 115 to 423 of SEQ ID NO:2.

23. An isolated nucleic acid molecule comprising the cDNA clone contained in plasmid btafi in ATCC Deposit No. PTA-3949.

* * * * *

UNITED STATES PATENT AND TRADEMARK OFFICE
CERTIFICATE OF CORRECTION

| | | |
|---|---|---|
| PATENT NO. | : 7,091,331 B2 | Page 1 of 1 |
| APPLICATION NO. | : 10/379836 | |
| DATED | : August 15, 2006 | |
| INVENTOR(S) | : James K. Tamura et al. | |

It is certified that error appears in the above-identified patent and that said Letters Patent is hereby corrected as shown below:

On Title page
Item 75:

Delete "Akbar Nayeem"

Column 95, Line 52

Claim 3 - delete "of" after "comprises"

Signed and Sealed this

Seventeenth Day of April, 2007

JON W. DUDAS
*Director of the United States Patent and Trademark Office*

SEQUENCE LISTING

<160> NUMBER OF SEQ ID NOS: 24

<210> SEQ ID NO 1
<211> LENGTH: 1272
<212> TYPE: DNA
<213> ORGANISM: Papio hamadryas
<220> FEATURE:
<221> NAME/KEY: CDS
<222> LOCATION: (1)..(1269)

<400> SEQUENCE: 1

```
atg aag ctt tgc agt ctt gca gtc ctt gta ccc att gtt ctc ttc tgt      48
Met Lys Leu Cys Ser Leu Ala Val Leu Val Pro Ile Val Leu Phe Cys
1               5                   10                  15 gag cag cat gtc ttc gcg ttt cag agt ggc cag gtt cta gct gct ctt      96
Glu Gln His Val Phe Ala Phe Gln Ser Gly Gln Val Leu Ala Ala Leu
                20                  25                  30 cct aga acc tct agg caa gtt caa gtg cta cag aat ctt act aca aca     144
Pro Arg Thr Ser Arg Gln Val Gln Val Leu Gln Asn Leu Thr Thr Thr
            35                  40                  45 tat gag att gtt ctc tgg cag ccg gta aca gcg gac ctt att gag aag     192
Tyr Glu Ile Val Leu Trp Gln Pro Val Thr Ala Asp Leu Ile Glu Lys
        50                  55                  60 aaa aaa caa gtc cat ttt ttt gta aat tca tct gat gtc gac aat gtg     240
Lys Lys Gln Val His Phe Phe Val Asn Ser Ser Asp Val Asp Asn Val
65                  70                  75                  80 aaa gcc cat tta aat gtg agc gga att cca tgc agt gtc ctg ctg gca     288
Lys Ala His Leu Asn Val Ser Gly Ile Pro Cys Ser Val Leu Leu Ala
                85                  90                  95 gat gtg gaa gat ctt att caa cag cag att tcc aac gac aca gtc agc     336
Asp Val Glu Asp Leu Ile Gln Gln Gln Ile Ser Asn Asp Thr Val Ser
                100                 105                 110 ccc cga gcc tcc gca tcg tac tat gaa cag tat cac tca cta aat gaa     384
```

-continued

```
                Pro Arg Ala Ser Ala Ser Tyr Tyr Glu Gln Tyr His Ser Leu Asn Glu
                        115                 120                 125 atc tat tct tgg ata gaa ctt ata act gag aag tat cct gat atg ctt          432
Ile Tyr Ser Trp Ile Glu Leu Ile Thr Glu Lys Tyr Pro Asp Met Leu
130                 135                 140 aca aaa atc cac att gga tcc tcc tat gag aag cac cca ctt tat gtt          480
Thr Lys Ile His Ile Gly Ser Ser Tyr Glu Lys His Pro Leu Tyr Val
145                 150                 155                 160 tta aag gtt tct gga aaa gaa caa aca gcc aaa aat gcc atg tgg att          528
Leu Lys Val Ser Gly Lys Glu Gln Thr Ala Lys Asn Ala Met Trp Ile
                165                 170                 175 gac tgt gga atc cat gcc aga gaa tgg atc tcc cct gct ttc tgc ttg          576
Asp Cys Gly Ile His Ala Arg Glu Trp Ile Ser Pro Ala Phe Cys Leu
            180                 185                 190 tgg ttc ata ggc cat ata act gaa tac tac ggg ata ata ggg gaa tat          624
Trp Phe Ile Gly His Ile Thr Glu Tyr Tyr Gly Ile Ile Gly Glu Tyr
        195                 200                 205 acc aat ctt ctg agg cat gtg gat ttc tat gtt atg cca gtg gtt aat          672
Thr Asn Leu Leu Arg His Val Asp Phe Tyr Val Met Pro Val Val Asn
    210                 215                 220 gtg gat ggt tat gac tac tca tgg aaa aag aat cga atg tgg aga aag          720
Val Asp Gly Tyr Asp Tyr Ser Trp Lys Lys Asn Arg Met Trp Arg Lys
225                 230                 235                 240 aac cgt tct ttc tat gcg aac aat cgt tgc atc gga aca gac ctg aac          768
Asn Arg Ser Phe Tyr Ala Asn Asn Arg Cys Ile Gly Thr Asp Leu Asn
                245                 250                 255 agg aac ttt gcg tcc aaa cac tgg tgt gag gaa ggt gca tcc agt ttc          816
Arg Asn Phe Ala Ser Lys His Trp Cys Glu Glu Gly Ala Ser Ser Phe
            260                 265                 270 tca tgc tcg gaa acc tac tgt gga ctt tat cct gag tca gaa cca gaa          864
Ser Cys Ser Glu Thr Tyr Cys Gly Leu Tyr Pro Glu Ser Glu Pro Glu
        275                 280                 285 gcg aag gcg gtg gct aat ttc ttg aga aga aat atc aac cac att aaa          912
Ala Lys Ala Val Ala Asn Phe Leu Arg Arg Asn Ile Asn His Ile Lys
    290                 295                 300 gca tac atc agc atg cat tca tac tcc cag cat atc gtg ttt cca tat          960
Ala Tyr Ile Ser Met His Ser Tyr Ser Gln His Ile Val Phe Pro Tyr
305                 310                 315                 320 tcc tat act cga agc aaa agc aaa gac cac gag gaa ttg tct cta gta         1008
Ser Tyr Thr Arg Ser Lys Ser Lys Asp His Glu Glu Leu Ser Leu Val
                325                 330                 335 gcc agt gaa gca gtt cgt gct att cag aaa acc agt aaa aat atc agg         1056
Ala Ser Glu Ala Val Arg Ala Ile Gln Lys Thr Ser Lys Asn Ile Arg
            340                 345                 350 tat aca cat ggc cgt ggc tca gaa acc tta tac cta gct cct gga ggt         1104
Tyr Thr His Gly Arg Gly Ser Glu Thr Leu Tyr Leu Ala Pro Gly Gly
        355                 360                 365 gcg gac gat tgg atc tat gat ttg ggc atc aaa tat tcg ttt aca att         1152
Ala Asp Asp Trp Ile Tyr Asp Leu Gly Ile Lys Tyr Ser Phe Thr Ile
    370                 375                 380 gaa ctt cga gat acg ggc aaa tac gga ttc ttg ctg cct gag cgt tac         1200
Glu Leu Arg Asp Thr Gly Lys Tyr Gly Phe Leu Leu Pro Glu Arg Tyr
385                 390                 395                 400 atc aaa ccc act tgt aaa gac gct ttt gcc gct gtc tct aaa ata gct         1248
Ile Lys Pro Thr Cys Lys Asp Ala Phe Ala Ala Val Ser Lys Ile Ala
                405                 410                 415 tgg cat gtc att agg aat gtt taa                                         1272
Trp His Val Ile Arg Asn Val
            420
```

```
<210> SEQ ID NO 2
<211> LENGTH: 423
<212> TYPE: PRT
<213> ORGANISM: Papio hamadryas

<400> SEQUENCE: 2

Met Lys Leu Cys Ser Leu Ala Val Leu Val Pro Ile Val Leu Phe Cys
1               5                   10                  15

Glu Gln His Val Phe Ala Phe Gln Ser Gly Gln Val Leu Ala Ala Leu
                20                  25                  30

Pro Arg Thr Ser Arg Gln Val Gln Val Leu Gln Asn Leu Thr Thr Thr
            35                  40                  45

Tyr Glu Ile Val Leu Trp Gln Pro Val Thr Ala Asp Leu Ile Glu Lys
        50                  55                  60

Lys Lys Gln Val His Phe Phe Val Asn Ser Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Leu Ile Thr Glu Lys Tyr Pro Asp Met Leu
        130                 135                 140

Thr Lys Ile His Ile Gly Ser Ser Tyr Glu Lys His Pro Leu Tyr Val
145                 150                 155                 160

Leu Lys Val Ser Gly Lys Glu Gln Thr Ala Lys Asn Ala Met Trp Ile
                165                 170                 175

Asp Cys Gly Ile His Ala Arg Glu Trp Ile Ser Pro Ala Phe Cys Leu
            180                 185                 190

Trp Phe Ile Gly His Ile Thr Glu Tyr Tyr Gly Ile Ile Gly Glu Tyr
        195                 200                 205

Thr Asn Leu Leu Arg His Val Asp Phe Tyr Val Met Pro Val Val Asn
        210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn Arg Cys Ile Gly Thr Asp Leu Asn
                245                 250                 255

Arg Asn Phe Ala Ser Lys His Trp Cys Glu Glu Gly Ala Ser Ser Phe
            260                 265                 270

Ser Cys Ser Glu Thr Tyr Cys Gly Leu Tyr Pro Glu Ser Glu Pro Glu
        275                 280                 285

Ala Lys Ala Val Ala Asn Phe Leu Arg Arg Asn Ile Asn His Ile Lys
        290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
                325                 330                 335

Ala Ser Glu Ala Val Arg Ala Ile Gln Lys Thr Ser Lys Asn Ile Arg
            340                 345                 350

Tyr Thr His Gly Arg Gly Ser Glu Thr Leu Tyr Leu Ala Pro Gly Gly
        355                 360                 365

Ala Asp Asp Trp Ile Tyr Asp Leu Gly Ile Lys Tyr Ser Phe Thr Ile
370                 375                 380
```

```
Glu Leu Arg Asp Thr Gly Lys Tyr Gly Phe Leu Leu Pro Glu Arg Tyr
385                 390                 395                 400

Ile Lys Pro Thr Cys Lys Asp Ala Phe Ala Ala Val Ser Lys Ile Ala
                405                 410                 415

Trp His Val Ile Arg Asn Val
            420

<210> SEQ ID NO 3
<211> LENGTH: 18
<212> TYPE: DNA
<213> ORGANISM: Homo sapiens

<400> SEQUENCE: 3
agaaccagaa gtgaaggc                                                 18

<210> SEQ ID NO 4
<211> LENGTH: 26
<212> TYPE: DNA
<213> ORGANISM: Mus musculus

<400> SEQUENCE: 4
gtaaacgaat atttgatgcc caaatc                                        26

<210> SEQ ID NO 5
<211> LENGTH: 33
<212> TYPE: DNA
<213> ORGANISM: Mus musculus

<400> SEQUENCE: 5
ccatgccaga gaatggattt cacctgcttt ctg                                33

<210> SEQ ID NO 6
<211> LENGTH: 26
<212> TYPE: DNA
<213> ORGANISM: Papio hamadryas

<400> SEQUENCE: 6
agtatgaatg catgctgatg tatgct                                        26

<210> SEQ ID NO 7
<211> LENGTH: 26
<212> TYPE: DNA
<213> ORGANISM: Papio hamadryas

<400> SEQUENCE: 7
tcagaaacct tatacctagc tcctgg                                        26

<210> SEQ ID NO 8
<211> LENGTH: 21
<212> TYPE: DNA
<213> ORGANISM: Homo sapiens

<400> SEQUENCE: 8
ttgctggaat cagtaaatta a                                             21

<210> SEQ ID NO 9
<211> LENGTH: 17
<212> TYPE: DNA
<213> ORGANISM: Homo sapiens

<400> SEQUENCE: 9
ctgttgggat gaagctt                                                  17
```

<210> SEQ ID NO 10
<211> LENGTH: 25
<212> TYPE: DNA
<213> ORGANISM: Papio hamadryas

<400> SEQUENCE: 10
tattatcccg tagtattcag ttata                                  25

<210> SEQ ID NO 11
<211> LENGTH: 28
<212> TYPE: DNA
<213> ORGANISM: Papio hamadryas

<400> SEQUENCE: 11
ggtaccatga agctttgcag tcttgcag                               28

<210> SEQ ID NO 12
<211> LENGTH: 23
<212> TYPE: DNA
<213> ORGANISM: Papio hamadryas

<400> SEQUENCE: 12
ctcataggag gatccaatgt gga                                    23

<210> SEQ ID NO 13
<211> LENGTH: 23
<212> TYPE: DNA
<213> ORGANISM: Papio hamadryas

<400> SEQUENCE: 13
aatccacatt ggatcctcct atg                                    23

<210> SEQ ID NO 14
<211> LENGTH: 23
<212> TYPE: DNA
<213> ORGANISM: Papio hamadryas

<400> SEQUENCE: 14
aagcatacat cagcatgcat tca                                    23

<210> SEQ ID NO 15
<211> LENGTH: 28
<212> TYPE: DNA
<213> ORGANISM: Papio hamadryas

<400> SEQUENCE: 15
gatatcttaa acattcctaa tgcatgcc                               28

<210> SEQ ID NO 16
<211> LENGTH: 422
<212> TYPE: PRT
<213> ORGANISM: Rattus norvegicus

<400> SEQUENCE: 16

Met Lys Leu Tyr Gly Leu Gly Val Leu Val Ala Ile Ile Leu Tyr Glu
1               5                   10                  15

Lys His Gly Leu Ala Phe Gln Ser Gly His Val Leu Ser Ala Leu Pro
            20                  25                  30

Arg Thr Ser Arg Gln Val Gln Leu Leu Gln Asn Leu Thr Thr Thr Tyr
        35                  40                  45

Glu Val Val Leu Trp Gln Pro Val Thr Ala Glu Phe Ile Glu Lys Lys

```
                50                  55                  60
Lys Glu Val His Phe Val Asn Ala Ser Asp Val Asn Ser Val Lys
 65                  70                  75                  80

Ala Tyr Leu Asn Ala Ser Arg Ile Pro Phe Asn Val Leu Met Asn Asn
                 85                  90                  95

Val Glu Asp Leu Ile Gln Gln Thr Ser Asn Asp Thr Val Ser Pro
            100                 105                 110

Arg Ala Ser Ser Tyr Tyr Glu Gln Tyr His Ser Leu Asn Glu Ile
            115                 120                 125

Tyr Ser Trp Ile Glu Val Ile Thr Glu Gln His Pro Asp Met Leu Gln
130                 135                 140

Lys Ile Tyr Ile Gly Ser Ser Tyr Glu Lys Tyr Pro Leu Tyr Val Leu
145                 150                 155                 160

Lys Val Ser Gly Lys Glu His Arg Val Lys Asn Ala Ile Trp Ile Asp
                165                 170                 175

Cys Gly Ile His Ala Arg Glu Trp Ile Ser Pro Ala Phe Cys Leu Trp
            180                 185                 190

Phe Ile Gly Tyr Val Thr Gln Phe His Gly Lys Glu Asn Thr Tyr Thr
            195                 200                 205

Arg Leu Leu Arg His Val Asp Phe Tyr Ile Met Pro Val Met Asn Val
210                 215                 220

Asp Gly Tyr Asp Tyr Thr Trp Lys Lys Asn Arg Met Trp Arg Lys Asn
225                 230                 235                 240

Arg Ser Val His Met Asn Asn Arg Cys Val Gly Thr Asp Leu Asn Arg
                245                 250                 255

Asn Phe Ala Ser Lys His Trp Cys Glu Lys Gly Ala Ser Ser Phe Ser
            260                 265                 270

Cys Ser Glu Thr Tyr Cys Gly Leu Tyr Pro Glu Ser Glu Pro Glu Val
            275                 280                 285

Lys Ala Val Ala Asp Phe Leu Arg Arg Asn Ile Asn His Ile Lys Ala
            290                 295                 300

Tyr Ile Ser Met His Ser Tyr Ser Gln Gln Ile Leu Phe Pro Tyr Ser
305                 310                 315                 320

Tyr Asn Arg Ser Lys Ser Lys Asp His Glu Glu Leu Ser Leu Val Ala
                325                 330                 335

Ser Glu Ala Val Arg Ala Ile Glu Ser Ile Asn Lys Asn Thr Arg Tyr
            340                 345                 350

Thr His Gly Ser Gly Ser Glu Ser Leu Tyr Leu Ala Pro Gly Gly Ser
            355                 360                 365

Asp Asp Trp Ile Tyr Asp Leu Gly Ile Lys Tyr Ser Phe Thr Ile Glu
370                 375                 380

Leu Arg Asp Thr Gly Arg Tyr Gly Phe Leu Leu Pro Glu Arg Phe Ile
385                 390                 395                 400

Lys Pro Thr Cys Ala Glu Ala Leu Ala Val Ser Lys Ile Ala Trp
                405                 410                 415

His Val Ile Arg Asn Ser
            420

<210> SEQ ID NO 17
<211> LENGTH: 423
<212> TYPE: PRT
<213> ORGANISM: Homo sapiens

<400> SEQUENCE: 17
```

```
Met Lys Leu Cys Ser Leu Ala Val Leu Val Pro Ile Val Leu Phe Cys
1               5                   10                  15

Glu Gln His Val Phe Ala Phe Gln Ser Gly Gln Val Leu Ala Ala Leu
            20                  25                  30

Pro Arg Thr Ser Arg Gln Val Gln Val Leu Gln Asn Leu Thr Thr Thr
            35                  40                  45

Tyr Glu Ile Val Leu Trp Gln Pro Val Thr Ala Asp Leu Ile Val Lys
50                      55                  60

Lys Lys Gln Val His Phe Phe Val Asn Ala Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Gln Ile Ser Asn Asp Thr Val Ser
            100                 105                 110

Pro Arg Ala Ser Ala Ser Tyr Tyr Glu Gln Tyr His Ser Leu Asn Glu
            115                 120                 125

Ile Tyr Ser Trp Ile Glu Phe Ile Thr Glu Arg His Pro Asp Met Leu
130                     135                 140

Thr Lys Ile His Ile Gly Ser Ser Phe Glu Lys Tyr Pro Leu Tyr Val
145                 150                 155                 160

Leu Lys Val Ser Gly Lys Glu Gln Thr Ala Lys Asn Ala Ile Trp Ile
                165                 170                 175

Asp Cys Gly Ile His Ala Arg Glu Trp Ile Ser Pro Ala Phe Cys Leu
                180                 185                 190

Trp Phe Ile Gly His Ile Thr Gln Phe Tyr Gly Ile Ile Gly Gln Tyr
            195                 200                 205

Thr Asn Leu Leu Arg Leu Val Asp Phe Tyr Val Met Pro Val Val Asn
210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn His Cys Ile Gly Thr Asp Leu Asn
            245                 250                 255

Arg Asn Phe Ala Ser Lys His Trp Cys Glu Glu Gly Ala Ser Ser Ser
            260                 265                 270

Ser Cys Ser Glu Thr Tyr Cys Gly Leu Tyr Pro Glu Ser Glu Pro Glu
    275                 280                 285

Val Lys Ala Val Ala Ser Phe Leu Arg Arg Asn Ile Asn Gln Ile Lys
    290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
            325                 330                 335

Ala Ser Glu Ala Val Arg Ala Ile Glu Lys Thr Ser Lys Asn Thr Arg
            340                 345                 350

Tyr Thr His Gly His Gly Ser Glu Thr Leu Tyr Leu Ala Pro Gly Gly
            355                 360                 365

Gly Asp Asp Trp Ile Tyr Asp Leu Gly Ile Lys Tyr Ser Phe Thr Ile
            370                 375                 380

Glu Leu Arg Asp Thr Gly Thr Tyr Gly Phe Leu Leu Pro Glu Arg Tyr
385                 390                 395                 400

Ile Lys Pro Thr Cys Arg Glu Ala Phe Ala Ala Val Ser Lys Ile Ala
            405                 410                 415

Trp His Val Ile Arg Asn Val
```

<210> SEQ ID NO 18
<211> LENGTH: 422
<212> TYPE: PRT
<213> ORGANISM: Mus musculus

<400> SEQUENCE: 18

| Met | Lys | Leu | His | Gly | Leu | Gly | Ile | Leu | Val | Ala | Ile | Ile | Leu | Tyr | Glu |
|---|---|---|---|---|---|---|---|---|---|---|---|---|---|---|---|
| 1 | | | | 5 | | | | | 10 | | | | | 15 | |

Gln His Gly Phe Ala Phe Gln Ser Gly Gln Val Leu Ser Ala Leu Pro
                20                  25                  30

Arg Thr Ser Arg Gln Val Gln Leu Leu Gln Asn Leu Thr Thr Thr Tyr
            35                  40                  45

Glu Val Val Leu Trp Gln Pro Val Thr Ala Glu Phe Ile Glu Lys Lys
 50                  55                  60

Lys Glu Val His Phe Phe Val Asn Ala Ser Asp Val Asp Ser Val Lys
 65                  70                  75                  80

Ala His Leu Asn Val Ser Arg Ile Pro Phe Asn Val Leu Met Asn Asn
                85                  90                  95

Val Glu Asp Leu Ile Glu Gln Gln Thr Phe Asn Asp Thr Val Ser Pro
            100                 105                 110

Arg Ala Ser Ala Ser Tyr Tyr Glu Gln Tyr His Ser Leu Asn Glu Ile
        115                 120                 125

Tyr Ser Trp Ile Glu Val Ile Thr Glu Gln His Pro Asp Met Leu Gln
130                 135                 140

Lys Ile Tyr Ile Gly Ser Ser Phe Glu Lys Tyr Pro Leu Tyr Val Leu
145                 150                 155                 160

Lys Val Ser Gly Lys Glu Gln Arg Ile Lys Asn Ala Ile Trp Ile Asp
                165                 170                 175

Cys Gly Ile His Ala Arg Glu Trp Ile Ser Pro Ala Phe Cys Leu Trp
            180                 185                 190

Phe Ile Gly Tyr Val Thr Gln Phe His Gly Lys Glu Asn Leu Tyr Thr
        195                 200                 205

Arg Leu Leu Arg His Val Asp Phe Tyr Ile Met Pro Val Met Asn Val
210                 215                 220

Asp Gly Tyr Asp Tyr Thr Trp Lys Lys Asn Arg Met Trp Arg Lys Asn
225                 230                 235                 240

Arg Ser Ala His Lys Asn Asn Arg Cys Val Gly Thr Asp Leu Asn Arg
                245                 250                 255

Asn Phe Ala Ser Lys His Trp Cys Glu Lys Gly Ala Ser Ser Ser Ser
            260                 265                 270

Cys Ser Glu Thr Tyr Cys Gly Leu Tyr Pro Glu Ser Glu Pro Glu Val
        275                 280                 285

Lys Ala Val Ala Asp Phe Leu Arg Arg Asn Ile Asp His Ile Lys Ala
290                 295                 300

Tyr Ile Ser Met His Ser Tyr Ser Gln Gln Ile Leu Phe Pro Tyr Ser
305                 310                 315                 320

Tyr Asn Arg Ser Lys Ser Lys Asp His Glu Glu Leu Ser Leu Val Ala
                325                 330                 335

Ser Glu Ala Val Arg Ala Ile Glu Ser Ile Asn Lys Asn Thr Arg Tyr
            340                 345                 350

Thr His Gly Ser Gly Ser Glu Ser Leu Tyr Leu Ala Pro Gly Gly Ser
        355                 360                 365

```
Asp Asp Trp Ile Tyr Asp Leu Gly Ile Lys Tyr Ser Phe Thr Ile Glu
    370                 375                 380

Leu Arg Asp Thr Gly Arg Tyr Gly Phe Leu Leu Pro Glu Arg Tyr Ile
385                 390                 395                 400

Lys Pro Thr Cys Ala Glu Ala Leu Ala Ala Ile Ser Lys Ile Val Trp
                405                 410                 415

His Val Ile Arg Asn Thr
            420
```

<210> SEQ ID NO 19
<211> LENGTH: 298
<212> TYPE: PRT
<213> ORGANISM: Bos taurus

<400> SEQUENCE: 19

```
Ala Thr Tyr His Thr Leu Asp Glu Ile Tyr Asp Phe Met Asp Leu Leu
1               5                   10                  15

Val Ala Gln His Pro Glu Leu Val Ser Lys Leu Gln Ile Gly Arg Ser
                20                  25                  30

Tyr Glu Gly Arg Pro Ile Tyr Val Leu Lys Phe Ser Thr Gly Gly Ser
                35                  40                  45

Asn Arg Pro Ala Ile Trp Ile Asp Leu Gly Ile His Ser Arg Glu Trp
50                  55                  60

Ile Thr Gln Ala Thr Gly Val Trp Phe Ala Lys Lys Phe Thr Glu Asn
65                  70                  75                  80

Tyr Gly Gln Asn Pro Ser Phe Thr Ala Ile Leu Asp Ser Met Asp Ile
                85                  90                  95

Phe Leu Glu Ile Val Thr Asn Pro Asn Gly Phe Ala Phe Thr His Ser
                100                 105                 110

Glu Asn Arg Leu Trp Arg Lys Thr Arg Ser Val Thr Ser Ser Ser Leu
                115                 120                 125

Cys Val Gly Val Asp Ala Asn Arg Asn Trp Asp Ala Gly Phe Gly Lys
    130                 135                 140

Ala Gly Ala Ser Ser Ser Pro Cys Ser Glu Thr Tyr His Gly Lys Tyr
145                 150                 155                 160

Ala Asn Ser Glu Val Glu Val Lys Ser Ile Val Asp Phe Val Lys Asn
                165                 170                 175

His Gly Asn Phe Lys Ala Phe Leu Ser Ile His Ser Tyr Ser Gln Leu
                180                 185                 190

Leu Leu Tyr Pro Tyr Gly Tyr Thr Thr Gln Ser Ile Pro Asp Lys Thr
            195                 200                 205

Glu Leu Asn Gln Val Ala Lys Ser Ala Val Ala Ala Leu Lys Ser Leu
    210                 215                 220

Tyr Gly Thr Ser Tyr Lys Tyr Gly Ser Ile Ile Thr Thr Ile Tyr Gln
225                 230                 235                 240

Ala Ser Gly Gly Ser Ile Asp Trp Ser Tyr Asn Gln Gly Ile Lys Tyr
                245                 250                 255

Ser Phe Thr Phe Glu Leu Arg Asp Thr Gly Arg Tyr Gly Phe Leu Leu
                260                 265                 270

Pro Ala Ser Gln Ile Ile Pro Thr Ala Gln Glu Thr Trp Leu Gly Val
            275                 280                 285

Leu Thr Ile Met Glu His Thr Val Asn Asn
            290                 295
```

<210> SEQ ID NO 20

<211> LENGTH: 402
<212> TYPE: PRT
<213> ORGANISM: Homo sapiens

<400> SEQUENCE: 20

```
His His Gly Gly Glu His Phe Glu Gly Lys Val Phe Arg Val Asn
1               5                   10                  15

Val Glu Asp Glu Asn His Ile Asn Ile Ile Arg Glu Leu Ala Ser Thr
                20                  25                  30

Thr Gln Ile Asp Phe Trp Lys Pro Asp Ser Val Thr Gln Ile Lys Pro
                35                  40                  45

His Ser Thr Val Asp Phe Arg Val Lys Ala Glu Asp Thr Val Thr Val
        50                  55                  60

Glu Asn Val Leu Lys Gln Asn Glu Leu Gln Tyr Lys Val Leu Ile Ser
65                  70                  75                  80

Asn Leu Arg Asn Val Val Glu Ala Gln Phe Asp Ser Arg Val Arg Ala
                85                  90                  95

Thr Gly His Ser Tyr Glu Lys Tyr Asn Lys Trp Glu Thr Ile Glu Ala
                100                 105                 110

Trp Thr Gln Gln Val Ala Thr Glu Asn Pro Ala Leu Ile Ser Arg Ser
                115                 120                 125

Val Ile Gly Thr Thr Phe Glu Gly Arg Ala Ile Tyr Leu Leu Lys Val
130                 135                 140

Gly Lys Ala Gly Gln Asn Lys Pro Ala Ile Phe Met Asp Cys Gly Phe
145                 150                 155                 160

His Ala Arg Glu Trp Ile Ser Pro Ala Phe Cys Gln Trp Phe Val Arg
                165                 170                 175

Glu Ala Val Arg Thr Tyr Gly Arg Glu Ile Gln Val Thr Glu Leu Leu
                180                 185                 190

Asn Lys Leu Asp Phe Tyr Val Leu Pro Val Leu Asn Ile Asp Gly Tyr
                195                 200                 205

Ile Tyr Thr Trp Thr Lys Ser Arg Phe Trp Arg Lys Thr Arg Ser Thr
210                 215                 220

His Thr Gly Ser Ser Cys Ile Gly Thr Asp Pro Asn Arg Asn Phe Asp
225                 230                 235                 240

Ala Gly Trp Cys Glu Ile Gly Ala Ser Arg Asn Pro Cys Asp Glu Thr
                245                 250                 255

Tyr Cys Gly Pro Ala Ala Glu Ser Glu Lys Glu Thr Lys Ala Leu Ala
                260                 265                 270

Asp Phe Ile Arg Asn Lys Leu Ser Ser Ile Lys Ala Tyr Leu Thr Ile
                275                 280                 285

His Ser Tyr Ser Gln Met Met Ile Tyr Pro Tyr Ser Tyr Ala Tyr Lys
                290                 295                 300

Leu Gly Glu Asn Asn Ala Glu Leu Asn Ala Leu Ala Lys Ala Thr Val
305                 310                 315                 320

Lys Glu Leu Ala Ser Leu His Gly Thr Lys Tyr Thr Tyr Gly Pro Gly
                325                 330                 335

Ala Thr Thr Ile Tyr Pro Ala Ala Gly Gly Ser Asp Asp Trp Ala Tyr
                340                 345                 350

Asp Gln Gly Ile Arg Tyr Ser Phe Thr Phe Glu Leu Arg Asp Thr Gly
                355                 360                 365

Arg Tyr Gly Phe Leu Leu Pro Glu Ser Gln Ile Arg Ala Thr Cys Glu
370                 375                 380

Glu Thr Phe Leu Ala Ile Lys Tyr Val Ala Ser Tyr Val Leu Glu His
```

```
385             390             395             400
Leu Tyr

<210> SEQ ID NO 21
<211> LENGTH: 39
<212> TYPE: DNA
<213> ORGANISM: Papio hamadryas

<400> SEQUENCE: 21
gcagcagcgg ccgctttcag agtggccagg ttctagctg                    39

<210> SEQ ID NO 22
<211> LENGTH: 37
<212> TYPE: DNA
<213> ORGANISM: Papio hamadryas

<400> SEQUENCE: 22
gcagcagtcg acaacattcc taatgacatg ccaagct                      37

<210> SEQ ID NO 23
<211> LENGTH: 39
<212> TYPE: DNA
<213> ORGANISM: Papio hamadryas

<400> SEQUENCE: 23
gcagcagcgg ccgcatgaag ctttgcagtc ttgcagtcc                    39

<210> SEQ ID NO 24
<211> LENGTH: 37
<212> TYPE: DNA
<213> ORGANISM: Papio hamadryas

<400> SEQUENCE: 24
gcagcagtcg acgatgtaac gctcaggcag caagaat                      37
```